(12) United States Patent
Dota

(10) Patent No.: US 9,822,095 B2
(45) Date of Patent: Nov. 21, 2017

(54) TETRAZOLINONE COMPOUND AND APPLICATION THEREOF

(71) Applicant: SUMITOMO CHEMICAL COMPANY, LIMITED, Tokyo (JP)

(72) Inventor: Koichiro Dota, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/128,664

(22) PCT Filed: Mar. 26, 2015

(86) PCT No.: PCT/JP2015/060405
§ 371 (c)(1),
(2) Date: Sep. 23, 2016

(87) PCT Pub. No.: WO2015/147337
PCT Pub. Date: Oct. 1, 2015

(65) Prior Publication Data
US 2017/0107196 A1    Apr. 20, 2017

(30) Foreign Application Priority Data
Mar. 28, 2014 (JP) ................. 2014-067945

(51) Int. Cl.
*A01N 43/72* (2006.01)
*C07D 401/10* (2006.01)
*C07D 401/12* (2006.01)
*A01N 43/713* (2006.01)
*C07D 257/04* (2006.01)

(52) U.S. Cl.
CPC ......... *C07D 401/12* (2013.01); *A01N 43/713* (2013.01); *C07D 257/04* (2013.01); *C07D 401/10* (2013.01)

(58) Field of Classification Search
CPC .. C07D 401/12; C07D 257/04; C07D 401/10; A01N 43/72
See application file for complete search history.

(56) References Cited

U.S. PATENT DOCUMENTS

| 5,589,439 | A | 12/1996 | Goto et al. |
| 5,641,727 | A | 6/1997 | Goto et al. |
| 5,861,359 | A | 1/1999 | Theodoridis |
| 6,294,503 | B1 | 9/2001 | Gupta et al. |
| 6,583,090 | B1 | 6/2003 | Gewehr et al. |
| 2014/0323305 | A1 | 10/2014 | Rheinheimer et al. |
| 2015/0031733 | A1 | 1/2015 | Yoshimoto et al. |
| 2015/0051171 | A1 | 2/2015 | Yoshimoto et al. |
| 2015/0203511 | A1 | 7/2015 | Arimori et al. |
| 2015/0223460 | A1 | 8/2015 | Arimori et al. |
| 2015/0299146 | A1 | 10/2015 | Hasegawa et al. |
| 2015/0336908 | A1 | 11/2015 | Shioda et al. |
| 2016/0081339 | A1 | 3/2016 | Yoshimoto et al. |
| 2016/0081340 | A1 | 3/2016 | Arimori et al. |
| 2016/0150787 | A1 | 6/2016 | Azuma et al. |
| 2016/0157489 | A1 | 6/2016 | Shioda et al. |
| 2016/0159755 | A1 | 6/2016 | Shioda et al. |
| 2016/0174558 | A1 | 6/2016 | Hou et al. |
| 2016/0205935 | A1 | 7/2016 | Akioka et al. |
| 2016/0249617 | A1 | 9/2016 | Dota |
| 2016/0272622 | A1 | 9/2016 | Azuma et al. |
| 2016/0311775 | A1 | 10/2016 | Shioda et al. |

FOREIGN PATENT DOCUMENTS

| CN | 102875540 A | 1/2013 |
| EP | 0 902 028 A1 | 3/1999 |
| JP | 8-81459 A | 3/1996 |
| JP | 8-99975 A | 4/1996 |
| JP | 9-87281 A | 3/1997 |
| JP | 9-100272 A | 4/1997 |
| JP | 9-100277 A | 4/1997 |
| JP | 9-110863 A | 4/1997 |
| JP | 9-208565 A | 8/1997 |
| JP | 11-152278 A | 6/1999 |
| JP | 2001-512460 A | 8/2001 |
| WO | WO 96/36229 A1 | 11/1996 |
| WO | WO 98/25912 A1 | 6/1998 |
| WO | WO 98/35961 A1 | 8/1998 |
| WO | WO 98/51683 A1 | 11/1998 |

(Continued)

OTHER PUBLICATIONS

International Search Report for PCT/JP2015/060405 dated May 26, 2015.

(Continued)

*Primary Examiner* — Rebecca Anderson
*Assistant Examiner* — Karen Cheng
(74) *Attorney, Agent, or Firm* — Birch, Stewart, Kolasch & Birch, LLP

(57) ABSTRACT

A tetrazolinone compound represented by formula (1):

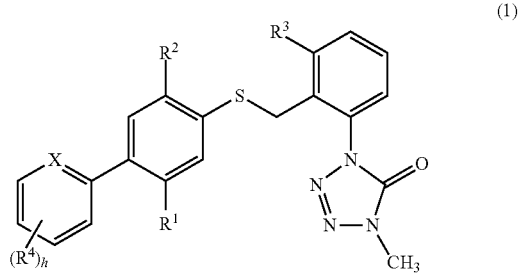

wherein $R^1$ and $R^2$ each independently represents a hydrogen atom, a C1-C4 alkyl group optionally having one or more halogen atoms, etc.; $R^3$ represents a hydrogen atom, a C1-C4 alkyl group optionally having one or more halogen atoms, etc.; $R^4$ represents a halogen atom, a C1-C4 alkyl group optionally having one or more halogen atoms, etc.; h represents any one of integers of 0 to 4; X represents a nitrogen atom or $CR^5$; and $R^5$ represents a hydrogen atom, a halogen atom, etc.; has excellent control activity against pests.

3 Claims, No Drawings

(56) References Cited

FOREIGN PATENT DOCUMENTS

| WO | WO 99/46246 A1 | 9/1999 |
|----|----|----|
| WO | WO 99/48890 A1 | 9/1999 |
| WO | WO 2013/092224 A1 | 6/2013 |
| WO | WO 2013/162072 A1 | 10/2013 |
| WO | WO 2013/162077 A1 | 10/2013 |
| WO | WO 2014/051161 A1 | 4/2014 |
| WO | WO 2014/051165 A1 | 4/2014 |
| WO | WO 2014/084223 A1 | 6/2014 |
| WO | WO 2014/104268 A1 | 7/2014 |
| WO | WO 2014/104382 A1 | 7/2014 |
| WO | WO 2014/104384 A1 | 7/2014 |
| WO | WO 2014/175465 A1 | 10/2014 |
| WO | WO 2014/19295 A1 | 12/2014 |
| WO | WO 2015/005499 A1 | 1/2015 |
| WO | WO 2015/016335 A1 | 2/2015 |
| WO | WO 2015/016372 A1 | 2/2015 |
| WO | WO 2015/016373 A1 | 2/2015 |
| WO | WO 2015/030217 A1 | 3/2015 |
| WO | WO 2015/041360 A1 | 3/2015 |
| WO | WO 2015/046480 A1 | 4/2015 |
| WO | WO 2015/050039 A1 | 4/2015 |
| WO | WO 2015/050040 A1 | 4/2015 |
| WO | WO 2015/056806 A1 | 4/2015 |
| WO | WO 2015/060461 A1 | 4/2015 |
| WO | WO 2015/088038 A1 | 6/2015 |
| WO | WO 2015/147314 A1 | 10/2015 |
| WO | WO 2015/147336 A1 | 10/2015 |

OTHER PUBLICATIONS

English translation of the Written Opinion of the International Searching Authority (Form PCT/ISA/237) for International Application No. PCT/JP2014/078005, dated Nov. 25, 2014.

European Patent Office Communication and extended search report issued in the corresponding European Patent Application No. 15767811.1 dated Jul. 5, 2017.

TETRAZOLINONE COMPOUND AND APPLICATION THEREOF

TECHNICAL FIELD

The present invention relates to a tetrazolinone compound and application thereof.

BACKGROUND ART

Heretofore, various chemicals have been developed so as to control pests and provided in practice use, but in some cases, these chemicals may not exert enough activity.

Meanwhile, there have been known, as compounds for controlling pests, compounds having a tetrazolinone ring represented by the following formula (A):

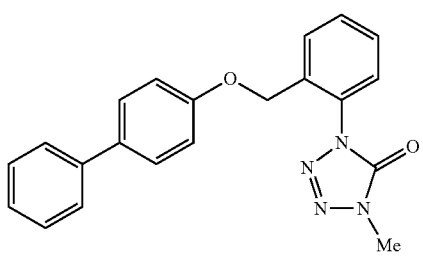

(A)

(see WO 96/36229 A).

The present invention provides compounds having excellent control activity against pests.

DISCLOSURE OF THE INVENTION

The present inventors have intensively studied so as to find compounds having excellent control activity against pests, and found that a tetrazolinone compound represented by the following formula (1) has excellent control activity against pests, thus completing the present invention.

The present invention includes the followings [1] to [8].
[1] A tetrazolinone compound represented by formula (1):

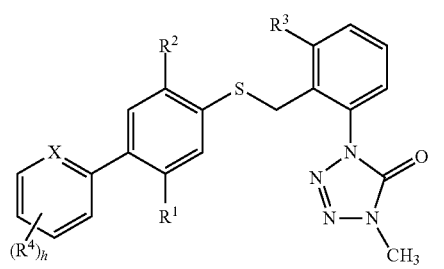

(1)

wherein $R^1$ and $R^2$ each independently represents a hydrogen atom, a halogen atom, a C1-C4 alkyl group optionally having one or more halogen atoms, or a C1-C4 alkoxy group optionally having one or more halogen atoms;
$R^3$ represents a hydrogen atom, a halogen atom, a C1-C4 alkyl group optionally having one or more halogen atoms, a C3-C4 cycloalkyl group optionally having one or more halogen atoms, or a C1-C4 alkoxy group optionally having one or more halogen atoms;

$R^4$ represents a halogen atom, a C1-C4 alkyl group optionally having one or more halogen atoms, a C1-C4 alkoxy group optionally having one or more halogen atoms, or a cyano group;
h represents any one of integers of 0 to 4 in which when h is an integer of 2 or more, each $R^4$ may be the same as or different from the other at least one $R^4$;
X represents a nitrogen atom or $CR^5$; and
$R^5$ represents a hydrogen atom, a halogen atom, a C1-C4 alkyl group optionally having one or more halogen atoms, a C1-C4 alkoxy group optionally having one or more halogen atoms, or a cyano group.
[2] The tetrazolinone compound according to [1], wherein the compound X is a nitrogen atom.
[3] The tetrazolinone compound according to [1], wherein X is $CR^5$.
[4] A pest control agent comprising the tetrazolinone compound according to any one of [1] to [3].
[5] A method for control pests, which comprises applying an effective amount of the tetrazolinone compound according to any one of [1] to [3] to plants or soil.
[6] Use of the tetrazolinone compound according to any one of [1] to [3] for controlling pests.

According to the present invention, pests can be controlled.

MODE FOR CARRYING OUT THE INVENTION

In the present invention, a tetrazolinone compound represented by formula (1) is referred to as the present compound, and a pest control agent containing the present compound is referred to as the present control agent.

Substituents as used herein will be mentioned below.

The halogen atom represents a fluorine atom, a chlorine atom, a bromine atom, and an iodine atom.

Examples of the C1-C4 alkyl group optionally having one or more halogen atoms include a methyl group, an ethyl group, a propyl group, an isopropyl group, a butyl group, an isobutyl group, a sec-butyl group, a tert-butyl group, a fluoromethyl group, a chloromethyl group, a dichloromethyl group, a difluoromethyl group, a trifluoromethyl group, a trichloromethyl group, a 2-fluoroethyl group, a 2,2,2-trifluoroethyl group, and a 1-trifluoromethyl-2,2,2-trifluoroethyl group.

Examples of the C1-C4 alkoxy group optionally having one or more halogen atoms include a methoxy group, an ethoxy group, a propyloxy group, an isopropyloxy group, a butyloxy group, a trifluoromethoxy group, a difluoromethoxy group, a 2-fluoroethoxy group, a 2,2,2-trifluoroethoxy group, a 3-chloropropoxy group, and a 3-chlorobutyloxy group.

Examples of the C3-C4 cycloalkyl group optionally having one or more halogen atoms include a cyclopropyl group, a cyclobutyl group, a 2,2-dichlorocyclopropyl group, and a 2,2-difluorocyclopropyl group.

Examples of Aspect of the present compound include the following compounds.
A tetrazolinone compound in which $R^3$ is a hydrogen atom in formula (1).
A tetrazolinone compound in which $R^3$ is a halogen atom in formula (1).
A tetrazolinone compound in which $R^3$ is a C1-C4 alkyl group optionally having one or more halogen atoms in formula (1).
A tetrazolinone compound in which $R^3$ is a C3-C4 cycloalkyl group optionally having one or more halogen atoms in formula (1).

A tetrazolinone compound in which R³ is a C1-C4 alkoxy group optionally having one or more halogen atoms in formula (1).
A tetrazolinone compound in which R² is a hydrogen atom in formula (1).
A tetrazolinone compound in which R² is a halogen atom in formula (1).
A tetrazolinone compound in which R² is a C1-C4 alkyl group optionally having one or more halogen atoms in formula (1).
A tetrazolinone compound in which R² is a C3-C4 cycloalkyl group optionally having one or more halogen atoms in formula (1).
A tetrazolinone compound in which R² is a C1-C4 alkoxy group optionally having one or more halogen atoms in formula (1).
A tetrazolinone compound in which R² is a hydrogen atom in formula (1).
A tetrazolinone compound in which R² is a halogen atom in formula (1).
A tetrazolinone compound in which R² is a C1-C4 alkyl group optionally having one or more halogen atoms in formula (1).
A tetrazolinone compound in which R² is a C3-C4 cycloalkyl group optionally having one or more halogen atoms in formula (1).
A tetrazolinone compound in which R² is a C1-C4 alkoxy group optionally having one or more halogen atoms in formula (1).
A tetrazolinone compound in which R³ is a C1-C4 alkyl group optionally having one or more halogen atoms, R² is a C1-C4 alkyl group optionally having one or more halogen atoms, or a halogen atom, R² is a hydrogen atom, and each of R⁴ is a hydrogen atom, a halogen atom, a C1-C4 alkyl group optionally having one or more halogen atoms, or a C1-C4 alkoxy group optionally having one or more halogen atoms in formula (1).
A tetrazolinone compound in which R² is a hydrogen atom or a C1-C4 alkyl group optionally having one or more halogen atoms, R² is a hydrogen atom or a C1-C4 alkyl group optionally having one or more halogen atoms, and R³ is a C1-C4 alkyl group optionally having one or more halogen atoms in formula (1).
A tetrazolinone compound in which X is a nitrogen atom, R² is a hydrogen atom or a C1-C4 alkyl group optionally having one or more halogen atoms, R² is a C1-C4 alkyl group optionally having one or more halogen atoms, and R³ is a C1-C4 alkyl group optionally having one or more halogen atoms in formula (1).
A tetrazolinone compound in which X is CR⁵, R¹ is a hydrogen atom, R² is a hydrogen atom or a C1-C4 alkyl group optionally having one or more halogen atoms, R³ is a C1-C4 alkyl group optionally having one or more halogen atoms, and R⁵ is a hydrogen atom or a C1-C4 alkyl group optionally having one or more halogen atoms in formula (1).
A tetrazolinone compound in which X is CR⁵, R¹ is a hydrogen atom or a C1-C4 alkyl group optionally having one or more halogen atoms, R² is a hydrogen atom or a C1-C4 alkyl group optionally having one or more halogen atoms, R³ is a C1-C4 alkyl group optionally having one or more halogen atoms, R⁵ is a hydrogen atom or a C1-C4 alkyl group optionally having one or more halogen atoms, h is 1, and R⁴ is a halogen atom, a C1-C4 alkyl group optionally having one or more halogen atoms, or a C1-C4 alkoxy group optionally having one or more halogen atoms in formula (1).

[Aspect 1]
A tetrazolinone compound represented by formula (1a):

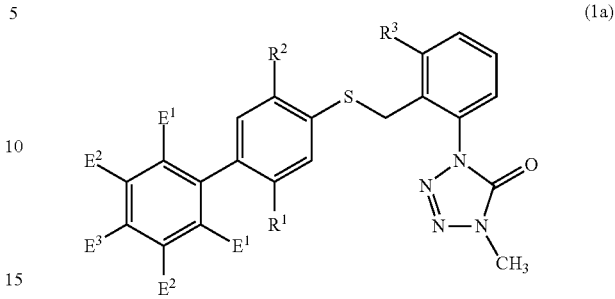

wherein E¹, E², and E³ each independently represents a halogen atom, a C1-C4 alkyl group optionally having one or more halogen atoms, a C1-C4 alkoxy group optionally having one or more halogen atoms, or a cyano group, and R¹, R², and R³ are the same as defined above (in which two E¹ (s) and two E² (s) may be the same or different to each other)].
A tetrazolinone compound in which R³ is a C1-C4 alkyl group optionally having one or more halogen atoms, or a hydrogen atom in [Aspect 1].
A tetrazolinone compound in which R³ is a C1-C4 alkyl group optionally having one or more halogen atoms, a halogen atom, or a C1-C4 alkoxy group optionally having one or more halogen atoms in [Aspect 1].
A tetrazolinone compound in which R³ is a C3-C4 cycloalkyl group optionally having one or more halogen atoms in [Aspect 1].
A tetrazolinone compound in which R³ is a hydrogen atom or a halogen atom in [Aspect 1].
A tetrazolinone compound in which R³ is a hydrogen atom in [Aspect 1].
A tetrazolinone compound in which R³ is a halogen atom in [Aspect 1].
A tetrazolinone compound in which R³ is a methyl group in [Aspect 1].
A tetrazolinone compound in which R³ is an ethyl group in [Aspect 1].
A tetrazolinone compound in which R³ is a methoxy group in [Aspect 1].
A tetrazolinone compound in which R³ is a cyclopropyl group in [Aspect 1].
A tetrazolinone compound in which R³ is a C1-C4 alkyl group optionally having one or more halogen atoms, a C1-C4 alkoxy group optionally having one or more halogen atoms, or a C3-C4 cycloalkyl group optionally having one or more halogen atoms, R¹ is a hydrogen atom or a C1-C4 alkyl group optionally having one or more halogen atoms, R² is a hydrogen atom or a C1-C4 alkyl group optionally having one or more halogen atoms, and E¹, E², and E³ are hydrogen atoms, halogen atoms, C1-C4 alkyl groups optionally having one or more halogen atoms, or C1-C4 alkoxy groups optionally having one or more halogen atoms in [Aspect 1].
A tetrazolinone compound in which R³ is a C1-C4 alkyl group optionally having one or more halogen atoms, a C1-C4 alkoxy group optionally having one or more halogen atoms, or a C3-C4 cycloalkyl group optionally having one or more halogen atoms, R¹ is a hydrogen atom or a C1-C4 alkyl group optionally having one or more halogen atoms, R² is a hydrogen atom or a C1-C4 alkyl group optionally having one or more halogen atoms, E¹ is a hydrogen atom or a C1-C4 alkyl group optionally having one or more halogen atoms, $E^2$ is a hydrogen atom, a halogen atom, or a C1-C4 alkyl group optionally having one or more halogen atoms, and $E^3$ is a hydrogen atom, a C1-C4 alkyl group optionally having one or more halogen atoms, or a C1-C4 alkoxy group optionally having one or more halogen atoms in [Aspect 1].

A tetrazolinone compound in which $R^3$ is a C1-C4 alkyl group optionally having one or more halogen atoms, a C1-C4 alkoxy group optionally having one or more halogen atoms, or a C3-C4 cycloalkyl group optionally having one or more halogen atoms, $R^1$ is a hydrogen atom, $R^2$ is a C1-C4 alkyl group optionally having one or more halogen atoms, $E^1$ is a hydrogen atom or a C1-C4 alkyl group optionally having one or more halogen atoms, $E^2$ is a hydrogen atom, a halogen atom, or a C1-C4 alkyl group optionally having one or more halogen atoms, and $E^3$ is a hydrogen atom, a C1-C4 alkyl group optionally having one or more halogen atoms, or a C1-C4 alkoxy group optionally having one or more halogen atoms in [Aspect 1].

A tetrazolinone compound in which $R^3$ is a C1-C4 alkyl group optionally having one or more halogen atoms, $R^1$ is a hydrogen atom, $R^2$ is a hydrogen atom or a C1-C4 alkyl group optionally having one or more halogen atoms, $E^1$ is a hydrogen atom or a C1-C4 alkyl group optionally having one or more halogen atoms, $E^2$ is a hydrogen atom, a halogen atom, or a C1-C4 alkyl group optionally having one or more halogen atoms, and $E^3$ is a hydrogen atom, a C1-C4 alkyl group optionally having one or more halogen atoms, or a C1-C4 alkoxy group optionally having one or more halogen atoms in [Aspect 1].

[Aspect 2]
A tetrazolinone compound represented by formula (1b):

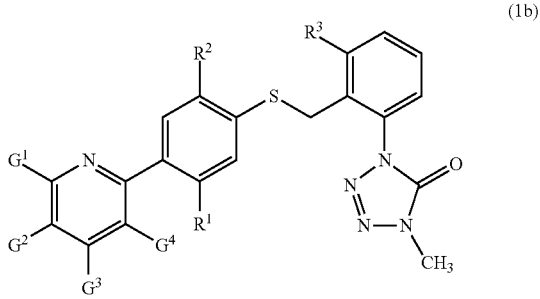

wherein $G^1$, $G^2$, $G^3$, and $G^4$ each independently represents a halogen atom, a C1-C4 alkyl group optionally having one or more halogen atoms, a C1-C4 alkoxy group optionally having one or more halogen atoms, or a cyano group, and $R^1$, $R^2$, and $R^3$ are the same as defined above.

A tetrazolinone compound in which $R^3$ is a C1-C4 alkyl group optionally having one or more halogen atoms, or a hydrogen atom in [Aspect 2].

A tetrazolinone compound in which $R^3$ is a C1-C4 alkyl group optionally having one or more halogen atoms, a halogen atom, or a C1-C4 alkoxy group optionally having one or more halogen atoms in [Aspect 2].

A tetrazolinone compound in which $R^3$ is a C3-C4 cycloalkyl group optionally having one or more halogen atoms in [Aspect 2].

A tetrazolinone compound in which $R^3$ is a hydrogen atom or a halogen atom in [Aspect 2].

A tetrazolinone compound in which $R^3$ is a hydrogen atom in [Aspect 2].

A tetrazolinone compound in which $R^3$ is a halogen atom in [Aspect 2].

A tetrazolinone compound in which $R^3$ is a methyl group in [Aspect 2].

A tetrazolinone compound in which $R^3$ is an ethyl group in [Aspect 2].

A tetrazolinone compound in which $R^3$ is a methoxy group in [Aspect 2].

A tetrazolinone compound in which $R^3$ is a cyclopropyl group in [Aspect 2].

A tetrazolinone compound in which $R^3$ is a C1-C4 alkyl group optionally having one or more halogen atoms, a C1-C4 alkoxy group optionally having one or more halogen atoms, or a C3-C4 cycloalkyl group optionally having one or more halogen atoms, $R^1$ is a hydrogen atom or a C1-C4 alkyl group optionally having one or more halogen atoms, $R^2$ is a hydrogen atom or a C1-C4 alkyl group optionally having one or more halogen atoms, and each of $G^1$, $G^2$, $G^3$, and $G^4$ is a hydrogen atom in [Aspect 2].

A tetrazolinone compound in which $R^3$ is a C1-C4 alkyl group optionally having one or more halogen atoms, a C1-C4 alkoxy group optionally having one or more halogen atoms, or a C3-C4 cycloalkyl group optionally having one or more halogen atoms, $R^1$ is a hydrogen atom or a C1-C4 alkyl group optionally having one or more halogen atoms, $R^2$ is a hydrogen atom or a C1-C4 alkyl group optionally having one or more halogen atoms, $G^1$ and $G^3$ are hydrogen atoms, halogen atoms, C1-C4 alkyl groups optionally having one or more halogen atoms, or C1-C4 alkoxy groups optionally having one or more halogen atoms, and $G^2$ and $G^4$ are hydrogen atoms in [Aspect 2].

A tetrazolinone compound in which $R^3$ is a C1-C4 alkyl group optionally having one or more halogen atoms, a C1-C4 alkoxy group optionally having one or more halogen atoms, or a C3-C4 cycloalkyl group optionally having one or more halogen atoms, $R^1$ is a hydrogen atom or a C1-C4 alkyl group optionally having one or more halogen atoms, $R^2$ is a hydrogen atom or a C1-C4 alkyl group optionally having one or more halogen atoms, and each of $G^1$, $G^2$, $G^3$, and $G^4$ is a hydrogen atom in [Aspect 2].

A tetrazolinone compound in which $R^3$ is a C1-C4 alkyl group optionally having one or more halogen atoms, a C1-C4 alkoxy group optionally having one or more halogen atoms, or a C3-C4 cycloalkyl group optionally having one or more halogen atoms, $R^1$ is a hydrogen atom, $R^2$ is a C1-C4 alkyl group optionally having one or more halogen atoms, and each of $G^1$, $G^2$, $G^3$, and $G^4$ is a hydrogen atom in [Aspect 2].

A tetrazolinone compound in which $R^3$ is a C1-C4 alkyl group optionally having one or more halogen atoms, $R^1$ is a hydrogen atom or a C1-C4 alkyl group optionally having one or more halogen atoms, $R^2$ is a C1-C4 alkyl group optionally having one or more halogen atoms, and each of $G^1$, $G^2$, $G^3$, and $G^4$ is a hydrogen atom in [Aspect 2].

Next, a process for producing the present compound will be described.

The present compound can be produced, for example, by the following Production Processes.

(Production Process A)

The present compound can be produced by subjecting a compound represented by formula (A-1) (hereinafter referred to as the compound (A-1)) and a compound represented by formula (A-2) (hereinafter referred to as the compound (A-2)) to a coupling reaction in the presence of a base and a catalyst:

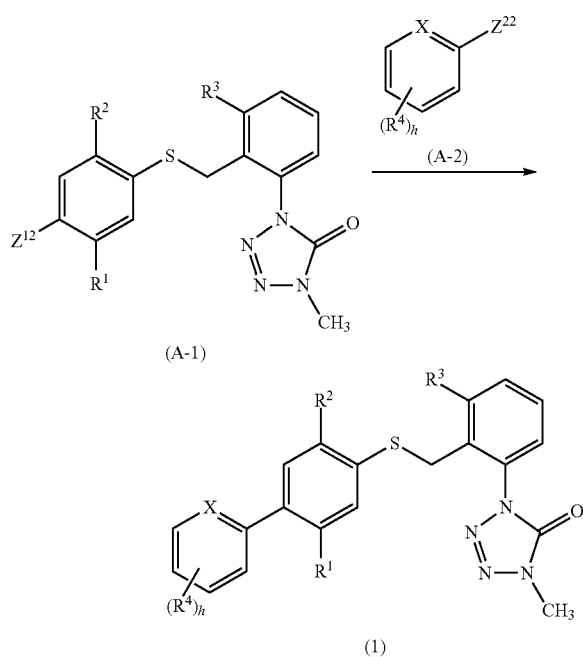

wherein $R^1$, $R^2$, $R^3$, $R^4$, X and h are the same as defined above, $Z^{12}$ represents $B(OH)_2$, a dialkoxyboranyl group, or trifluoroborate ($BF_3^-K^+$), and $Z^{22}$ represents a chlorine atom, a bromine atom, or an iodine atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; mixtures thereof, and mixtures of water and these solvents.

It is possible to usually use, as the compound (A-1) to be used in the reaction, compounds produced by a known method mentioned in N. Miyaura and A. Suzuki, Chem. Rev., 1995, 95, 2457. It is possible to produce, as the compound (A-1) to be used in the reaction, a boronic acid ester derivative by reacting a compound (A-1-I) in which $Z^{12}$ is iodine in the compound (A-1) with butyllithium, followed by a reaction with a boric acid ester. It is possible to produce a boronic acid derivative by optionally hydrolyzing the boronic acid ester derivative obtained by the above-mentioned reaction. It is also possible to produce a trifluoroborate ($BF_3^-K^+$) by fluorinating the boronic acid ester derivative with potassium fluoride in accordance with a known method mentioned in Molander et al. Acc. Chem. Res., 2007, 40, 275.

Commercially available products are usually used as the compound (A-2) to be used in the reaction.

Examples of the catalyst to be used in the reaction include palladium(II) acetate, dichlorobis(triphenylphosphine)palladium, tetrakis(triphenylphosphine)palladium(0), palladium (II) acetate/triscyclohexylphosphine, bis(diphenylphosphinoferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium(II) acetate/ dicyclohexyl(2',4',6'-triisopropylbiphenyl-2-yl)phosphine, tris(dibenzylidineacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal fluorides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (A-2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (A-1).

The reaction temperature of the reaction is usually within a range of 0 to 150° C. The reaction time of the reaction is usually within a range of 0.1 to 24 hours.

After completion of the reaction, the present compound can be isolated by performing post-treatment operations such as extraction of the reaction mixture with an organic solvent, and drying and concentration of the organic layer. The isolated present compound can also be purified by chromatography, recrystallization, and the like.

(Production Process B)

The present compound can be produced by subjecting a compound represented by formula (B-1) (hereinafter referred to as the compound (B-1)) and a compound represented by formula (B-2) (hereinafter referred to as the compound (B-2)) to a coupling reaction in the presence of a base and a catalyst:

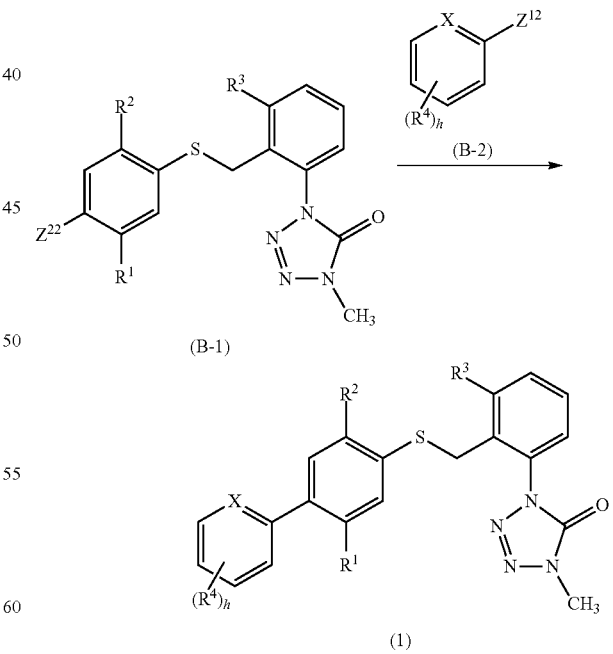

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; mixtures thereof, and mixtures of water and these solvents.

It is possible to usually use, as the compound (B-2) to be used in the reaction, commercially available compounds, or compounds produced by a known method mentioned in N. Miyaura and A. Suzuki, Chem. Rev., 1995, 95, 2457. It is possible to produce, as the compound (B-2) to be used in the reaction, a boronic acid ester derivative by reacting a compound (B-2-I) in which $Z^{22}$ is iodine in the compound (B-2) with butyllithium, followed by a reaction with a boric acid ester. It is possible to produce a boronic acid derivative by optionally hydrolyzing the boronic acid ester derivative obtained by the above-mentioned reaction. It is also possible to produce a trifluoroborate ($BF_3^-K^+$) by fluorinating the boronic acid ester with potassium fluoride in accordance with a known method mentioned in Molander et al. Acc. Chem. Res., 2007, 40, 275.

Examples of the catalyst to be used in the reaction include palladium(II) acetate, dichlorobis(triphenylphosphine)palladium, tetrakis(triphenylphosphine)palladium(0), palladium (II) acetate/triscyclohexylphosphine, bis(diphenylphosphinoferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene) palladium or palladium(II) acetate/dicyclohexyl(2',4',6'-triisopropylbiphenyl-2-yl)phosphine, tris(dibenzylidineacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal fluorides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (B-2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B-1).

The reaction temperature of the reaction is usually within a range of 0 to 150° C. The reaction time of the reaction is usually within a range of 0.1 to 24 hours.

After completion of the reaction, the present compound can be isolated by performing post-treatment operations such as extraction of the reaction mixture with an organic solvent, and drying and concentration of the organic layer. The isolated present compound can also be purified by chromatography, recrystallization, and the like.

The method for synthesizing an intermediate compound will be mentioned in detail below.

(Reference Production Process A)

A compound represented by formula (B-1) can be produced by reacting a compound represented by formula (AA-1) (hereinafter referred to as the compound (AA-1)) with a compound represented by formula (AA-2) (hereinafter referred to as the compound (AA-2)) in the presence of a base:

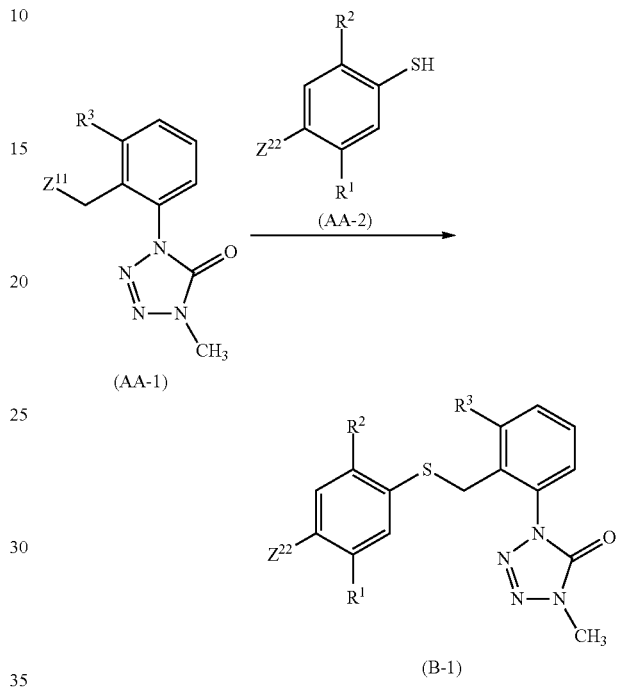

wherein $R^1$, $R^2$, and $R^3$ are the same as defined above, and $Z^{11}$ represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; mixtures thereof, and mixtures of water and these solvents.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; and alkali metal alkoxides such as sodium tert-butoxide and potassium tert-butoxide.

The compound (AA-1) can be produced in accordance with the method mentioned in WO 2013/162072 A.

In the reaction, the compound (AA-2) is usually used in the proportion within a range of 1 to 10 mols, and the base is usually used in the proportion within a range of 0.5 to 5 mols, based on 1 mol of the compound (AA-1).

The reaction temperature of the reaction is usually within a range of −20 to 150° C. The reaction time of the reaction is usually within a range of 0.1 to 24 hours.

In the reaction, if necessary, sodium iodide, tetrabutylammonium iodide, and the like may be added, and these compounds are usually used in the proportion within a range of 0.001 to 1.2 mols, based on 1 mol of the compound (AA-1).

After completion of the reaction, the compound (AA-3) can be isolated by performing post-treatment operations such as extraction of the reaction mixture with an organic solvent, and drying and concentration of the organic layer. The isolated compound (AA-3) can also be purified by chromatography, recrystallization, and the like.

(Reference Production Process B)

The compound (AA-2) can be produced by mixing a compound represented by formula (AA-4) (hereinafter referred to as the compound (AA-4)) with a base:

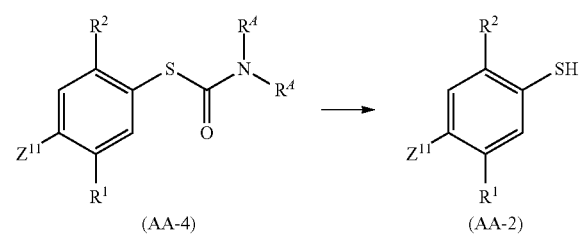

wherein $R^1$, $R^2$, and $Z^{11}$ are the same as defined above, and $R^4$ represents a C1-C6 alkyl group.

The reaction is usually performed in a solvent.

Examples of the solvent to be used in the reaction include alcohols such as methanol, ethanol, isopropanol, and butanol; hydrocarbons such as toluene and xylene; ethers such as tetrahydrofuran, 1,4-dioxane, ethylene glycol dimethyl ether, and anisole; acid amides such as dimethylformamide, 1,3-dimethyl-2-imidazolidinone, and N-methylpyrrolidone; sulfoxides such as dimethyl sulfoxide; nitriles such as acetonitrile; water and mixtures thereof.

Examples of the base to be used in the reaction include alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

In the reaction, the base is usually used in the proportion within a range of 0.5 to 5 mols based on 1 mol of the compound (AA-4).

The reaction temperature of the reaction is usually within a range of −20 to 150° C. The reaction time of the reaction is usually within a range of 0.1 to 24 hours.

After completion of the reaction, the compound (AA-2) can be isolated by performing post-treatment operations such as extraction of the reaction mixture with an organic solvent, and drying and concentration of the organic layer. The isolated compound (AA-2) can also be purified by chromatography, recrystallization, and the like.

(Reference Production Process C)

The compound (AA-4) can be produced by heating a compound represented by formula (AA-5) (hereinafter referred to as the compound (AA-5)) in the presence of a solvent:

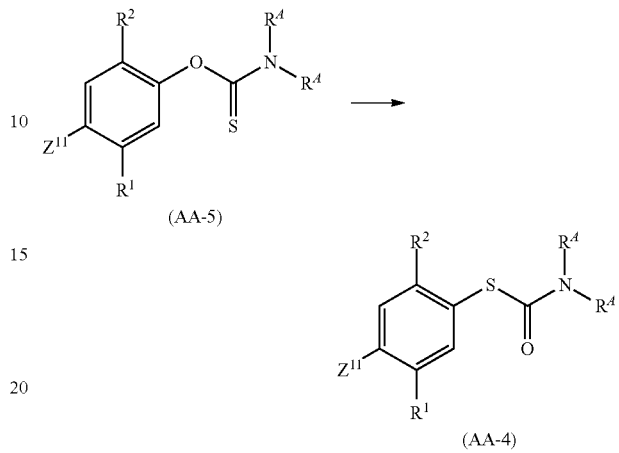

wherein symbols are the same as defined above.

The reaction is usually performed in a solvent.

Examples of the solvent to be used in the reaction include hydrocarbons such as toluene and xylene; ethers such as ethylene glycol dimethyl ether, anisole, and diphenyl ether; acid amides such as dimethylformamide, 1,3-dimethyl-2-imidazolidinone, and N-methylpyrrolidone; sulfoxides such as dimethyl sulfoxide; nitriles such as acetonitrile; and mixtures thereof.

The reaction temperature of the reaction is usually within a range of 20 to 300° C. The reaction time of the reaction is usually within a range of 0.1 to 50 hours.

After completion of the reaction, the compound (AA-4) can be isolated by performing post-treatment operations such as extraction of the reaction mixture with an organic solvent, and drying and concentration of the organic layer. The isolated compound (AA-4) can also be purified by chromatography, recrystallization, and the like.

(Reference Production Process D)

The compound (AA-5) can be produced by reacting a compound represented by formula (AA-6) (hereinafter referred to as the compound (AA-6)) with thiocarbamates represented by formula (AA-7) (hereinafter referred to as the compound (AA-7)) in the presence of a base:

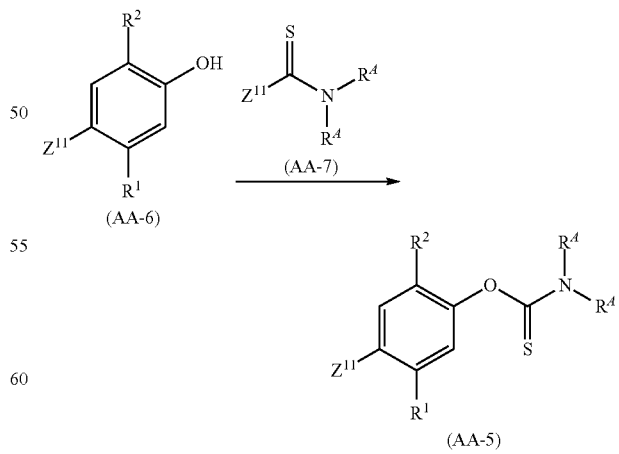

wherein symbols are the same as defined above.

The reaction is usually performed in a solvent.

Examples thereof include alcohols such as methanol, ethanol, isopropanol, and butanol; hydrocarbons such as toluene and xylene; ethers such as tetrahydrofuran, 1,4-dioxane, ethylene glycol dimethyl ether, and anisole; acid amides such as dimethylformamide, 1,3-dimethyl-2-imidazolidinone, and N-methylpyrrolidone; sulfoxides such as dimethyl sulfoxide; nitriles such as acetonitrile; water and mixtures thereof.

Examples of the base to be used in the reaction include alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; alkali metal alkoxides such as sodium tert-butoxide and potassium tert-butoxide.

Examples of the compound (AA-7) include commercially available dimethylcarbamoyl chloride, commercially available diethylcarbamoyl chloride, and the like.

In the reaction, the compound (AA-7) is usually used in the proportion within a range of 0.5 to 5 mols, and the base is usually used in the proportion within a range of 0.5 to 5 mols, based on 1 mol of the compound (AA-6).

The reaction temperature of the reaction is usually within a range of −90 to 150° C. The reaction time of the reaction is usually within a range of 0.1 to 24 hours.

After completion of the reaction, the compound (AA-5) can be isolated by performing post-treatment operations such as extraction of the reaction mixture with an organic solvent, and drying and concentration of the organic layer. The isolated compound (AA-5) can also be purified by chromatography, recrystallization, and the like.

Although a form used for the present compound may be the present compound as itself, the present compound is usually used after mixing with solid carriers, liquid carriers, surfactants, and the like, and optionally adding auxiliary agents for formulation, such as stickers, dispersers, and stabilizers to thereby formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexanone, and kerosene), esters (for example, ethyl acetate and butyl acetate), nitriles (for example, acetonitrile and isobutyronitrile), ethers (for example, 1,4-dioxane and diisopropylether), acid amides (for example, dimethylformamide and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyoxyethylene glycol ethers, polyhydric alcohol esters, and sugar alcohol derivatives.

Examples of other auxiliary agents for formulation include stickers and dispersers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof, and the like.

The method for applying the present control agent is not particularly limited, as long as the applying form is a form by which the present control agent can be applied substantially, and includes, for example, an application to plants such as a foliage application; an application to area for cultivating plants such as a submerged treatment; and an application to seeds such as seed disinfection.

The present control agent may be used as a mixture with various oils, such as mineral oils or vegetable oils, or surfactants. Specific examples of oils or surfactants, which can be used as a mixture with various oils or surfactants include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSprayN (registered trademark), BANOLE (registered trademark), and the like.

The present compound can also be used as a mixture with other fungicides, insecticides, acaricides, nematicides, and plant growth regulators, or simultaneously therewith.

The application dose of the present control agent varies depending on weather conditions, dosage forms, timing of application, methods of application, areas to be applied, target diseases, target plants, and the like, and the amount of the present compound in the present control agent is usually within a range of 1 to 500 g, and preferably 2 to 200 g, per 1,000 m$^2$ of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound in the present control agent is usually within a range of 0.001 to 100 g, and preferably 0.01 to 50 g, per 1 kg of the seeds.

Also, in another embodiment, for example, the present compound or the present control agent can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, or administration via injection subcutaneously, intramuscularly, or intravenously. Examples of a method of the external administration include transdermal administration. Also, the present compound can be ingested to a livestock animal so as to exterminate sanitary insects which occur in the excrement of the animal.

When the present compound or the present control agent is applied to the animals such as the livestock animal and pets on which pests are parasitic, the dose varies depending on the administration method etc., and it is desirable to administer the present compound so that a dose of the active ingredient (present compound) is generally within a range of 0.1 mg to 2,000 mg, and preferably 0.5 mg to 1,000 mg, per 1 kg of body weight of the animal.

The present compound or the present control agent can be used as an agent for controlling plant diseases in agricultural lands such as fields, paddy fields, lawns, and orchards. The present compound can control diseases occurred in the agricultural lands for cultivating the following plants.

Crops: corn, rice, wheat, barley, rye, oat, sorghum, cotton, soybean, peanut, buckwheat, beet, rapeseed, sunflower, sugar cane, tobacco, and the like; Vegetables: solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), umbelliferous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, and the like; Flowers; Ornamental foliage plants;

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, persimmon, olive, loquat, banana, coffee, date palm, coconuts, and the like;

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus* cuspidate); and the like.

Lawn: lawn grasses (zoysiagrass, Korean lawn grass, etc.), Bermuda glasses (*cynodon dactylon*, etc.), bentgrasses (redtop grass, creeping bentgrass, colonial bentgrass, etc.), bluegrasses (Kentucky bluegrass, rough bluegrass, etc.), fescue grasses (tall fescue, chewings fescue, creeping red fescue, etc.), perennial ryegrasses (Italian ryegrass, perennial flax, etc.), orchard grass, timothy, etc.

The above-mentioned plants include genetically modified crops.

The pests which can be controlled by the present compound include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium graminearum, F. avenaceum, F. culmorum, Microdochium nivale*), rust (*Puccinia striiformis, P. graminis, P. recondita*), snow mould (*Micronectriella nivale*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), damping-off by Rhizoctonia (*Rhizoctonia solani*), and take-all disease (*Gaeumannomyces graminis*); Barley diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia leaf spot (*Ramularia collo-cygni*), and damping-off by Rhizoctonia (*Rhizoctonia solani*);

Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum graminicola*), gray leaf spot (*Cercospora zeae-maydis*), eyespot (*Kabatiella zeae*), and *phaeosphaeria* leaf spot (*Phaeosphaeria maydis*); Cotton diseases: anthracnose (*Colletotrichum gossypii*), grey mildew (*Ramularia areola*), and *alternaria* leaf spot (*Alternaria macrospora, A. gossypii*); Coffee diseases: rust (*Hemileia vastatrix*); Rape seed diseases: sclerotinia rot (*Sclerotinia sclerotiorum*), black spot (*Alternaria brassicae*), and black leg (*Phoma lingam*); Citrus diseases: melanose (*Diaporthe citri*), scab (*Elsinoe fawcetti*), and fruit rot (*Penicillium digitatum, P. italicum*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Glomerella cingulata*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), phytophthora rot (*Phytophthora* sp.), and damping-off (*Pythium* sp.);

Tomato diseases: early blight (*Alternaria solani*), leaf mold (*Cladosporium fulvum*), leaf mold (*Pseudocercospora fuligena*), and late blight (*Phytophthora infestans*); Eggplant diseases: brown spot (*Phomopsis vexans*) and powdery mildew (*Erysiphe cichoracearum*); Cruciferous vegetables diseases: alternaria leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), sphaceloma scad (*Elsinoe glycines*), pod and stem blight (*Diaporthe*

*phaseolorum* var. *sojae*), rust (*Phakopsora pachyrhizi*), target spot (*Corynespora cassiicola*), anthracnose (*Colletotrichum glycines, C. truncatum*), Rhizoctonia aerial blight (*Rhizoctonia solani*), septoria brown spot (*Septoria glycines*), and frog eye leaf spot (*Cercospora sojina*); Kidney bean diseases: anthracnose (*Colletotrichum lindemuthianum*); Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), and verticillium wilt (*Verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Sugar beet diseases: cercospora leaf spot (*Cercospora beticola*), leaf blight (*Thanatephorus cucumeris*), root rot (*Thanatephorus cucumeris*), and aphanomyces root rot (*Aphanomyces cochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: botrytis leaf blight (*Botrytis cinerea, B. byssoidea, B. squamosa*), gray-mold neck rot (*Botrytis alli*), and small sclerotial rot (*Botrytis squamosa*); various crops diseases: gray mold (*Botrytis cinerea*) and sclerotinia rot (*Sclerotinia sclerotiorum*); Japanese radish diseases: alternaria leaf spot (*Alternaria brassicicola*); Turfgrass diseases: dollar spot (*Sclerotinia homoeocarpa*) and brown patch and large patch (*Rhizoctonia solani*); and Banana diseases: Sigatoka disease (*Mycosphaerella fijiensis, Mycosphaerella musicola*).

Hemiptera: planthoppers (*Delphacidae*) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (Myzuspersicae), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), and tarnished plant bug (*Lygus lineolaris*); whiteflies (Aleyrodidae) such as greenhouse whitefly (*Trialeurodes vaporariorum*) and silverleaf whitefly (*Bemisia argentifolii*); scales (Coccidae) such as California red scale (*Aonidiella aurantii*), San Jose scale (*Comstockaspis perniciosa*), citrus north scale (*Unaspis citri*), red wax scale (*Ceroplastes rubens*), and cottony cushion scale (*Icerya purchasi*); lace bugs (Tingidae); jumping plant lice (Homoptera, Psylloidea); and bed bugs (*Cimex lectularius*).

Lepidoptera: pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* sp.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); codling moths (Carposimidae) such as peach fruit moth (*Carposina niponensis*); lyonetiid moths (Lyonetiidae) such as *Lyonetia* spp.; tussock moths (Lymantriidae) such as *Lymantria* spp. and *Euproctis* spp.; yponomeutid moths (Yponomeutidae) such as diamondback (*Plutellaxylostella*); gelechildmoths (Gelechiidae) such as pink bollworm (*Pectinophora gossypiella*) and potato tubeworm (*Phthorimaea operculella*); tiger moths and allies (Arctiidae) such as fall webworm (*Hyphantria cunea*); and tineid moths (Tineidae) such as casemaking clothes moth (*Tinea translucens*), and webbing clothes moth (*Tineola bisselliella*).

Thysanoptera: yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), and tobacco thrips (*Frankliniella fusca*).

Diptera: houseflies (*Musca domestica*), common mosquito (*Culex pipiens pallens*), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Mediterranean fruit fly (*Ceratitis capitata*), and legume leafminer (*Liriomyza trifolii*).

Coleoptera: twenty-eight-spotted ladybirds (*Epilachna vigintioctopunctata*), cucurbit leaf beetle (*Aulacophora femoralis*), yellow striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*).

Orthoptera: asiatic locusts (*Locusta migratoria*), African mole cricket (*Gryllotalpa africana*), rice grasshopper (*Oxya yezoensis*), and rice grasshopper (*Oxya japonica*).

Hymenoptera: cabbage sawflies (*Athalia rosae*), leaf-cutting ant (*Acromyrmex* spp.), and fire ant (*Solenopsis* spp.).

Nematodes: white-tip nematode (*Aphelenchoides besseyi*), strawberry bud nematode (*Nothotylenchus acris*), soybean cyst nematode (*Heterodera glycines*), southern root-knot nematode (*Meloidogyne incognita*), cobb's root-lesion nematode (*Pratylenchus penetrans*), and false root-knot nematode (*Nacobbus aberrans*).

Blattariae: German cockroach (*Blattella germanica*), smoky-brown cockroach (*Periplaneta fuliginosa*), American cockroach (*Periplaneta americana*), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus citri*), and *Oligonychus* spp.); Eriophyidae (for example, pink citrus rust mite (*Aculops pelekassi*)); Tarsonemidae (for example, broad mite (*Polyphagotarsonemus latus*)); Tenuipalpidae; Tuckerellidae; Tuckerellidae Acaridae (for example, common grain mite (*Tyrophagus putrescentiae*)); Pyroglyphidae (for example, Americal house dust mite (*Dermatophagoides farinae*) and house dust mite (*Dermatophagoides pteronyssinus*)); Cheyletidae (for example, cheyletid mite (*Cheyletus eruditus*), *Cheyletus malaccensis*, and *Cheyletus moorei*; and Dermanyssidae.

The formulation comprising the present compound can be used in the field relating to a treatment of livestock diseases or livestock industry, and can exterminate the living things or parasites which are parasitic on the inside and/or the outside of vertebrates such as human being, cow, sheep, goat, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *Dermacentor* spp., *Ornithodoros* spp. (for example, *Ornithodoros moubata*), red mite (*Dermanyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Aedes* spp. (for example, Asian tiger mosquito (*Aedes albopictus*)), *Anopheles* spp., *Culex* spp., *Culicoides* spp., *Musca* spp., *Hypoderma* spp., Gasterophilus spp., *Haematobia* spp., *Tabanus* spp., *Simulium* spp., *Triatoma* spp., lice (Phthiraptera) (for example, *Damalinia* spp.), *Linognathus* spp., *Haematopinus* spp., *Ctenocephalides* spp. (for example, cat flea (*Ctenocephalides felis*)) *Xenopsylla* spp., Pharaoh's ant (*Monomorium pharaonis*) and nematodes [for example, hairworm (for example, *Nippostrongylus brasiliensis*, *Trichostrongylus axei*, *Trichostrongylus colubriformis*), *Trichinella* spp. (for example, *Trichinella spiralis*), barber pole worm (*Haemonchus contortus*), *Nematodirus* spp. (for example, *Nematodirus* battus), *Ostertagia circumcincta*, *Cooperia* spp., *Hymenolepis nana*, and the like.

The present control agent containing at least one selected from the group consisting of known fungicides, insecticide, acaricides, nematicides, and plant growth regulators may be directly applied to a plant body to be protected from pests, or may be applied to soil for fix planting of the plant body, and seeds.

At least one selected from the group consisting of known fungicides, insecticide, acaricides, nematicides, and plant growth regulators may be applied to the plant body, simultaneously or separately, when using together with the present control agent. When applying separately, an application date may be different and a different dosage form may be used.

It is possible to combine an application of the present control agent to seeds of the plant with an application of at least one selected from the group consisting of known fungicides, insecticide, acaricides, nematicides, and plant growth regulators to the plant, or soil for fix planting of the plant. It is also possible to combine an application of at least one selected from the group consisting of known fungicides, insecticide, acaricides, nematicides, and plant growth regulators to seeds of the plant with an application of the present control agent to the plant, or soil for fix planting of the plant. An application to the plant, or soil for fix planting of the plant may be performed before, on, or after fix planting.

This application method is preferably applied to cultivation of corn, wheat, and rice.

It is possible to combine an application of the present control agent to a plant body, or soil on which the plant body is cultivated or to be cultivated (for example, soil of paddy fields, crop fields, orchards, or non-cultivated lands) with an application of at least one selected from known herbicides to the soil. The pest control agent of the present invention and herbicides can be applied simultaneously or separately. When applying separately, the application may be performed on the same or different day.

Examples of the herbicide, which can be used together with the present control agent, include glyphosate, salts of glyphosate, glufosinate, salts of glyphosate, 2,4-D, salts of 2,4-D, dicamba, salts of dicamba, and flumioxazin.

EXAMPLES

The present invention will be described in more detail below by way of Production Examples, Formulation Examples, and Test Examples, but the present invention is not limited to these Examples.

First, Production Examples will be described.

Production Example 1

A mixture of 0.30 g of X2 mentioned in Reference Production Example 3, 0.12 g of 2-methylphenylboronic acid, 0.057 g of a [1,1'-bis(diphenylphosphino)ferrocene] palladium(II) dichloride dichloromethane adduct, 0.22 g of potassium acetate, and 5 mL of 1,2-dimethoxyethane was stirred at 80° C. for 5 hours. After cooling to room temperature, the reaction mixture was filtered and the filtrate was concentrated. The residue thus obtained was subjected to silica gel column chromatography to obtain 0.27 g of 1-{2-[4-(2-methyl-phenyl)-2-methylphenylthiomethyl]-3-methylphenyl}-4-methyl-1,4-dihydrotetrazol-5-one (hereinafter referred to as the present compound 1).

Present Compound 1

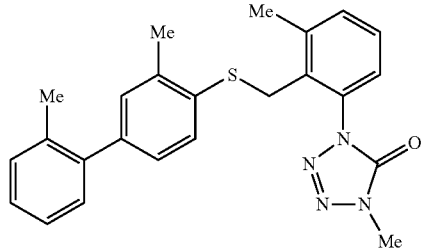 [SMILES: Cc1cc(-c2ccccc2C)ccc1SCc1c(C)cccc1-n1nnn(C)c1=O]

$^1$H-NMR (CDCl$_3$) δ: 7.32-7.32 (2H, m), 7.24-7.20 (6H, m), 7.11 (1H, d, J=1.8 Hz), 7.06 (1H, dd, J=7.7, 1.8 Hz), 4.15 (2H, s), 3.65 (3H, s), 2.43 (3H, s), 2.29 (3H, s), 2.27 (3H, s).

Production Example 2

Using Z1 mentioned in Reference Production Example 5 in place of X2 and using phenylboronic acid in place of 2-methylphenylboronic acid in Production Example 1, the same reaction was performed to obtain 1-{2-[4-phenyl-phenylthiomethyl]-3-methylphenyl}-4-methyl-1,4-dihydrotetrazol-5-one (hereinafter referred to as the present compound 2).

Present Compound 2

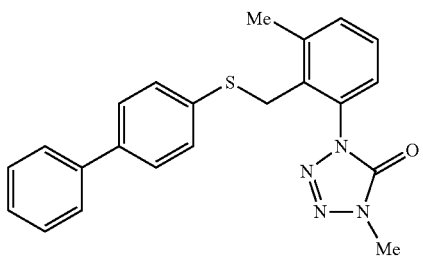 [SMILES: Cc1cccc(-n2nnn(C)c2=O)c1CSc1ccc(-c2ccccc2)cc1]

¹H-NMR (CDCl₃) δ: 7.59-7.55 (1H, m), 7.48-7.42 (2H, m), 7.38-7.34 (1H, m), 7.33-7.30 (6H, m), 7.22-7.17 (1H, m), 7.13-7.09 (1H, m), 4.22 (2H, s), 3.60 (3H, s), 2.40 (3H, s).

Production Example 3

Using Z1 mentioned in Reference Production Example 5 in place of X2 in Production Example 1, the same reaction was performed to obtain 1-{2-[4-(2-methyl-phenyl)-phenylthiomethyl]-3-methylphenyl}-4-methyl-1,4-dihydrotetrazol-5-one (hereinafter referred to as the present compound 3).

Present Compound 3

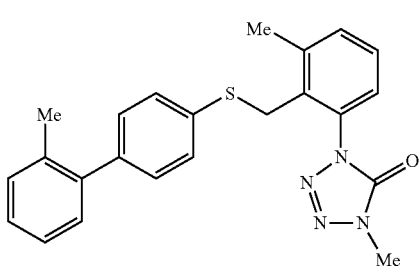 [SMILES: Cc1ccccc1-c1ccc(SCc2c(C)cccc2-n2nnn(C)c2=O)cc1]

¹H-NMR (CDCl₃) δ: 7.31-7.29 (3H, m), 7.28-7.23 (4H, m), 7.22-7.17 (4H, m), 4.21 (2H, s), 3.66 (3H, s), 2.39 (3H, s), 2.26 (3H, s).

Production Example 4

Using Z1 mentioned in Reference Production Example 5 in place of X2 in Production Example 1 and using 4-methylphenylboronic acid in place of 2-methylphenylboronic acid, the same reaction was performed to obtain 1-{2-[4-(4-methyl-phenyl)-phenylthiomethyl]-3-methylphenyl}-4-methyl-1,4-dihydrotetrazol-5-one (hereinafter referred to as the present compound 4).

Present Compound 4

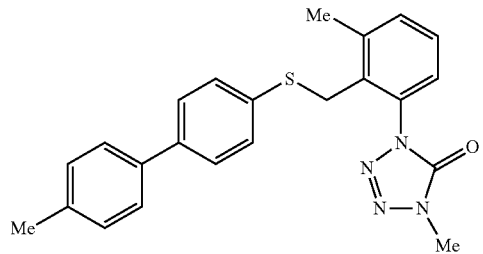 [SMILES: Cc1ccc(-c2ccc(SCc3c(C)cccc3-n3nnn(C)c3=O)cc2)cc1]

¹H-NMR (CDCl₃) δ: 7.47-7.44 (2H, m), 7.35-7.33 (2H, m), 7.31-7.29 (3H, m), 7.24 (1H, s), 7.21-7.18 (1H, m), 7.11-7.10 (2H, m), 4.21 (2H, s), 3.59 (3H, s), 2.39 (6H, s).

Production Example 5

Using Z1 mentioned in Reference Production Example 5 in place of X2 and using 3-chlorophenylboronic acid in place of 2-methylphenylboronic acid in Production Example 1, the same reaction was performed to obtain 1-{2-[4-(3-chloro-phenyl)-phenylthiomethyl]-3-methylphenyl}-4-methyl-1,4-dihydrotetrazol-5-one (hereinafter referred to as the present compound 5).

Present Compound 5

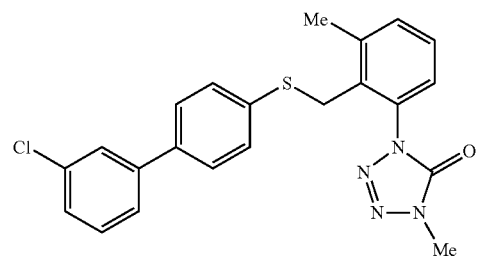 [SMILES: Cc1cccc(-n2nnn(C)c2=O)c1CSc1ccc(-c2cccc(Cl)c2)cc1]

¹H-NMR (CDCl₃) δ: 7.55 (1H, t, J=1.9 Hz), 7.45-7.42 (3H, m), 7.37 (1H, t, J=7.7 Hz), 7.33-7.30 (5H, m), 7.22-7.18 (1H, m), 4.22 (2H, s), 3.61 (3H, s), 2.40 (3H, s).

Production Example 6

Using Z1 mentioned in Reference Production Example 5 in place of X2 and using 4-methoxyphenylboronic acid in place of 2-methylphenylboronic acid in Production Example 1, the same reaction was performed to obtain 1-{2-[4-(4-methoxy-phenyl)-phenylthiomethyl]-3-methylphenyl}-4-methyl-1,4-dihydrotetrazol-5-one (hereinafter referred to as the present compound 6).

Present Compound 6

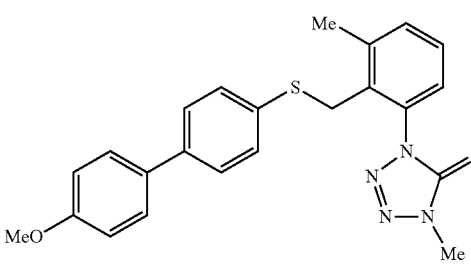

¹H-NMR (CDCl3) δ: 7.51 (2H, dt, J=9.4, 2.6 Hz), 7.42 (2H, dt, J=8.5, 2.2 Hz), 7.31-7.27 (4H, m), 7.22-7.17 (1H, m), 6.98 (2H, dt, J=9.4, 2.6 Hz), 4.21 (2H, s), 3.85 (3H, s), 3.59 (3H, s), 2.39 (3H, s).

Production Example 7

Using phenylboronic acid in place of 2-methylphenylboronic acid in Production Example 1, the same reaction was performed to obtain 1-{2-[4-phenyl-2-methyl-phenylthiomethyl]-3-methylphenyl}-4-methyl-1,4-dihydrotetrazol-5-one (hereinafter referred to as the present compound 7).

Present Compound 7

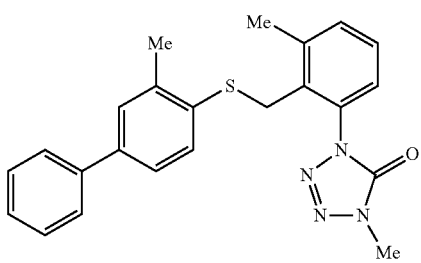 [SMILES: Cc1cc(-c2ccccc2)ccc1SCc1c(C)cccc1-n1nnn(C)c1=O]

¹H-NMR (CDCl₃) δ: 7.60-7.55 (2H, m), 7.47-7.41 (2H, m), 7.39-7.29 (6H, m), 7.22-7.17 (1H, m), 4.16 (2H, s), 3.59 (3H, s), 2.44 (3H, s), 2.32 (3H, s).

Production Example 8

Using 3-methyl phenylboronic acid in place of 2-methylphenylboronic acid in Production Example 1, the same reaction was performed to obtain 1-{2-[3-(3-methyl-phenyl)-2-methyl-phenylthiomethyl]-3-methylphenyl}-4-methyl-1,4-dihydrotetrazol-5-one (hereinafter referred to as the present compound 8).

Present Compound 8

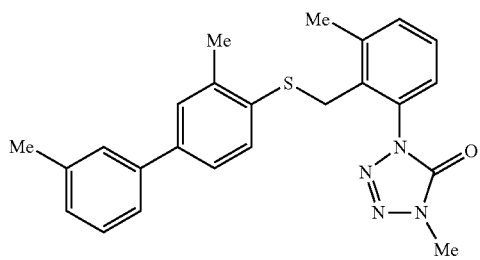 [SMILES: Cc1cccc(-c2ccc(SCc3c(C)cccc3-n3nnn(C)c3=O)c(C)c2)c1]

¹H-NMR (CDCl₃) δ: 7.39-7.35 (3H, m), 7.35-7.29 (5H, m), 7.21-7.19 (1H, m), 7.18-7.15 (1H, m), 4.16 (2H, s), 3.59 (3H, s), 2.43 (3H, s), 2.42 (3H, s), 2.31 (3H, s).

Production Example 9

Using 4-methylphenylboronic acid in place of 2-methylphenylboronic acid in Production Example 1, the same reaction was performed to obtain 1-{2-[3-(4-methyl-phenyl)-2-methyl-phenylthiomethyl]-3-methylphenyl}-4-methyl-1,4-dihydrotetrazol-5-one (hereinafter referred to as the present compound 9).

Present Compound 9

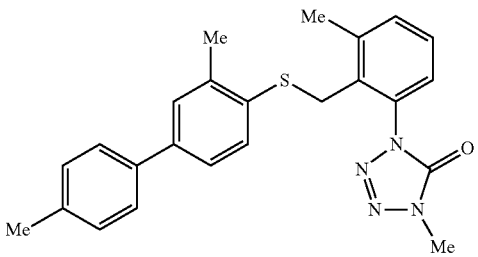 [SMILES: Cc1ccc(-c2ccc(SCc3c(C)cccc3-n3nnn(C)c3=O)c(C)c2)cc1]

¹H-NMR (CDCl₃) δ: 7.49-7.46 (2H, m), 7.37-7.36 (1H, m), 7.33-7.29 (4H, m), 7.27-7.25 (1H, m), 7.23 (1H, s), 7.21-7.18 (1H, m), 4.15 (2H, s), 3.58 (3H, s), 2.43 (3H, s), 2.39 (3H, s), 2.31 (3H, s).

Production Example 10

A mixture of 0.40 g of X1 mentioned in Reference Production Example 1, 0.11 g of 2-chloropyridine, 0.147 g of a [1,1'-bis(diphenylphosphino)ferrocene]palladium(II) dichloride dichloromethane adduct, 0.56 g of tripotassium phosphate, and 5 mL of 1,2-dimethoxyethane was stirred at 80° C. for 5 hours. After cooling to room temperature, the reaction mixture was filtered and the filtrate was concentrated. The residue thus obtained was subjected to silica gel column chromatography to obtain 0.27 g of 1-{2-[4-(pyridin-2-yl)-2-methylphenylthiomethyl]-3-methylphenyl}-4-methyl-1,4-dihydrotetrazol-5-one (hereinafter referred to as the present compound 10).

Present Compound 10

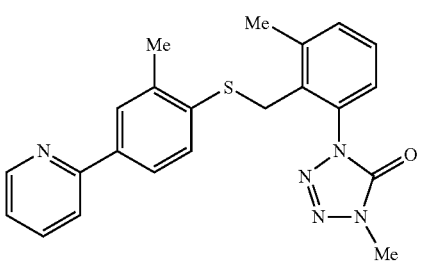 [SMILES: Cc1cc(-c2ccccn2)ccc1SCc1c(C)cccc1-n1nnn(C)c1=O]

¹H-NMR (CDCl₃) δ: 8.68 (1H, dq, J=4.8, 0.9 Hz), 7.82 (1H, d, J=1.6 Hz), 7.77-7.69 (3H, m), 7.34-7.29 (3H, m), 7.25-7.18 (2H, m), 4.18 (2H, s), 3.61 (3H, s), 2.43 (3H, s), 2.34 (3H, s).

Production Example 11

Using Y1 mentioned in Reference Production Example 2 in place of X1 in Production Example 10, the same reaction was performed to obtain 1-{2-[4-(pyridin-2-yl)-2,5-dimethyl phenylthiomethyl]-3-methylphenyl}-4-methyl-1,4-dihydrotetrazol-5-one (hereinafter referred to as the present compound 11).

Present Compound 11

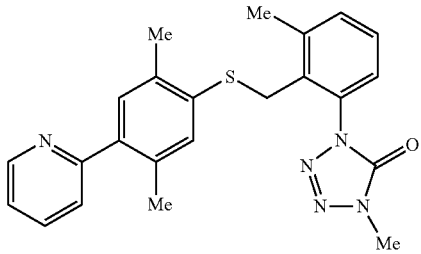 [SMILES: Cc1cc(-c2ccccn2)c(C)cc1SCc1c(C)cccc1-n1nnn(C)c1=O]

$^1$H-NMR (CDCl$_3$) δ: 8.69 (1H, dq, J=4.8, 0.9 Hz), 7.74 (1H, td, J=7.7, 1.8 Hz), 7.40 (1H, dt, J=7.9, 1.0 Hz), 7.34-7.31 (2H, m), 7.26-7.19 (3H, m), 7.13 (1H, s), 4.15 (2H, s), 3.65 (3H, s), 2.46 (3H, s), 2.30 (3H, s), 2.25 (3H, s).

With respect to the production of intermediates for the production of the above-mentioned present compounds, Reference Production Examples are shown below.

Reference Production Example 1

A mixture of 2 g of X2 mentioned in Reference Production Example 3, 0.74 g of a [1,1'-bis(diphenylphosphino)ferrocene]palladium(II) dichloride dichloromethane adduct, 2.2 g of potassium acetate, 2.1 g of bis(pinacolato)diboron, and 30 mL of dimethyl sulfoxide was stirred at 90° C. for 12 hours. After cooling to room temperature, a saturated saline solution was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 2.5 g of X1 shown below.

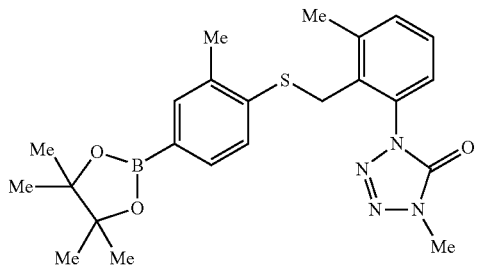 [SMILES: Cc1cc(B2OC(C)(C)C(C)(C)O2)ccc1SCc1c(C)cccc1-n1nnn(C)c1=O]

$^1$H-NMR (CDCl$_3$) δ: 7.56 (2H, d, J=6.3 Hz), 7.34-7.30 (2H, m), 7.22-7.19 (2H, m), 4.16 (2H, s), 3.63 (3H, s), 2.43 (3H, s), 2.24 (3H, s), 1.34 (12H, s).

Reference Production Example 2

Using Y2 mentioned in Reference Production Example 4 in place of X2 in Reference Production Example 1, the same reaction was performed to obtain Y1 shown below.

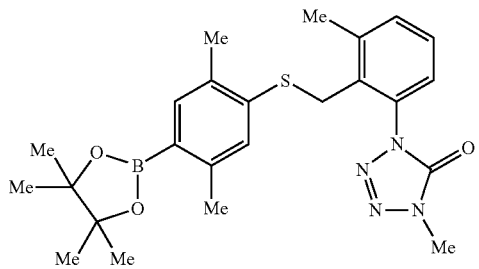 [SMILES: Cc1cc(B2OC(C)(C)C(C)(C)O2)c(C)cc1SCc1c(C)cccc1-n1nnn(C)c1=O]

$^1$H-NMR (CDCl$_3$) δ: 7.50 (1H, s), 7.34-7.31 (2H, m), 7.20 (1H, dd, J=6.5, 3.1 Hz), 7.00 (1H, s), 4.14 (2H, s), 3.63 (3H, s), 2.47 (3H, s), 2.44 (3H, s), 2.20 (3H, s), 1.33 (12H, s).

Reference Production Example 3

A mixture of 4 g of 1-(2-bromomethyl-3-methylphenyl)-4-methyl-1,4-dihydrotetrazol-5-one (produced in accordance with the method mentioned in WO 2013/162072 A), 4.1 g of 1A mentioned in Reference Production Example 6, 7.6 g of potassium carbonate, and 20 ml of acetonitrile was stirred at 80° C. for 7 hours. The reaction mixture was concentrated under reduced pressure. The residue thus obtained was subjected to silica gel column chromatography to obtain 6.42 g of X2 shown below.

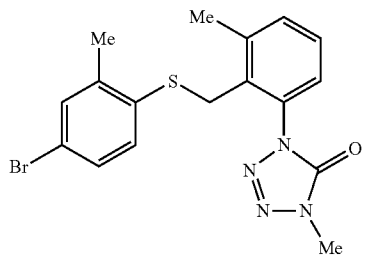 [SMILES: Cc1cc(Br)ccc1SCc1c(C)cccc1-n1nnn(C)c1=O]

$^1$H-NMR (CDCl$_3$) δ: 7.33-7.29 (3H, m), 7.22-7.18 (2H, m), 7.07 (1H, d, J=8.2 Hz), 4.10 (2H, s), 3.64 (3H, s), 2.39 (3H, s), 2.22 (3H, s).

Reference Production Example 4

Using 2A mentioned in Reference Production Example 7 in place of 1A in Reference Production Example 3, the same reaction was performed to obtain Y2 shown below.

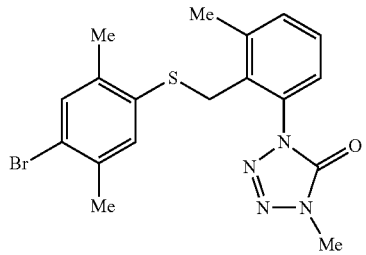 [SMILES: Cc1cc(SCc2c(C)cccc2-n2nnn(C)c2=O)c(C)cc1Br]

$^1$H-NMR (CDCl$_3$) δ: 7.32-7.30 (3H, m), 7.20-7.16 (1H, m), 7.05 (1H, s), 4.09 (2H, s), 3.63 (3H, s), 2.40 (3H, s), 2.29 (3H, s), 2.18 (3H, s).

Reference Production Example 5

Using commercially available 4-bromothiophenol in place of 1A in Reference Production Example 3, the same reaction was performed to obtain Z1 shown below.

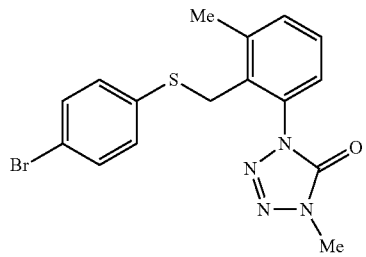 [SMILES: Cc1cccc(-n2nnn(C)c2=O)c1CSc1ccc(Br)cc1]

$^1$H-NMR (CDCl$_3$) δ: 7.36-7.33 (2H, m), 7.31-7.29 (2H, m), 7.21-7.19 (1H, m), 7.12-7.09 (2H, m), 4.16 (2H, s), 3.65 (3H, s), 2.35 (3H, s).

Reference Production Example 6

A mixture of 13 g of 1C mentioned in Reference Production Example 9 and 50 ml of diphenyl ether was stirred at 230° C. for 24 hours, and then the solution was subjected to silica gel column chromatography to obtain 10 g of 1B shown below.

A mixture of 10 g of 1B, 50 ml of an aqueous 20% sodium hydroxide solution, and 50 ml of isopropanol was stirred at 80° C. for 24 hours. To the reaction mixture, 10% hydrochloric acid was added and the mixture was extracted with chloroform. The organic layer was washed with water, dried over anhydrous magnesium sulfate, and then concentrated under reduced pressure. The residue thus obtained was subjected to silica gel column chromatography to obtain 8.2 g of 1A.

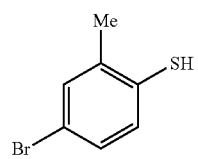

$^1$H-NMR (CDCl$_3$) δ: 7.30 (1H, d, J=2.1 Hz), 7.19 (1H, dd, J=8.2, 2.1 Hz), 7.13 (1H, d, J=8.2 Hz), 3.28 (1H, s), 2.30 (3H, s).

Reference Production Example 7

Using 2B mentioned in Reference Production Example 8 in place of 1B in Reference Production Example 6, the same reaction was performed to obtain 2A shown below.

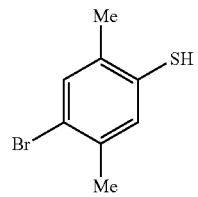

$^1$H-NMR (CDCl$_3$) δ: 7.32 (1H, s), 7.14 (1H, s), 3.24 (1H, s), 2.30 (3H, s), 2.26 (3H, s).

Reference Production Example 8

Using 2C mentioned in Reference Production Example 10 in place of 1C in Reference Production Example 6, the same reaction was performed to obtain 2B shown below.

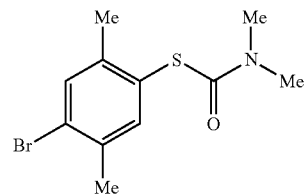 [SMILES: Cc1cc(SC(=O)N(C)C)c(C)cc1Br]

$^1$H-NMR (CDCl$_3$) δ: 7.47 (1H, s), 7.33 (1H, s), 3.12 (3H, br s), 3.01 (3H, br s), 2.34 (6H, s).

Reference Production Example 9

To a mixture of 10.3 g of commercially available 2-methyl-4-bromo-phenol and 100 ml of dimethylformamide, 2.64 g of 55% sodium hydride was added at 0° C., followed by stirring at room temperature for 0.5 hour, addition of 7.5 g of dimethylthiocarbamoyl chloride at 0° C., and further stirring at room temperature for 5 hours. To the reaction mixture, water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 13 g of 1C shown below.

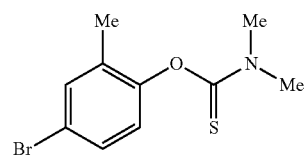 [SMILES: Cc1cc(Br)ccc1OC(=S)N(C)C]

$^1$H-NMR (CDCl$_3$) δ: 7.38 (1H, d, J=2.3 Hz), 7.33 (1H, dd, J=8.7, 2.3 Hz), 6.86 (1H, d, J=8.7 Hz), 3.46 (3H, s), 3.36 (3H, s), 2.17 (3H, s).

Reference Production Example 10

Using commercially available 2,5-dimethyl-4-bromophenol in place of 2-methyl-4-bromo-phenol in Reference Production Example 9, the same reaction was performed to obtain 2C shown below.

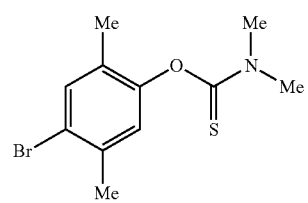 [SMILES: Cc1cc(OC(=S)N(C)C)c(C)cc1Br]

$^1$H-NMR (CDCl$_3$) δ: 7.40 (1H, s), 6.86 (1H, s), 3.46 (3H, s), 3.35 (3H, s), 2.35 (3H, s), 2.14 (3H, s).

In accordance with the process mentioned above, it is possible to obtain compounds HA1001-1 to IO1012-438. The above-mentioned compounds HA1001-1 to IO1012-

438 (hereinafter referred to as the compound A) are aromatic compounds shown below [wherein A represents any one of the below-mentioned substituent numbers 1 to 438)]. In the following [substituent number; A], F represents fluoro, Cl represents chloro, Br represents bromo, CN represents cyano, Me represents methyl, Et represents ethyl, $CF_3$ represents trifluoromethyl, $CHF_2$ represents difluoromethyl, OMe represents methoxy, and OEt represents ethoxy.

1aa or 1bb in A represents the following structure:

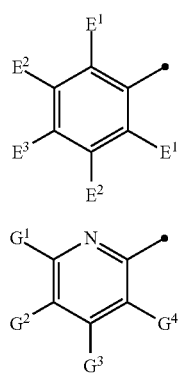

For example, HA1001-100 represents a compound in which A is a group represented by the substituent number 100 in formula (HA1001), and the substituent number 100 means a compound in which A is 1bb mentioned above, G1 is a methyl group, C2 is a cyano group, and G3 and G4 are hydrogen atoms, and specifically means a compound represented by the following formula.

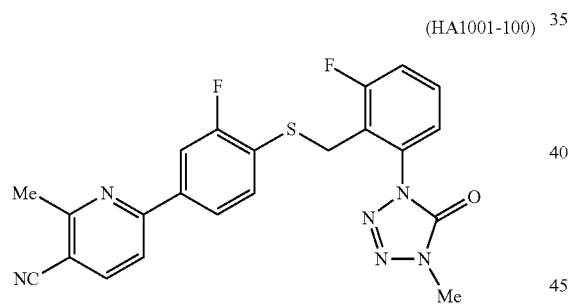
(HA1001-100)

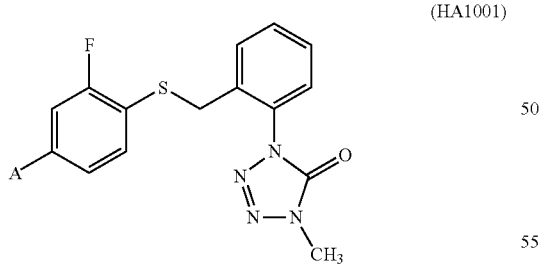
(HA1001)

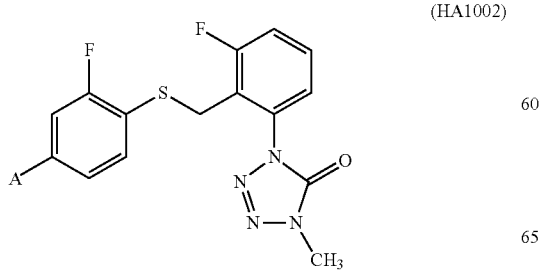
(HA1002)

-continued

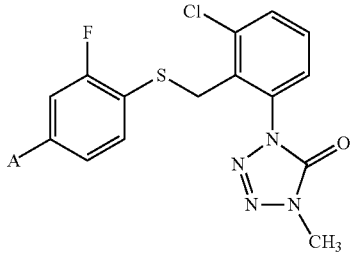
(HA1003)

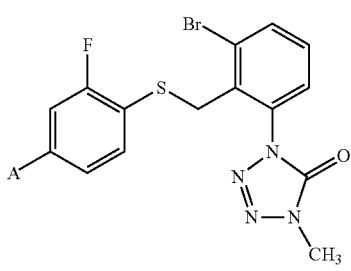
(HA1004)

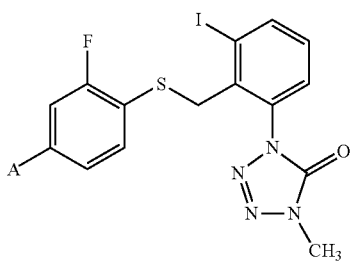
(HA1005)

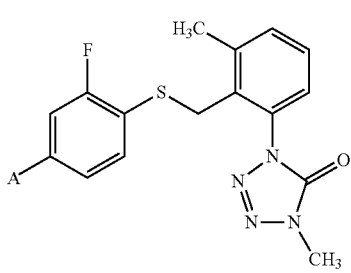
(HA1006)

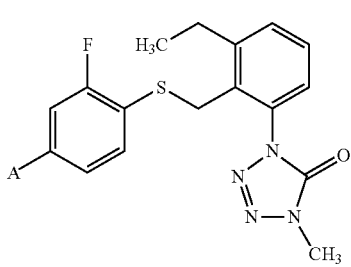
(HA1007)

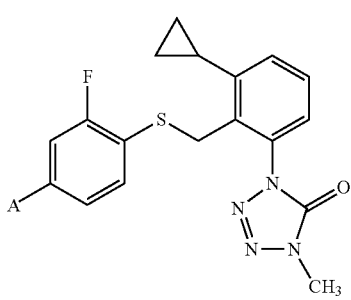
(HA1008)

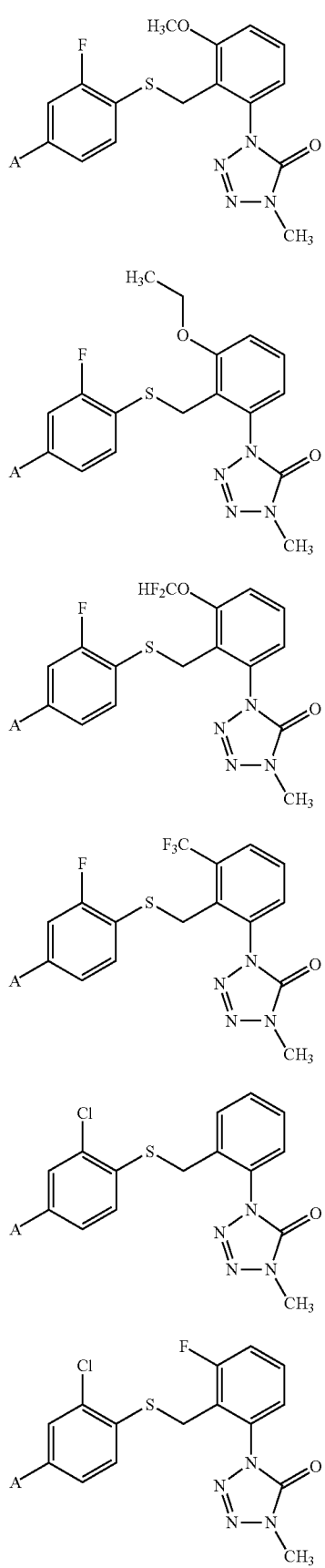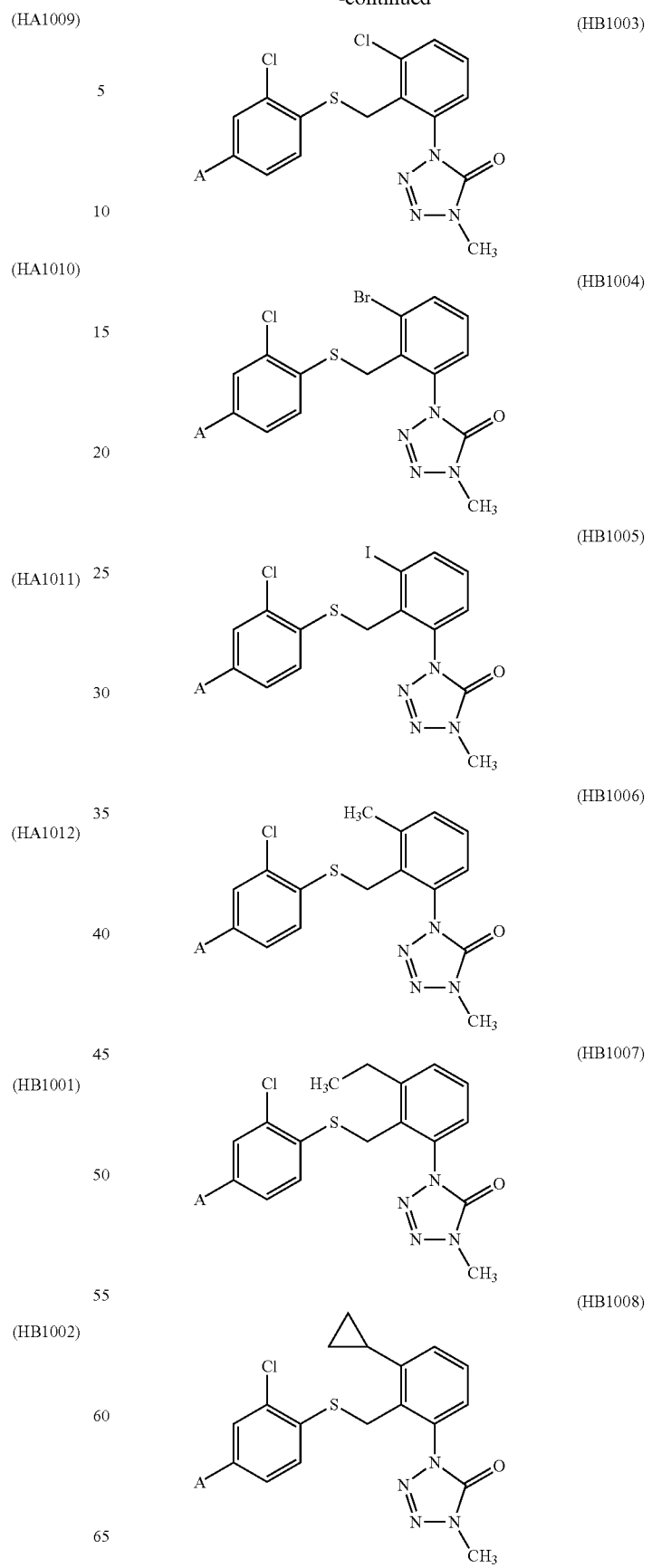

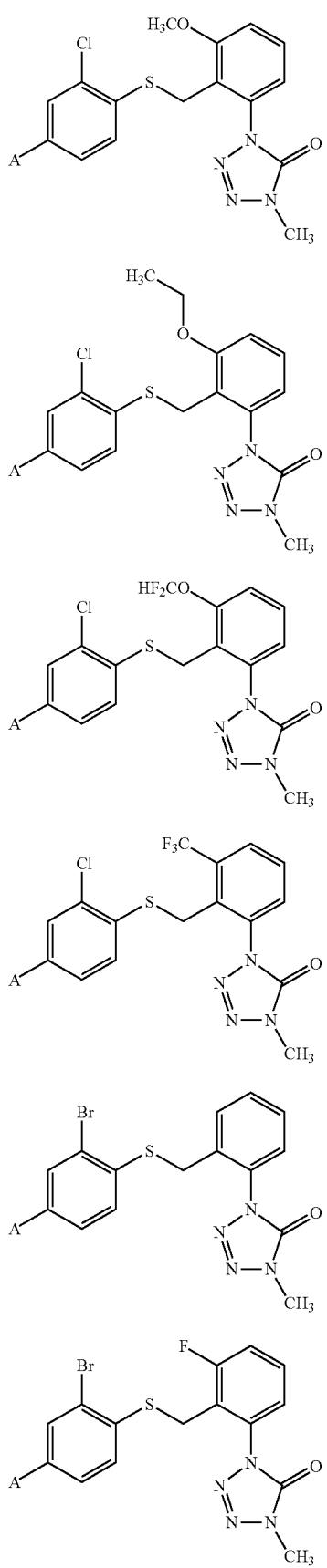
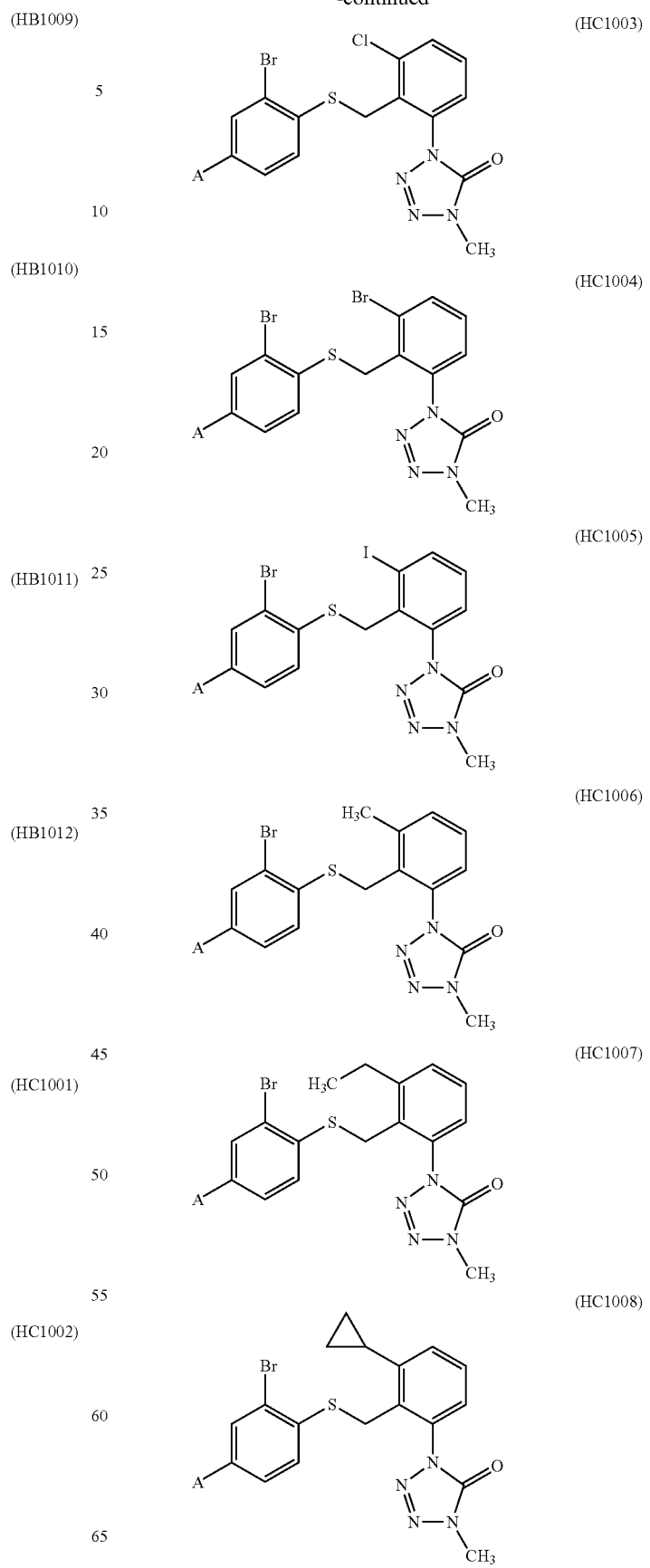

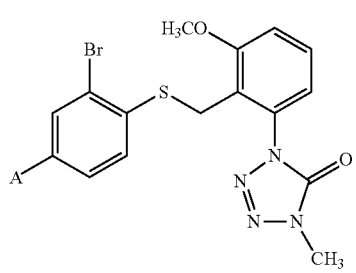
(HC1009)
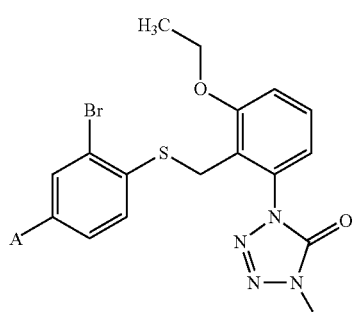
(HC1010)
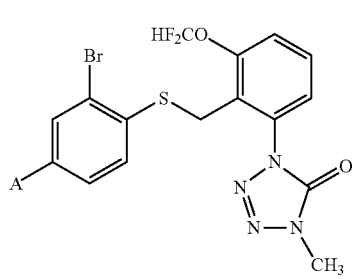
(HC1011)
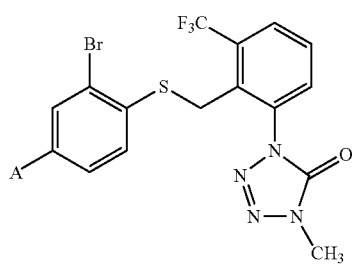
(HC1012)
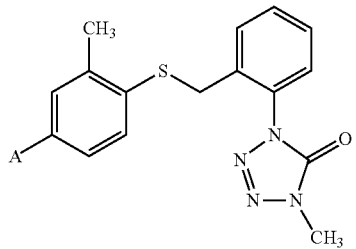
(HD1001)
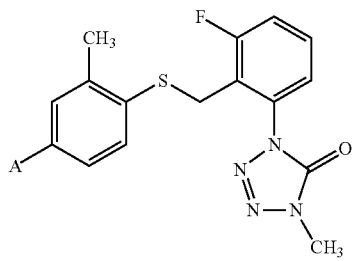
(HD1002)
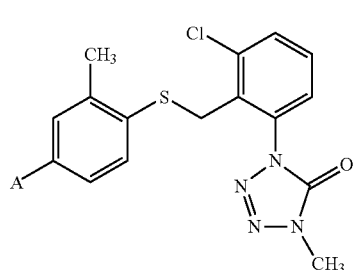
(HD1003)
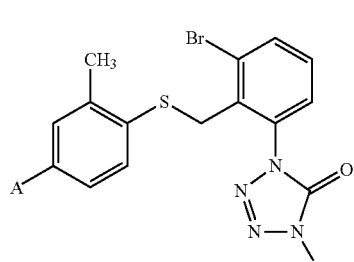
(HD1004)
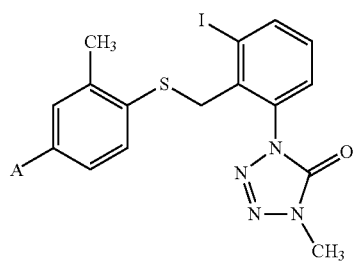
(HD1005)
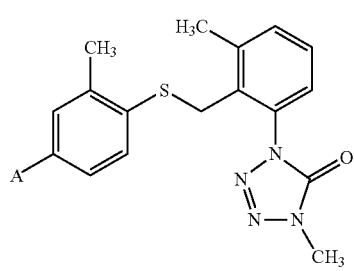
(HD1006)
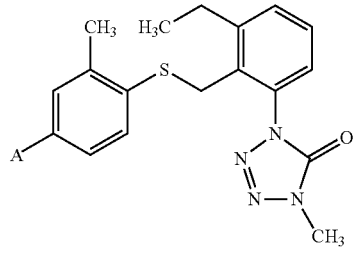
(HD1007)
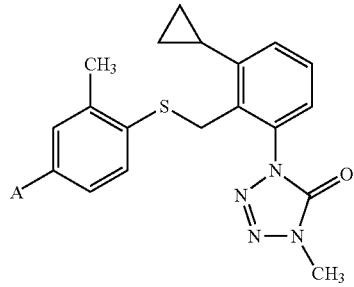
(HD1008)

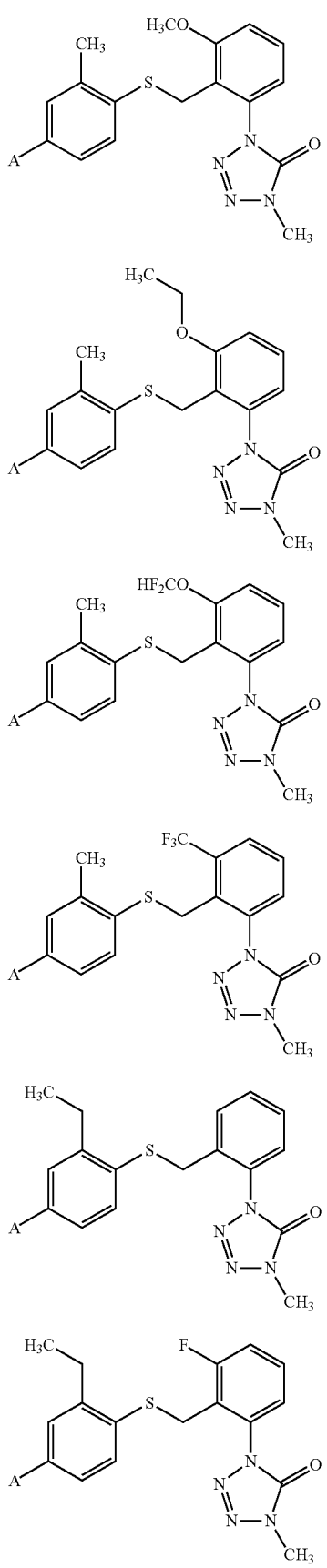
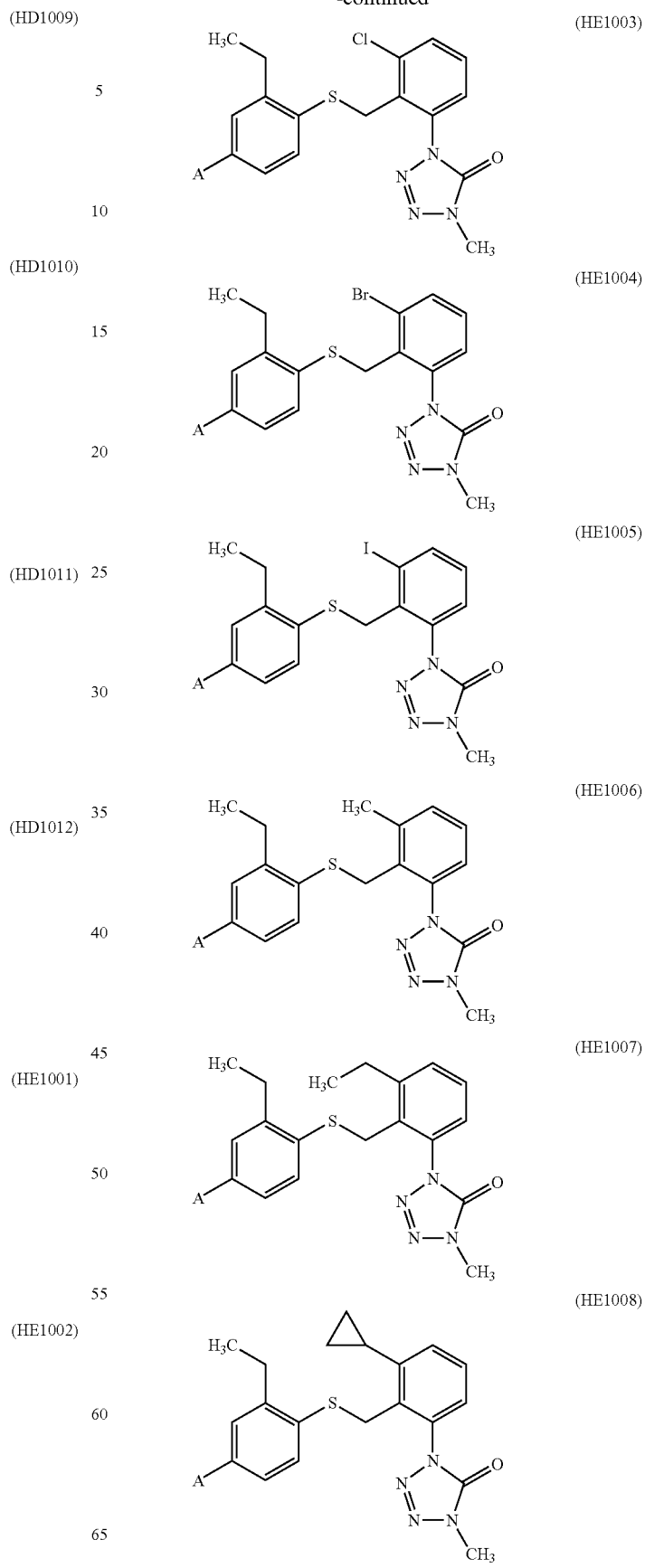

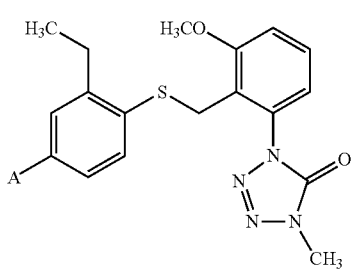
(HE1009)
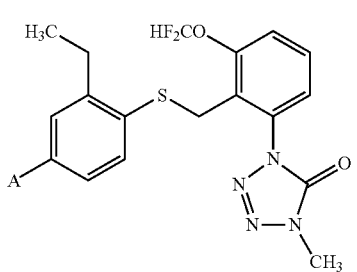
(HE1010)
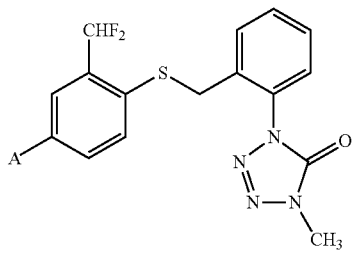
(HE1011)
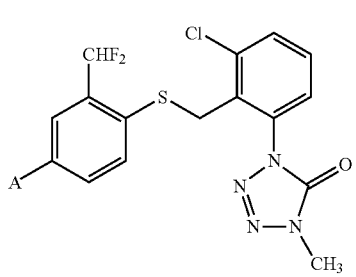
(HF1003)
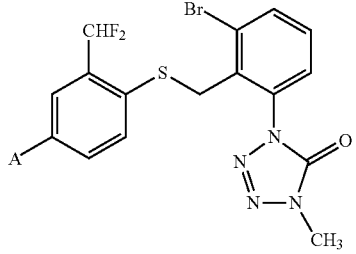
(HF1004)
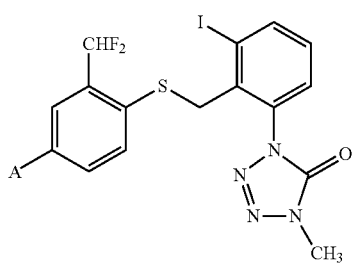
(HF1005)
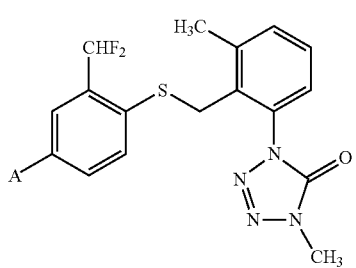
(HF1006)
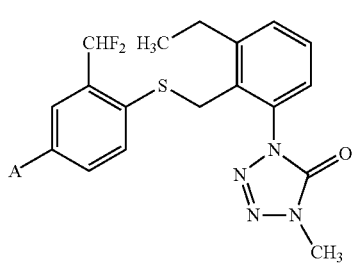
(HF1007)
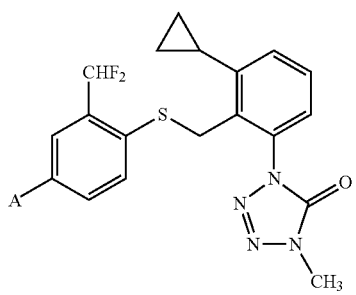
(HF1008)
(HE1012)
(HF1001)
(HF1002)

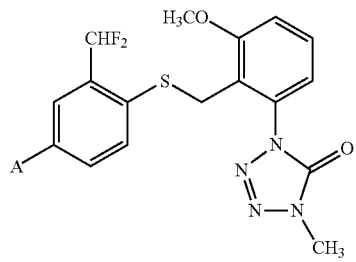
(HF1009)
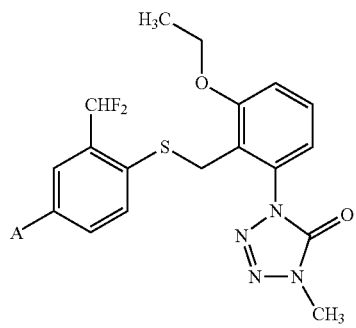
(HF1010)
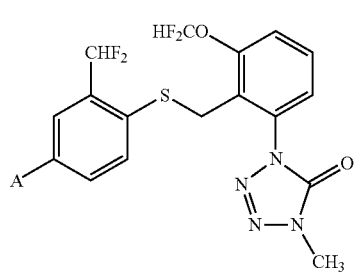
(HF1011)
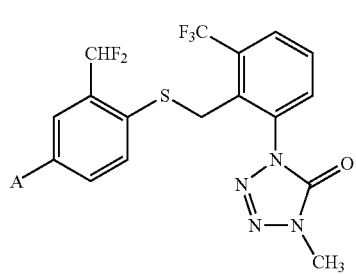
(HF1012)
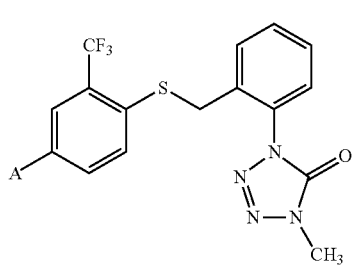
(HG1001)
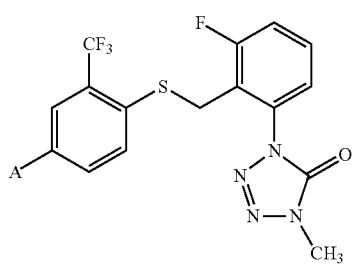
(HG1002)
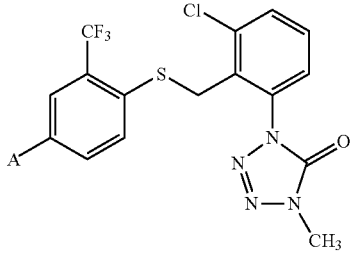
(HG1003)
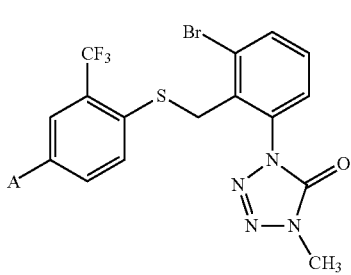
(HG1004)
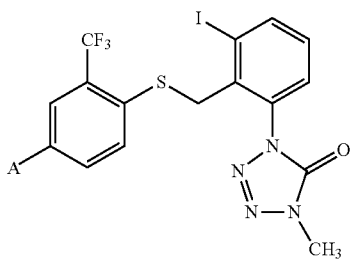
(HG1005)
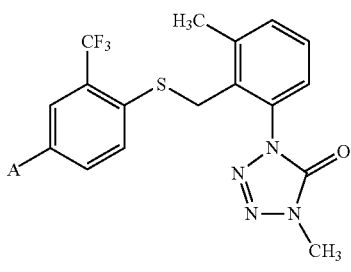
(HG1006)
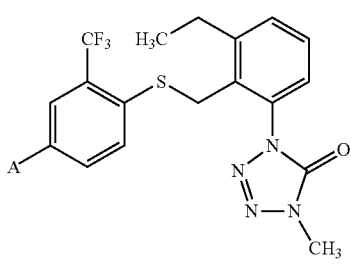
(HG1007)
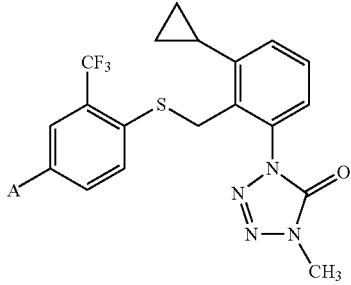
(HG1008)

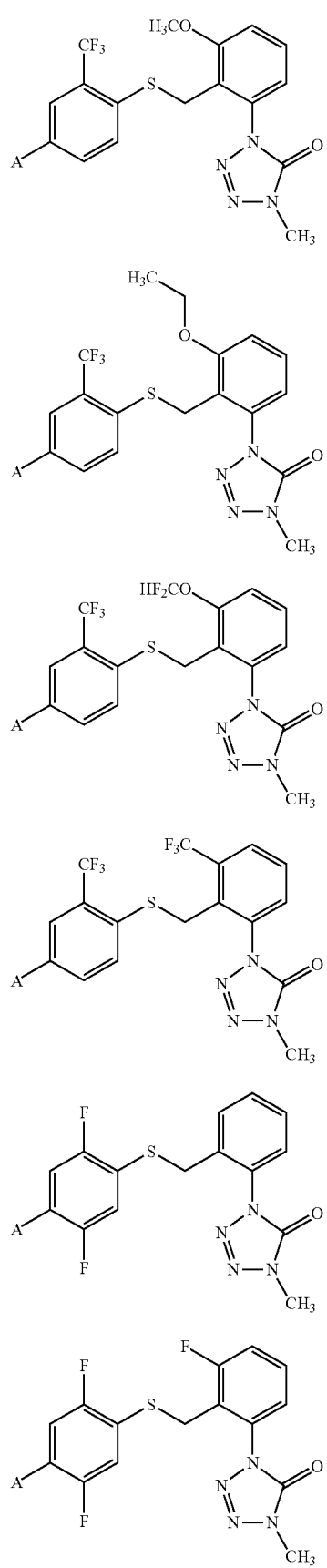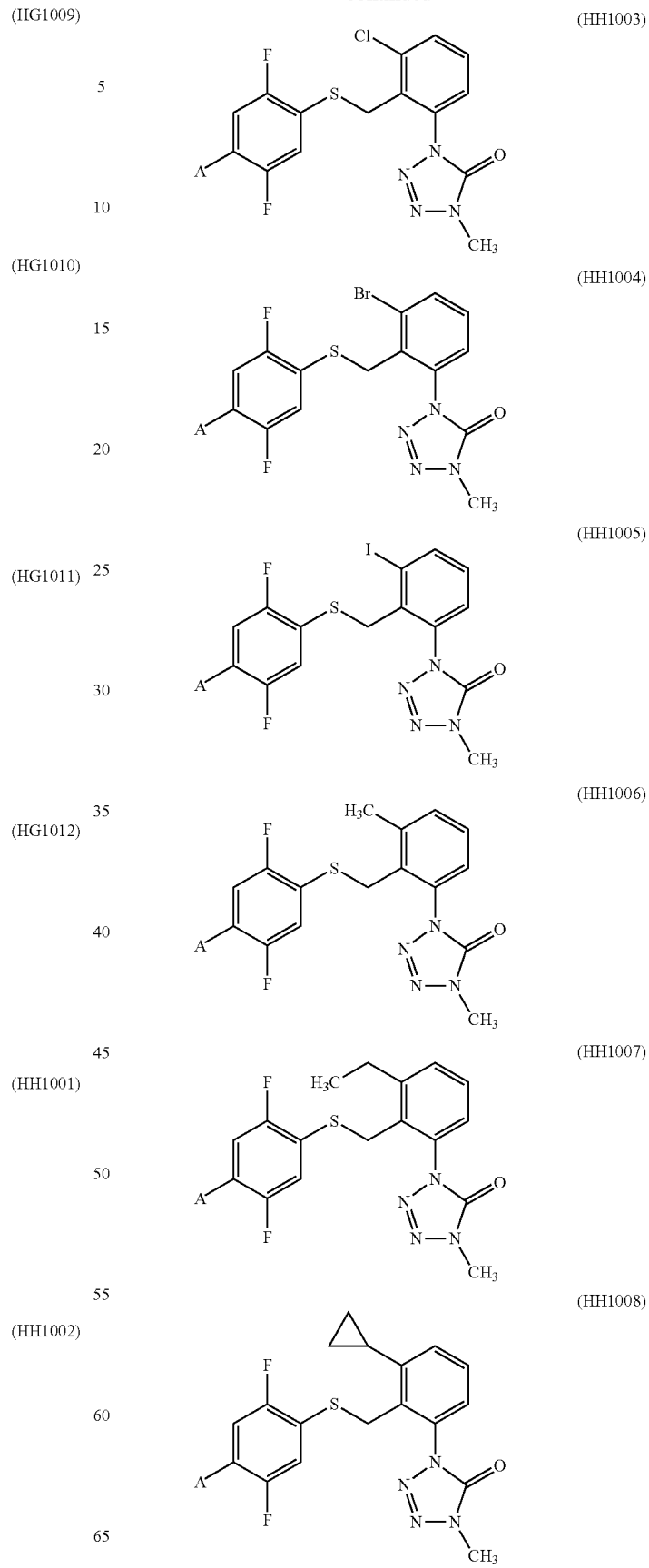

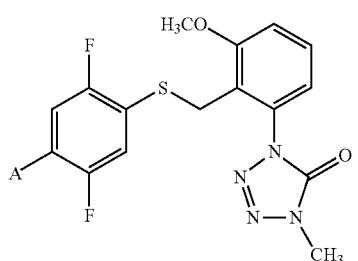
(HH1009)
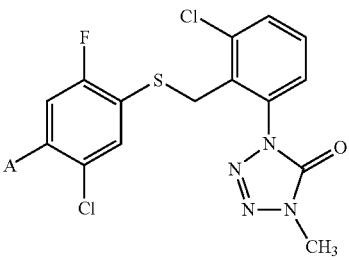
(HI1003)
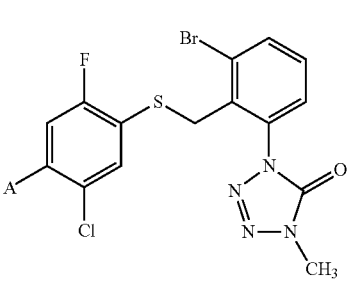
(HI1004)
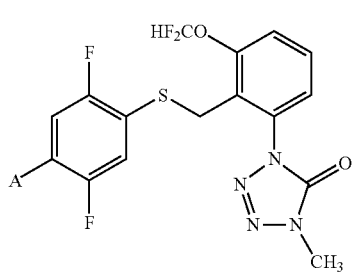
(HH1010)
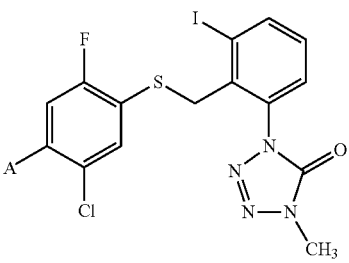
(HI1005)
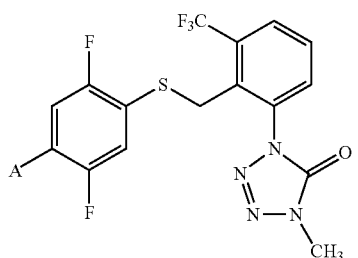
(HH1011)
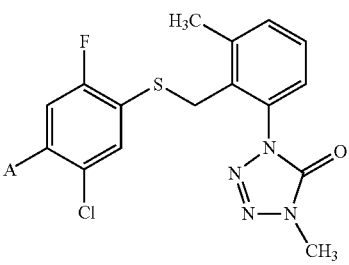
(HI1006)
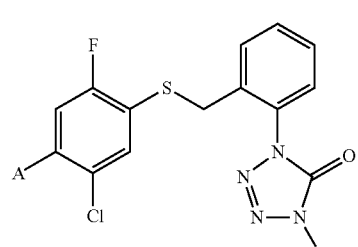
(HH1012)
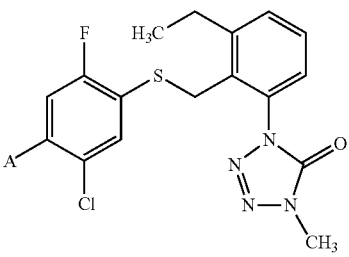
(HI1007)
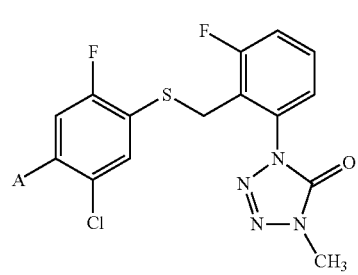
(HI1001)
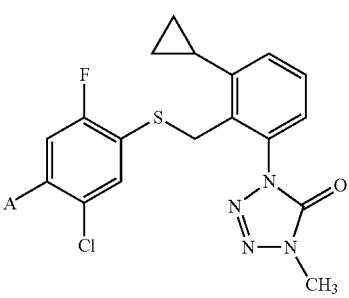
(HI1008)
(HI1002)

(HI1009)
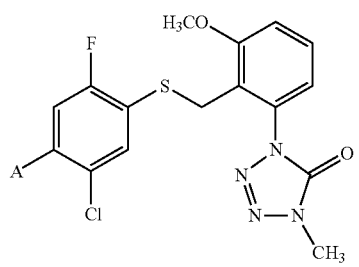
(HI1010)
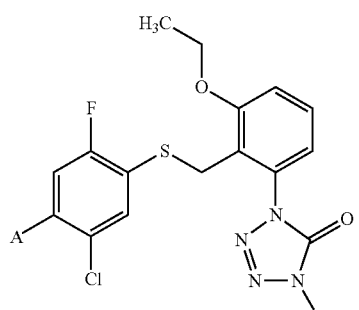
(HI1011)
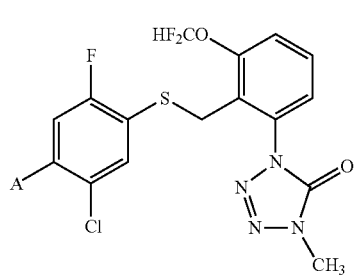
(HI1012)
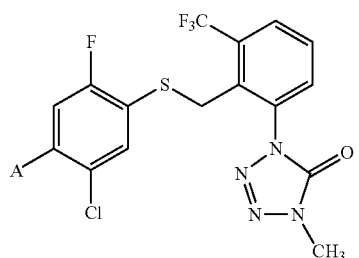
(HJ1001)
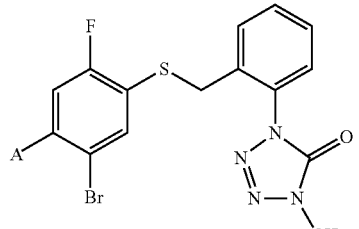
(HJ1002)
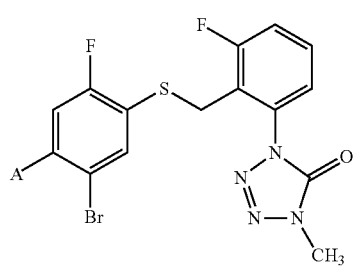
(HJ1003)
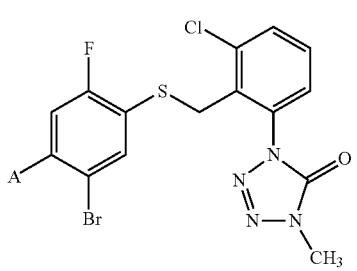
(HJ1004)
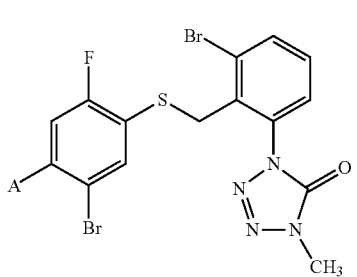
(HJ1005)
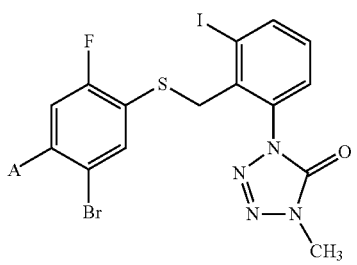
(HJ1006)
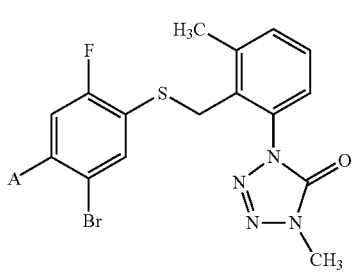
(HJ1007)
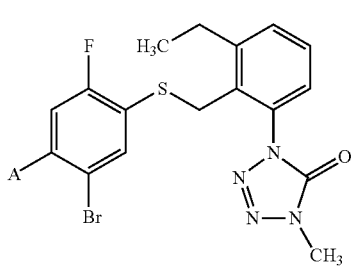
(HJ1008)
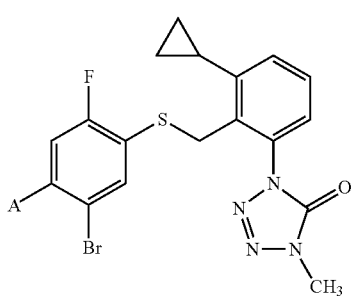

(HJ1009) 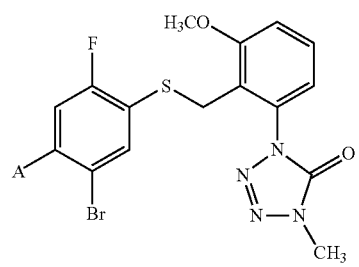
(HJ1010) 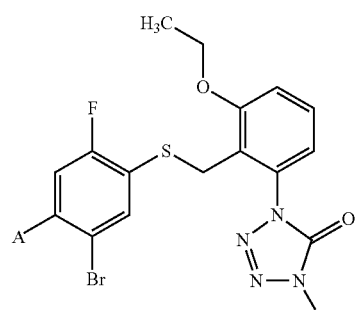
(HJ1011) 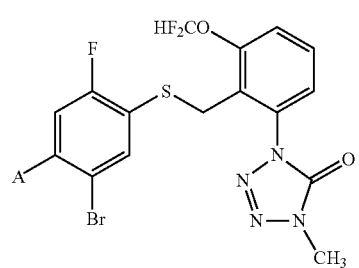
(HJ1012) 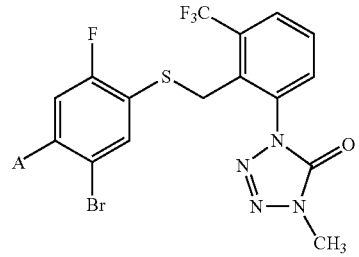
(HK1001) 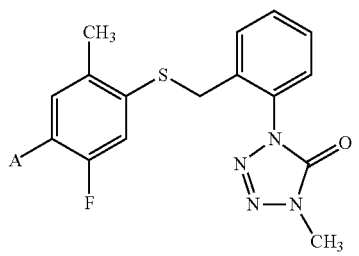
(HK1002) 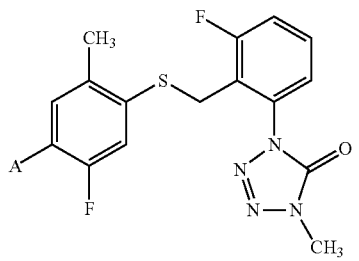
(HK1003) 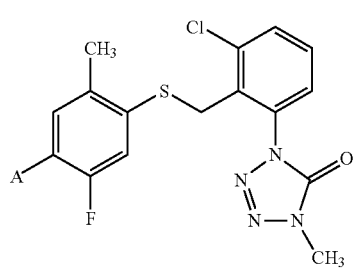
(HK1004) 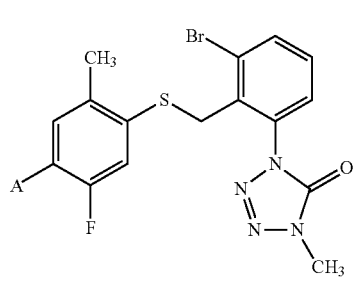
(HK1005) 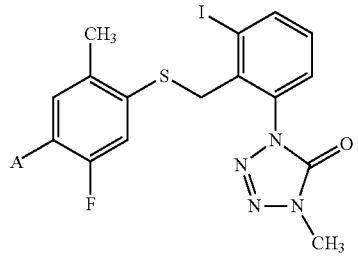
(HK1006) 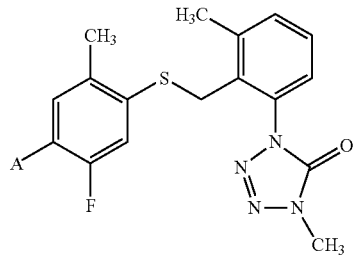
(HK1007) 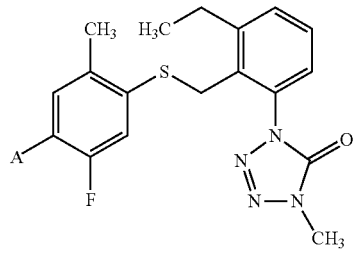
(HK1008) 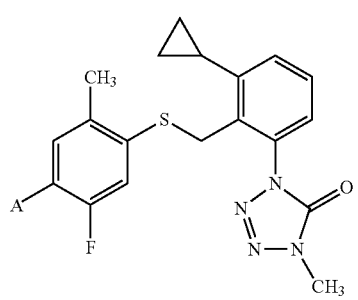

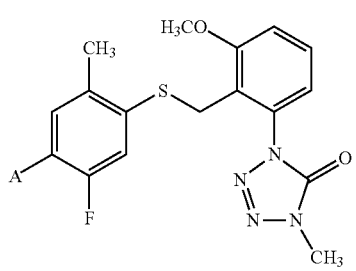
(HK1009)
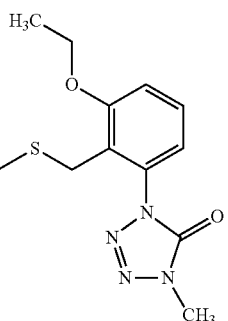
(HK1010)
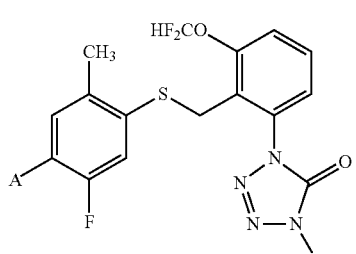
(HK1011)
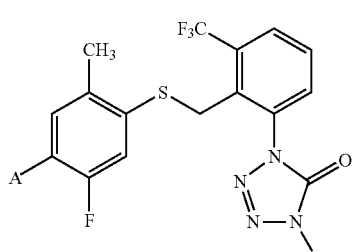
(HK1012)
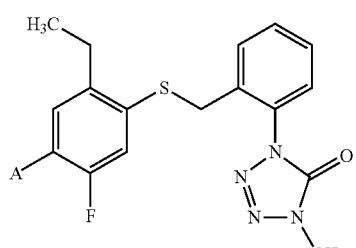
(HL1001)
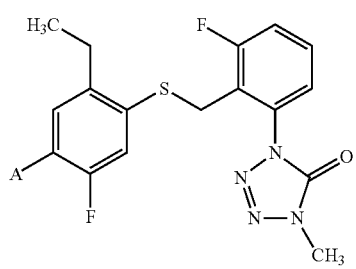
(HL1002)
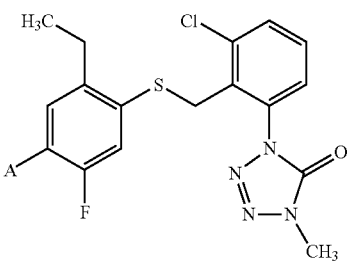
(HL1003)
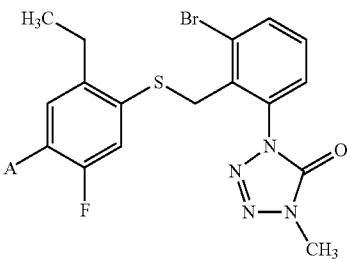
(HL1004)
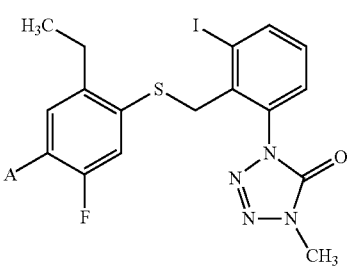
(HL1005)
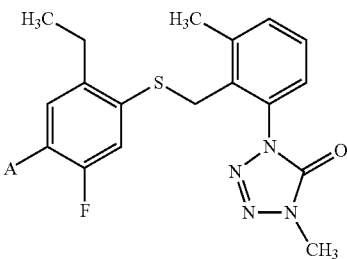
(HL1006)
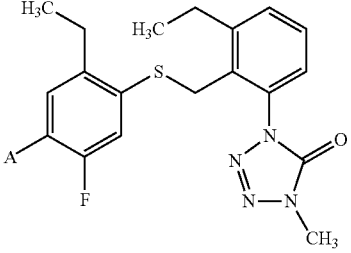
(HL1007)
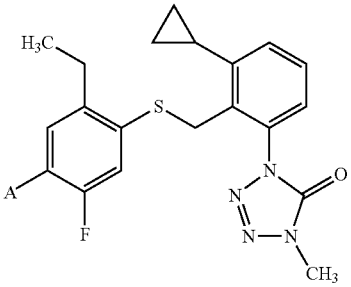
(HL1008)

-continued
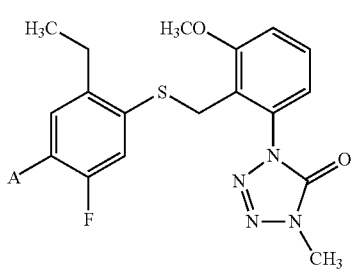
(HL1009)
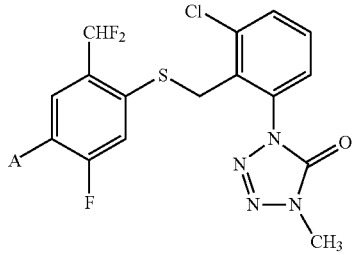
(HM1003)
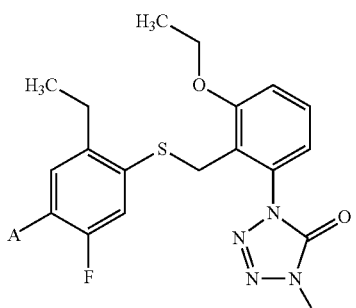
(HL1010)
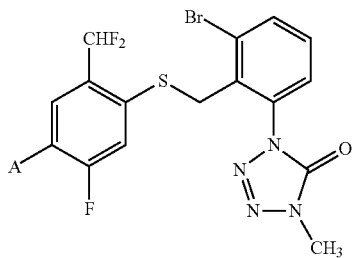
(HM1004)
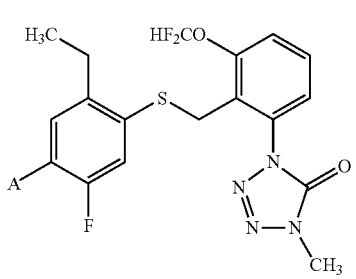
(HL1011)
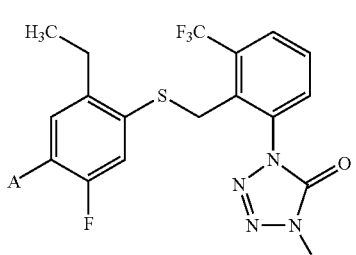
(HL1012)
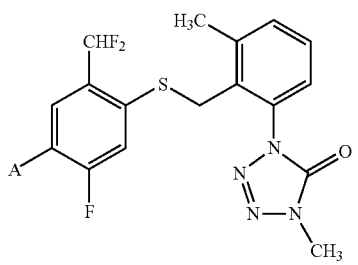
(HM1005)
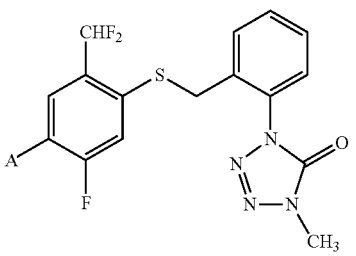
(HM1001)
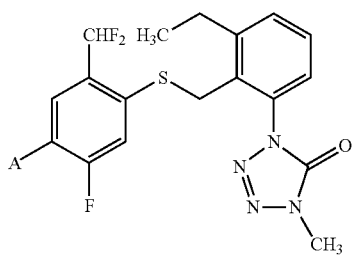
(HM1006)
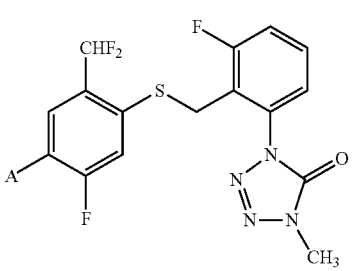
(HM1002)
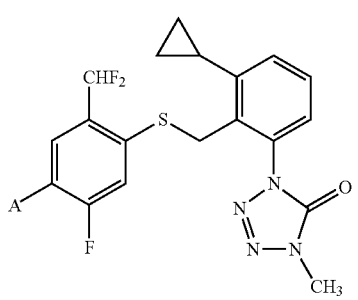
(HM1007)
(HM1008)

(HM1009)
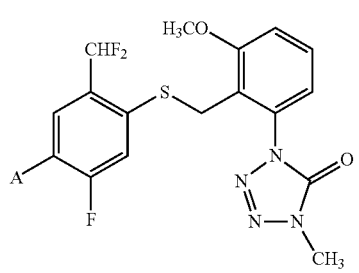
(HM1010)
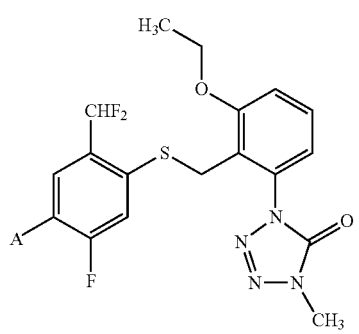
(HM1011)
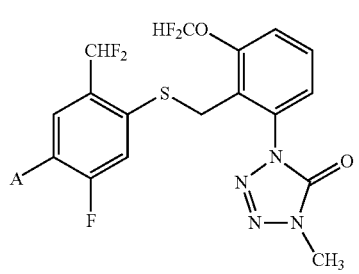
(HM1012)
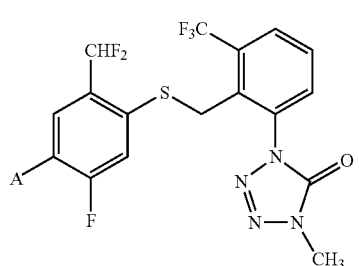
(HN1001)
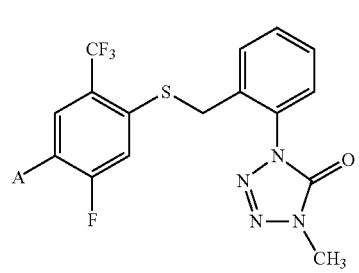
(HN1002)
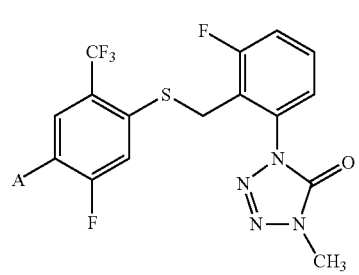
(HN1003)
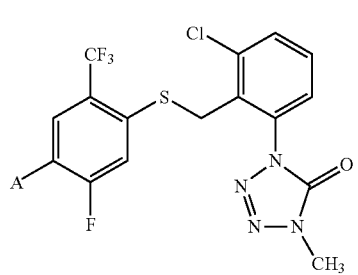
(HN1004)
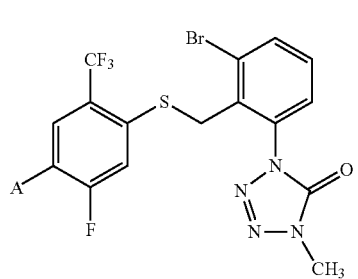
(HN1005)
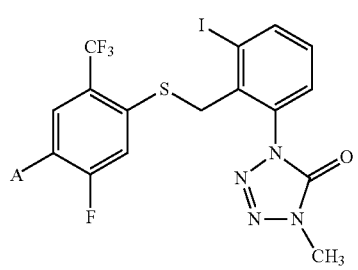
(HN1006)
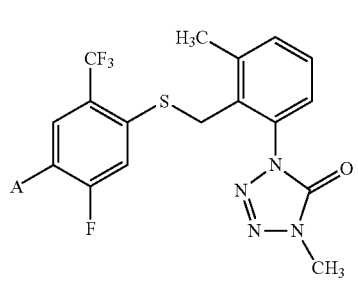
(HN1007)
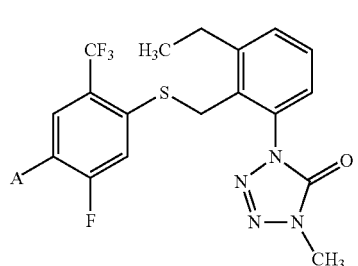
(HN1008)
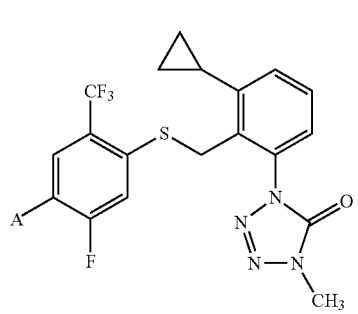

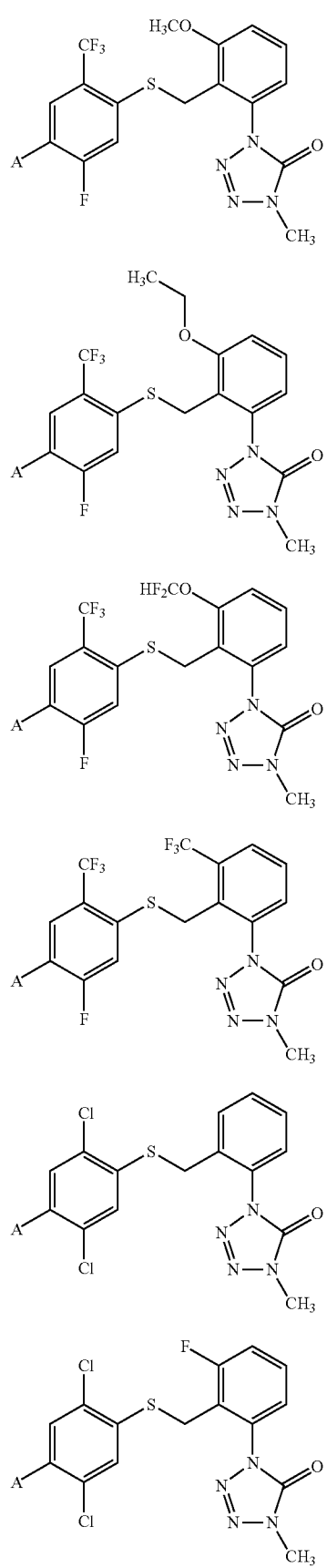
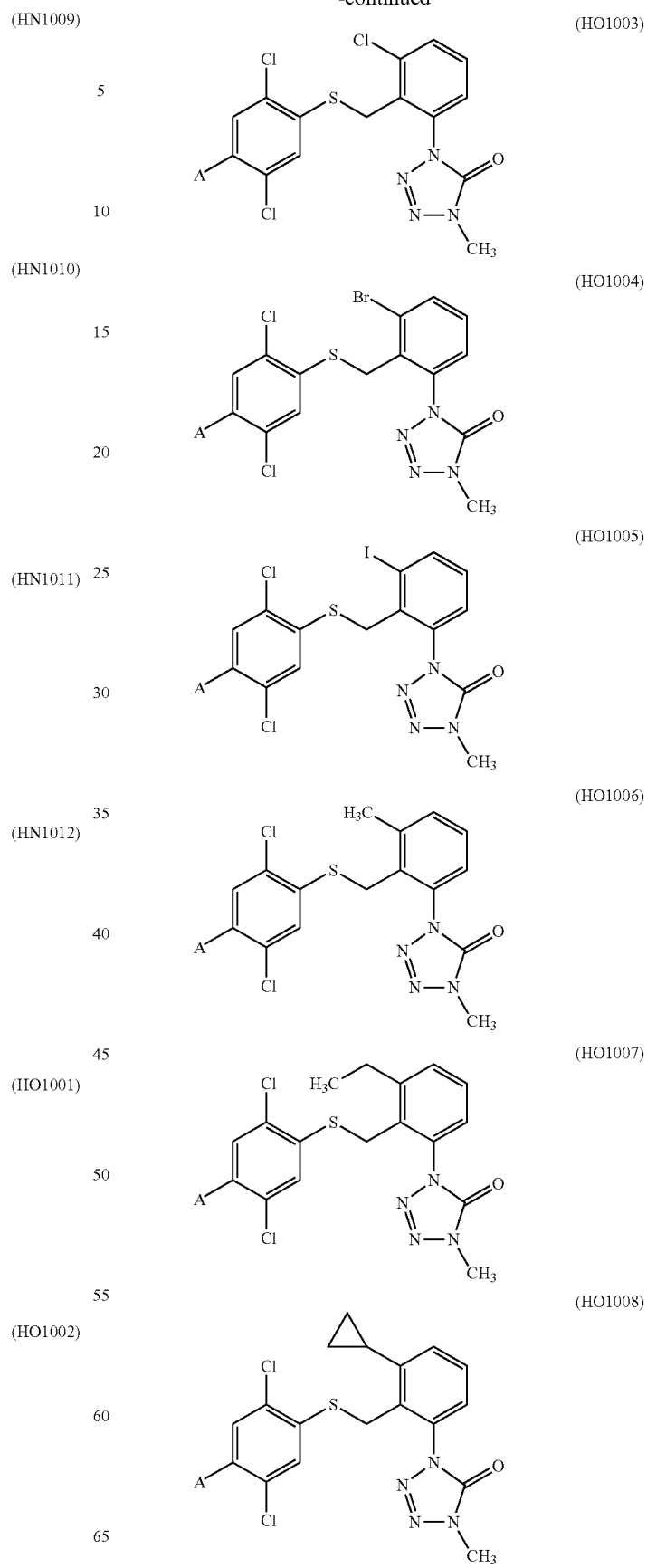

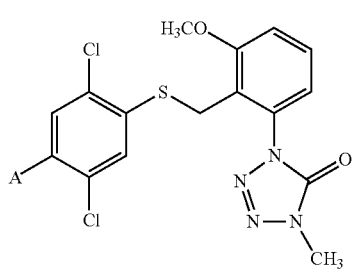
(HO1009)
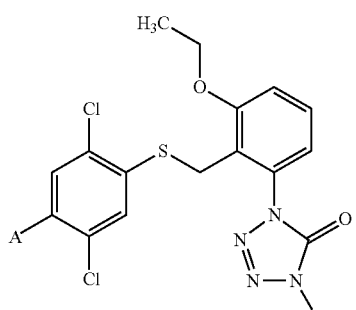
(HO1010)
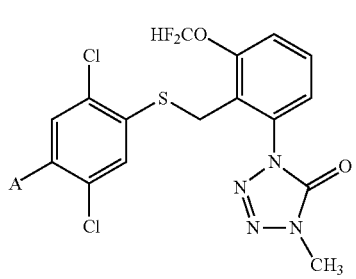
(HO1011)
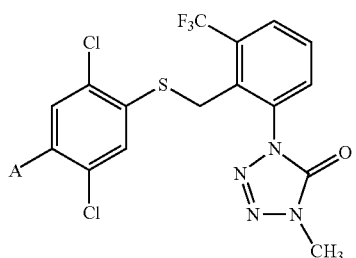
(HO1012)
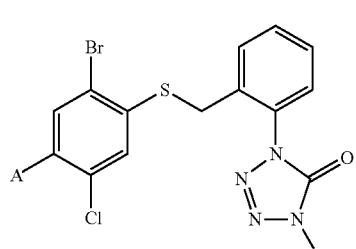
(HP1001)
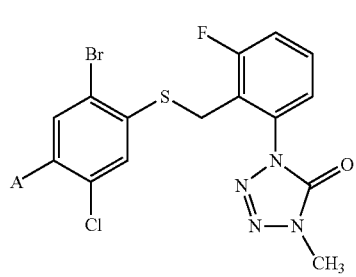
(HP1002)
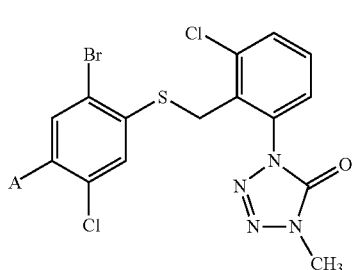
(HP1003)
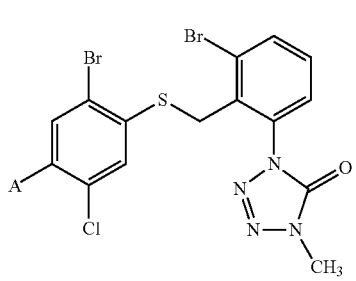
(HP1004)
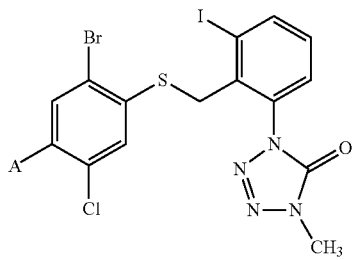
(HP1005)
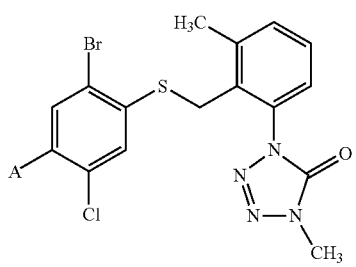
(HP1006)
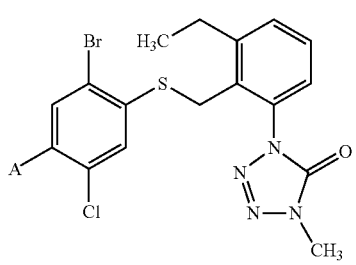
(HP1007)
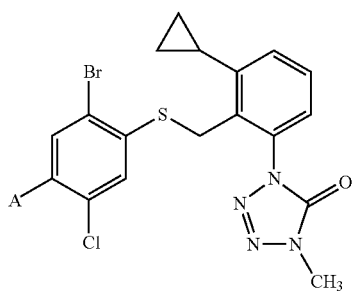
(HP1008)

(HP1009)
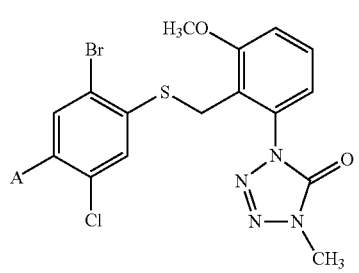
(HP1010)
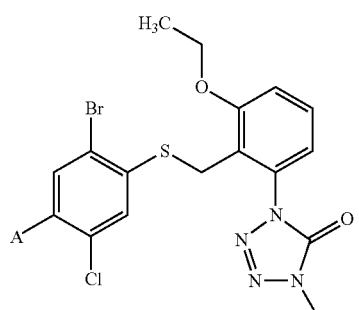
(HP1011)
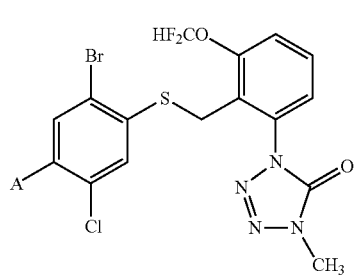
(HP1012)
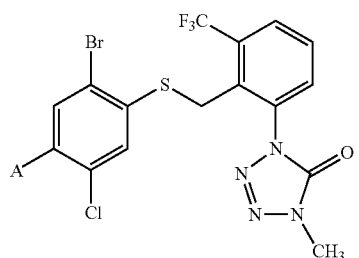
(HQ1001)
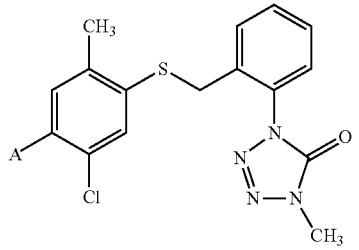
(HQ1002)
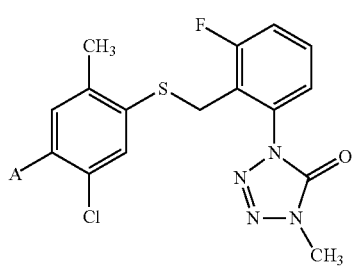
(HQ1003)
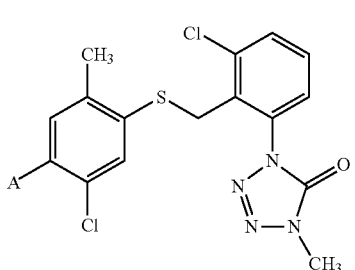
(HQ1004)
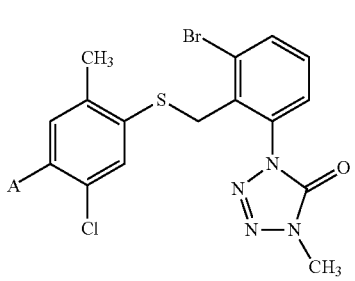
(HQ1005)
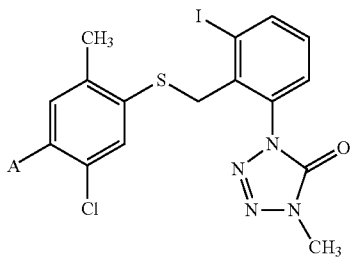
(HQ1006)
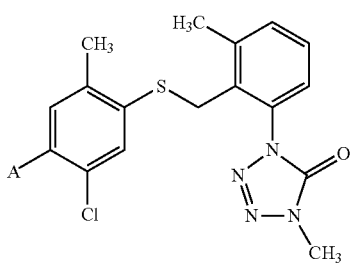
(HQ1007)
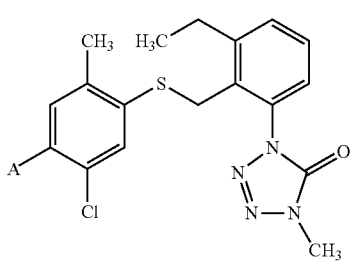
(HQ1008)
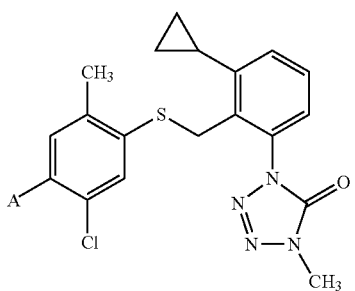

-continued
(HQ1009)
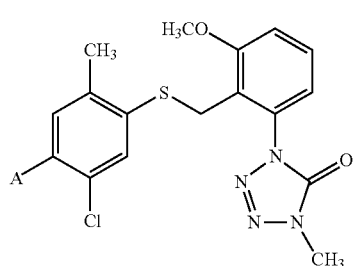
(HQ1010)
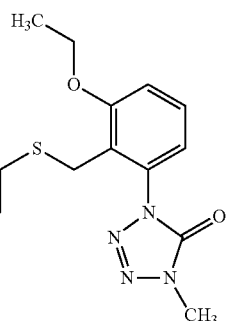
(HQ1011)
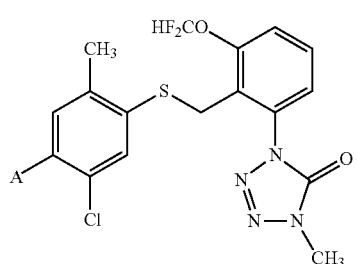
(HQ1012)
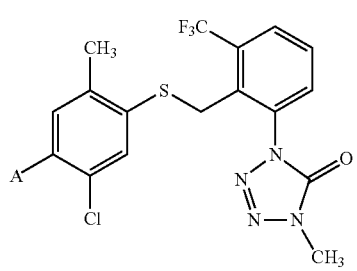
(HR1001)
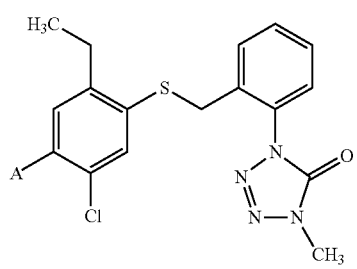
(HR1002)
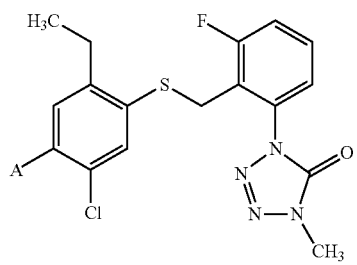
-continued
(HR1003)
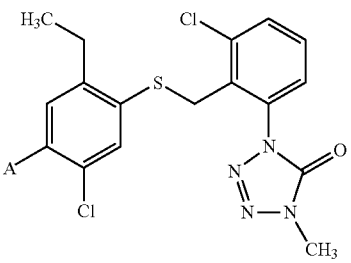
(HR1004)
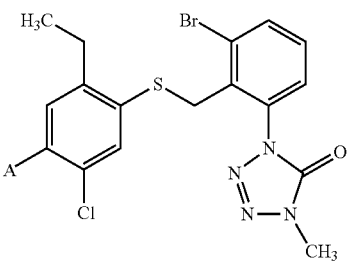
(HR1005)
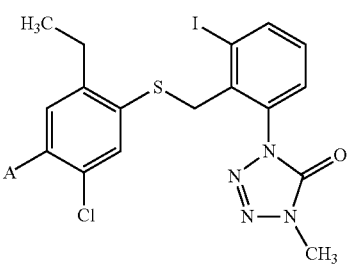
(HR1006)
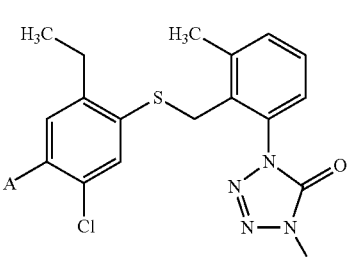
(HR1007)
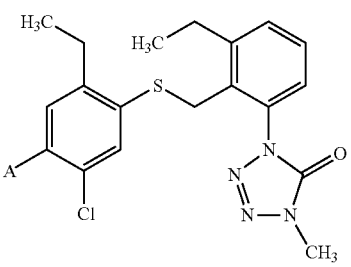
(HR1008)
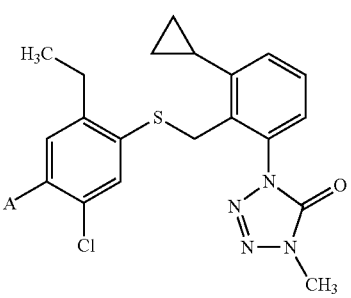

-continued
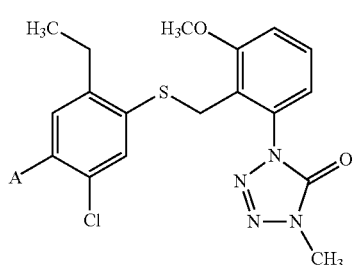
(HR1009)
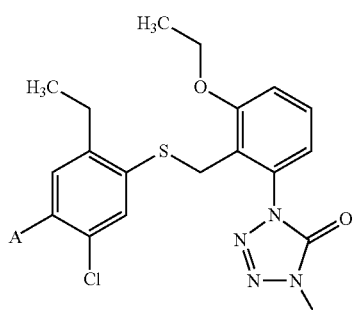
(HR1010)
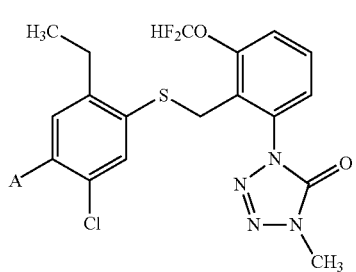
(HR1011)
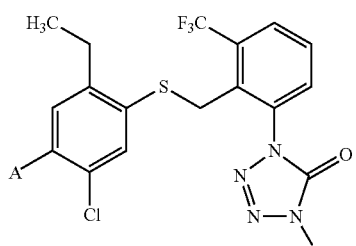
(HR1012)
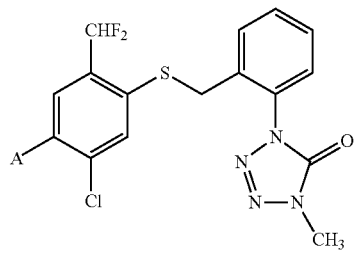
(HS1001)
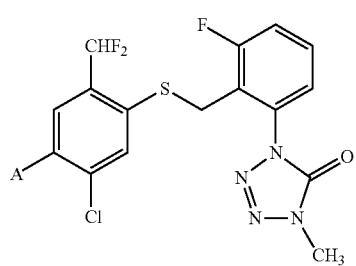
(HS1002)
-continued
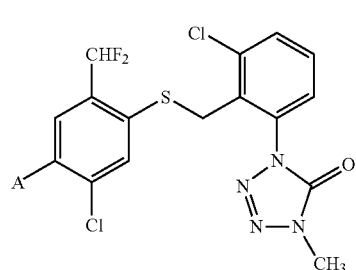
(HS1003)
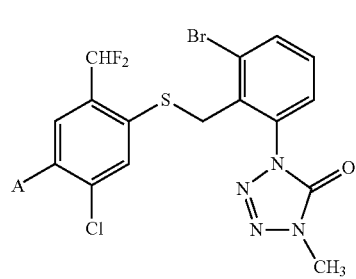
(HS1004)
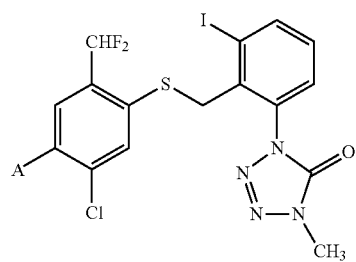
(HS1005)
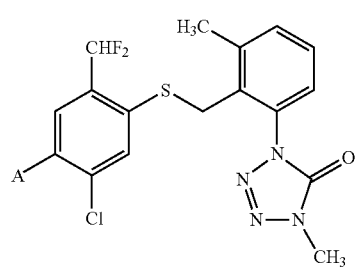
(HS1006)
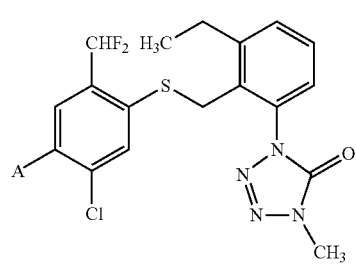
(HS1007)
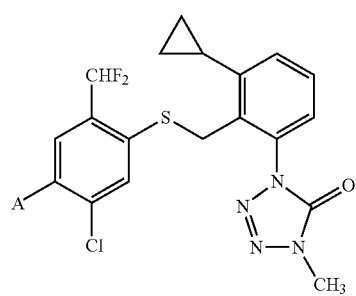
(HS1008)

(HS1009) 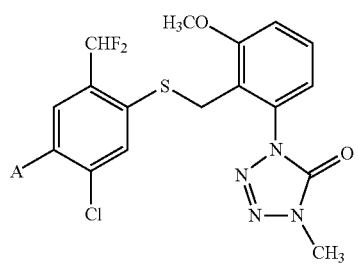
(HS1010) 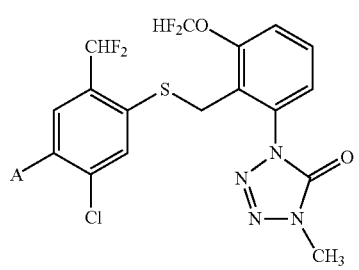
(HS1011) 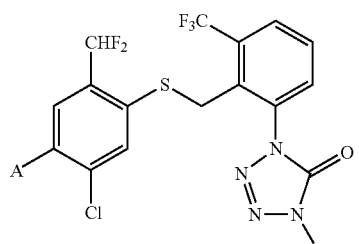
(HS1012) 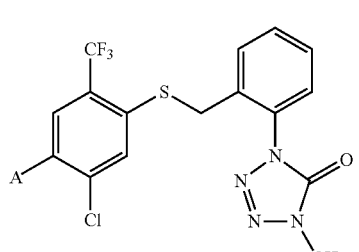
(HT1001) 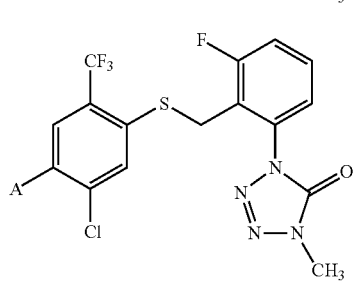
(HT1002)
(HT1003) 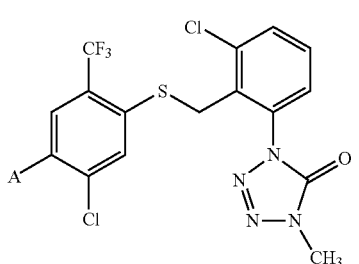
(HT1004) 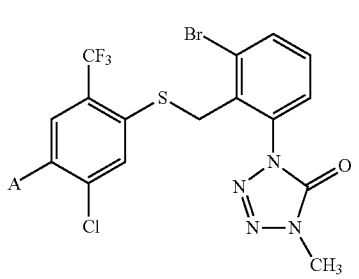
(HT1005) 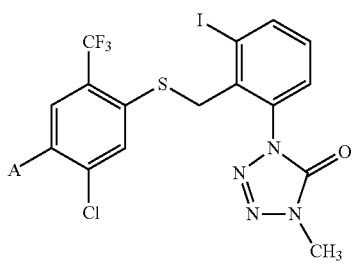
(HT1006) 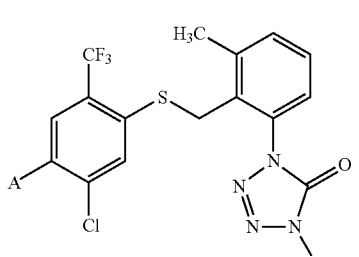
(HT1007) 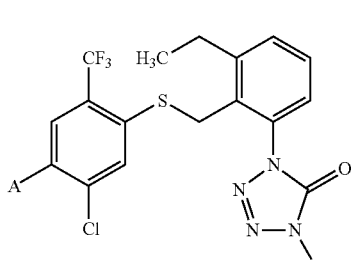
(HT1008) 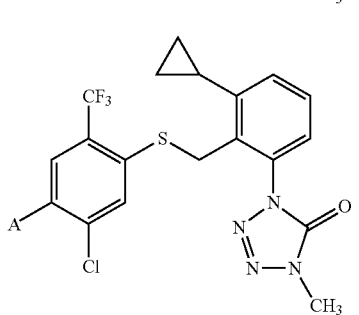

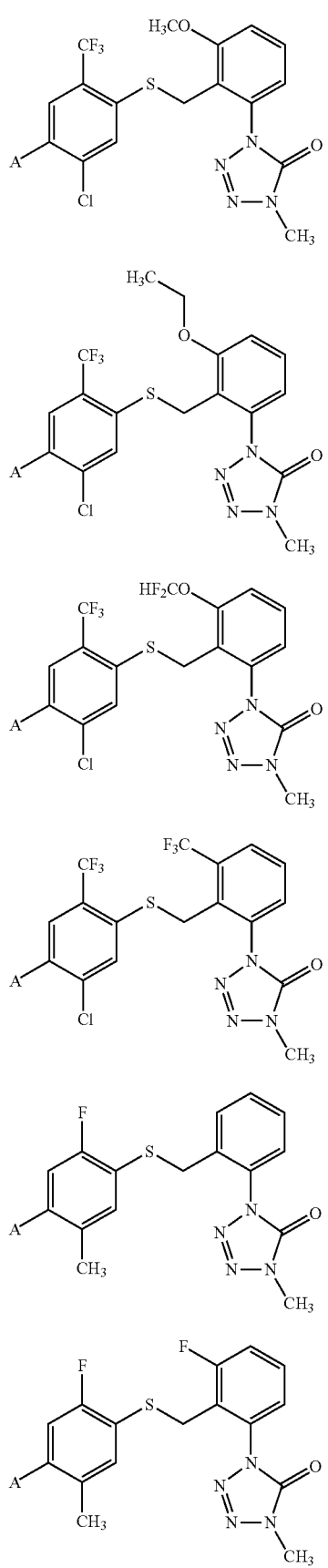
(HT1009)
(HT1010)
(HT1011)
(HT1012)
(HU1001)
(HU1002)
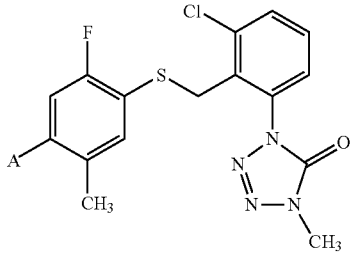
(HU1003)
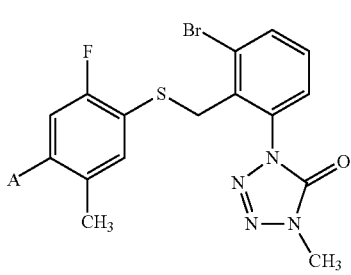
(HU1004)
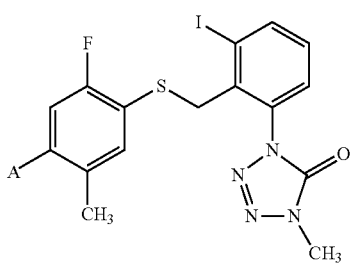
(HU1005)
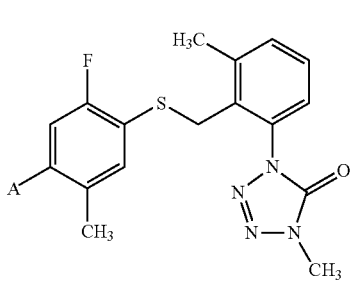
(HU1006)
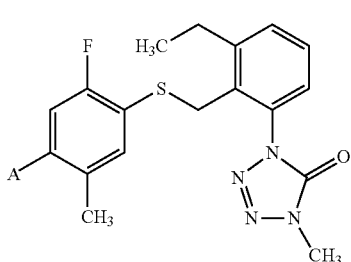
(HU1007)
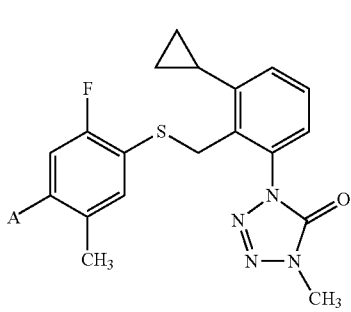
(HU1008)

71
-continued
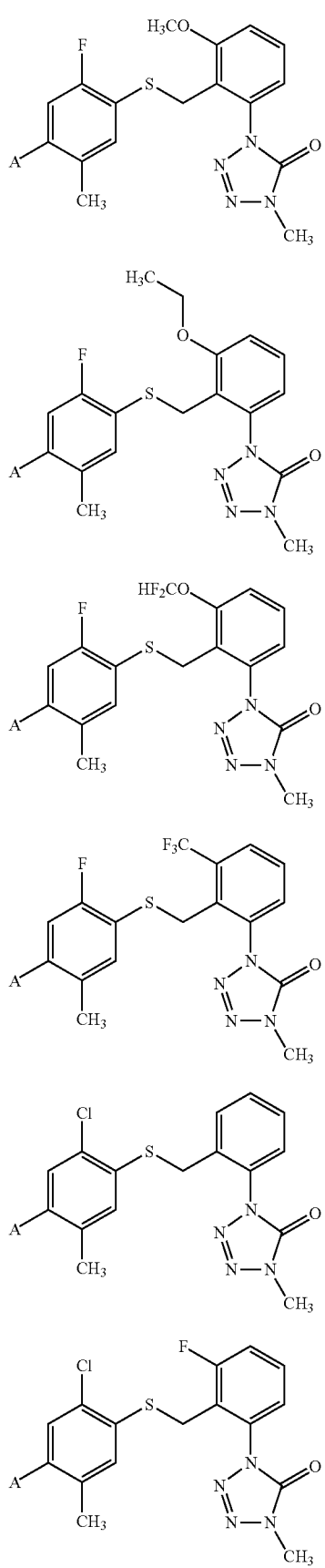
(HU1009)
(HU1010)
(HU1011)
(HU1012)
(HV1001)
(HV1002)
72
-continued
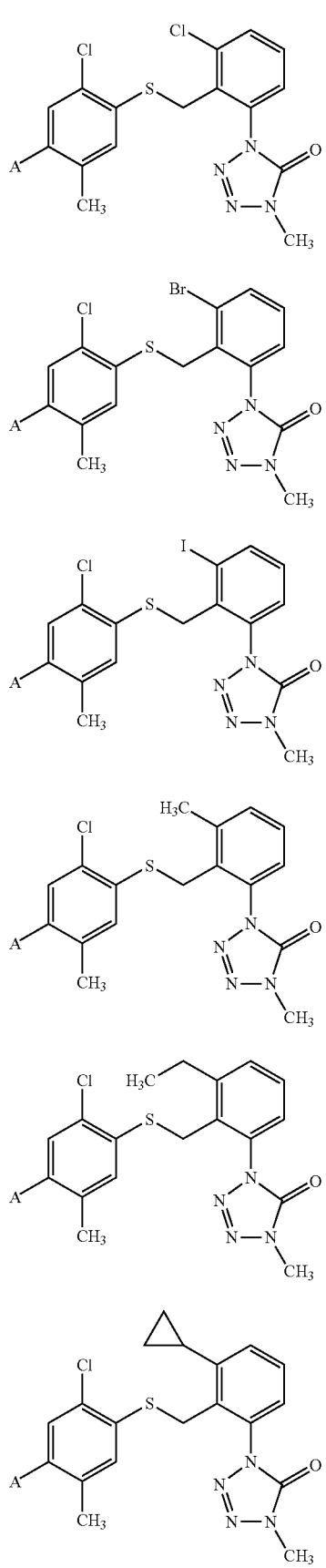
(HV1003)
(HV1004)
(HV1005)
(HV1006)
(HV1007)
(HV1008)

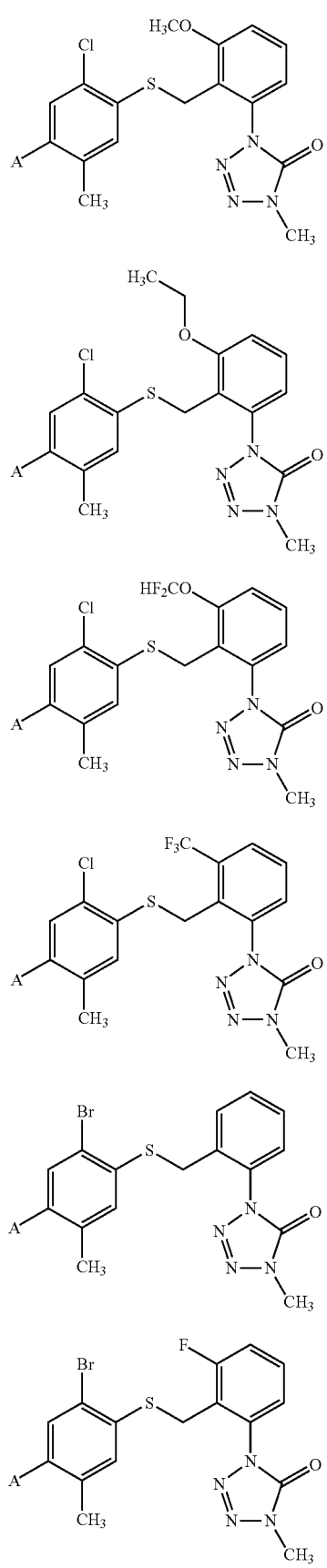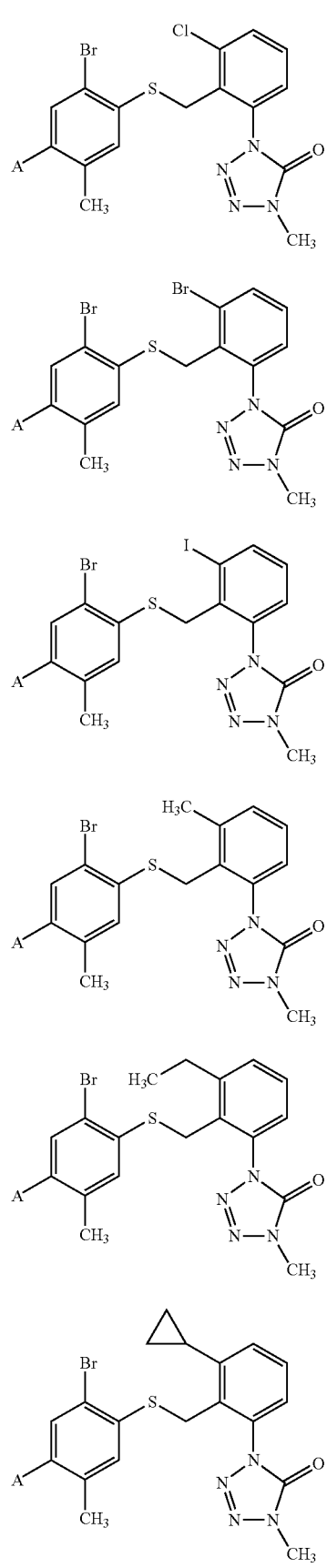

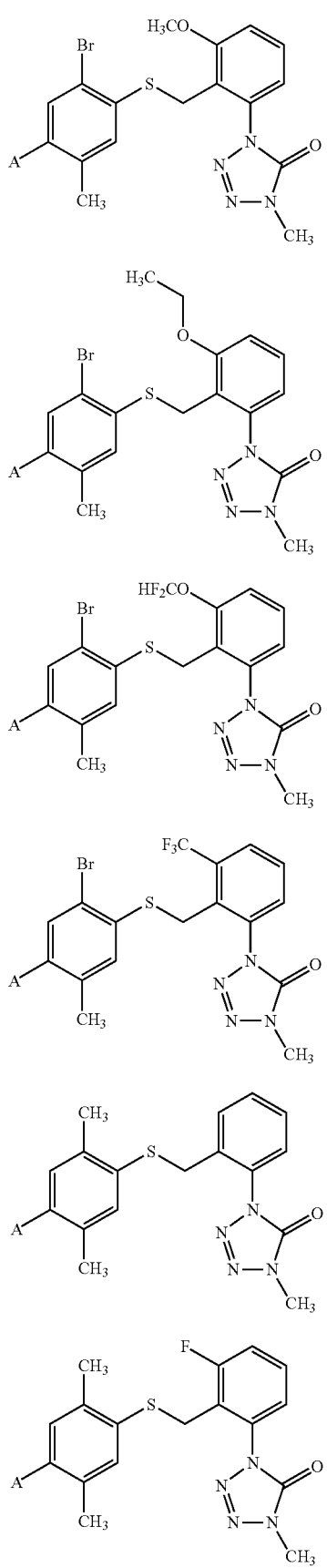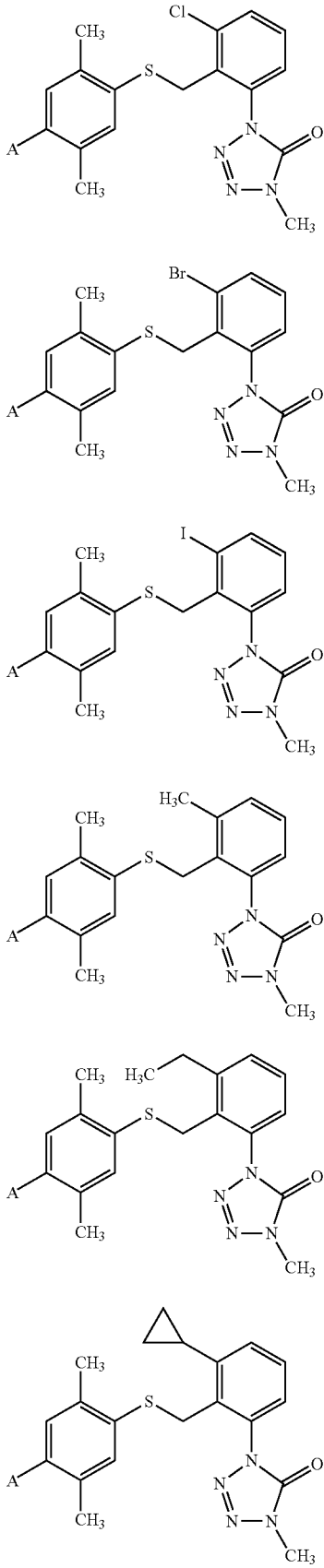

(HX1009)
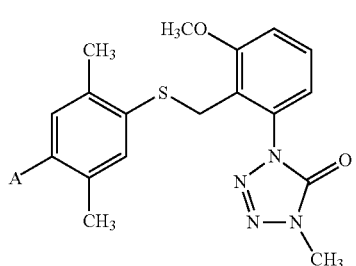
(HX1010)
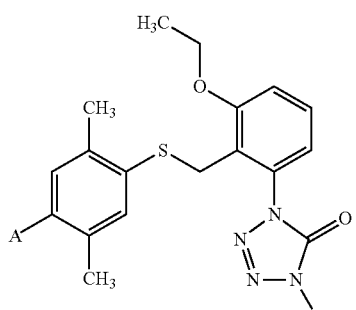
(HX1011)
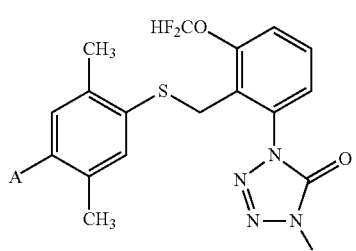
(HX1012)
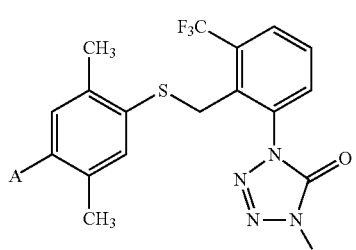
(HY1001)
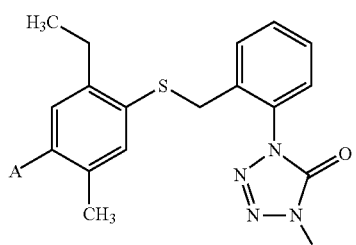
(HY1002)
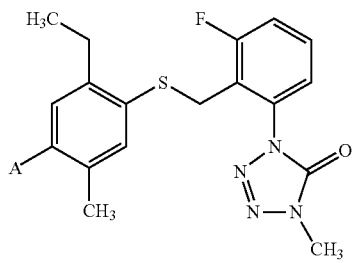
(HY1003)
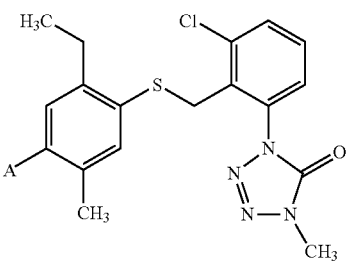
(HY1004)
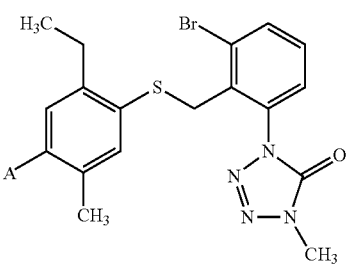
(HY1005)
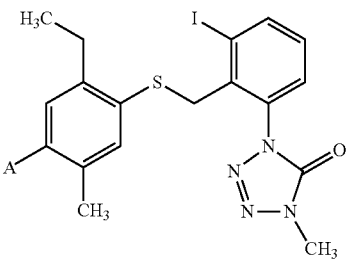
(HY1006)
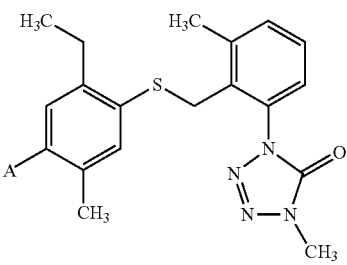
(HY1007)
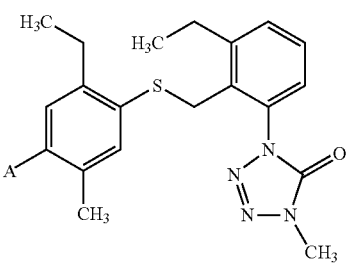
(HY1008)
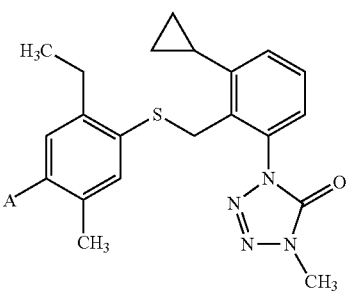

-continued
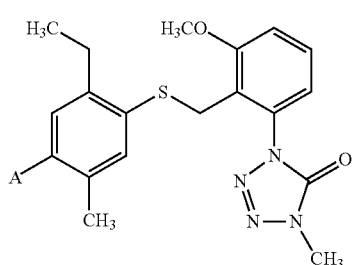 (HY1009)
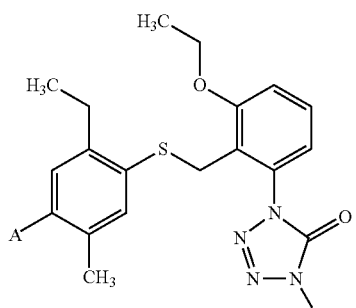 (HY1010)
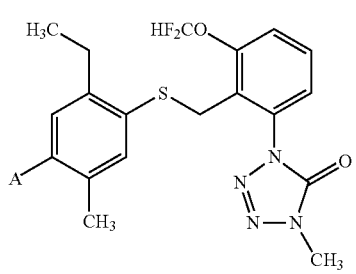 (HY1011)
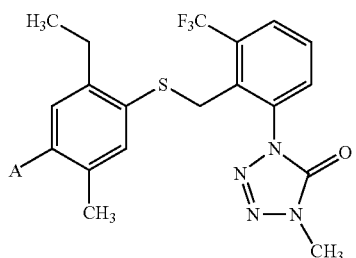 (HY1012)
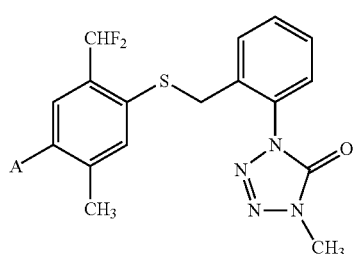 (HZ1001)
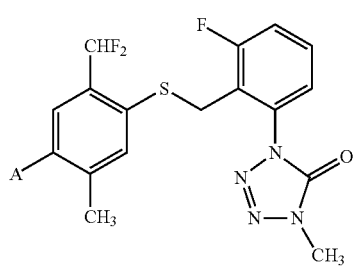 (HZ1002)
-continued
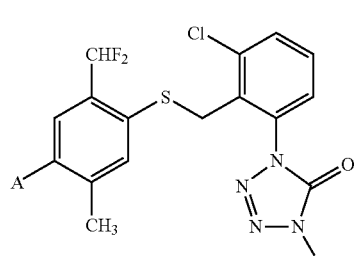 (HZ1003)
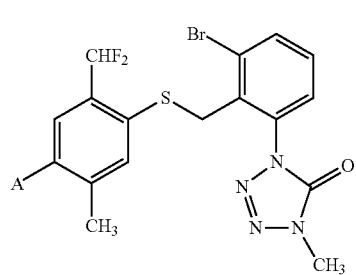 (HZ1004)
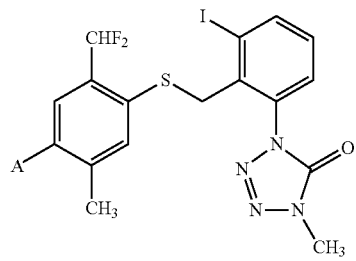 (HZ1005)
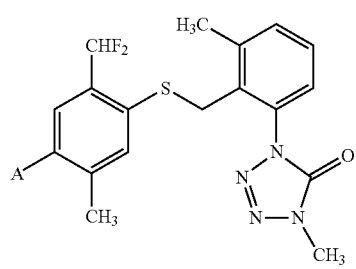 (HZ1006)
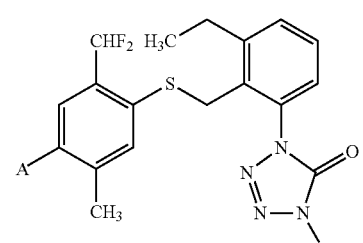 (HZ007)
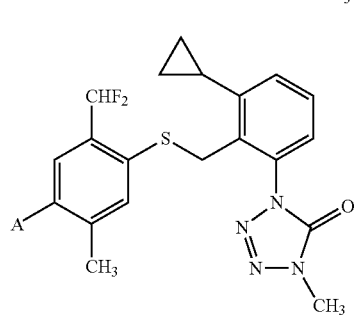 (HZ1008)

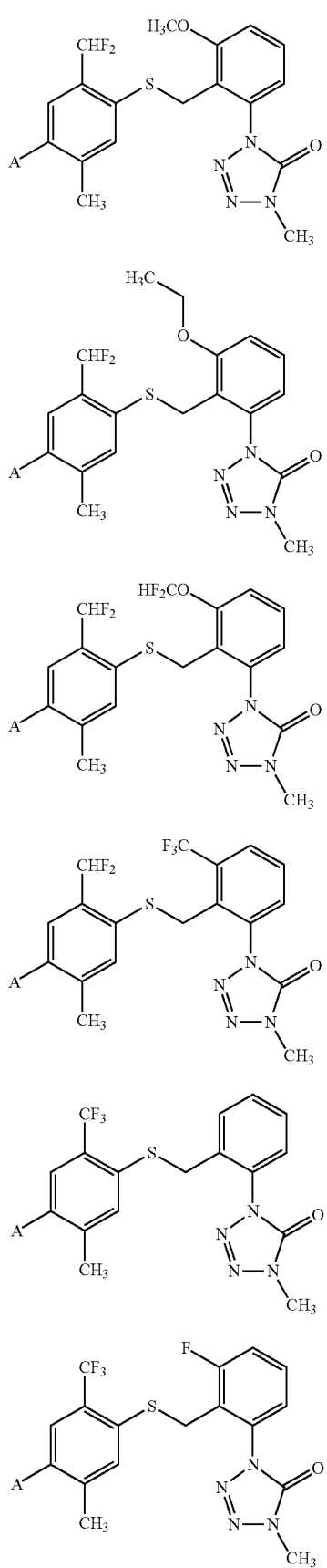
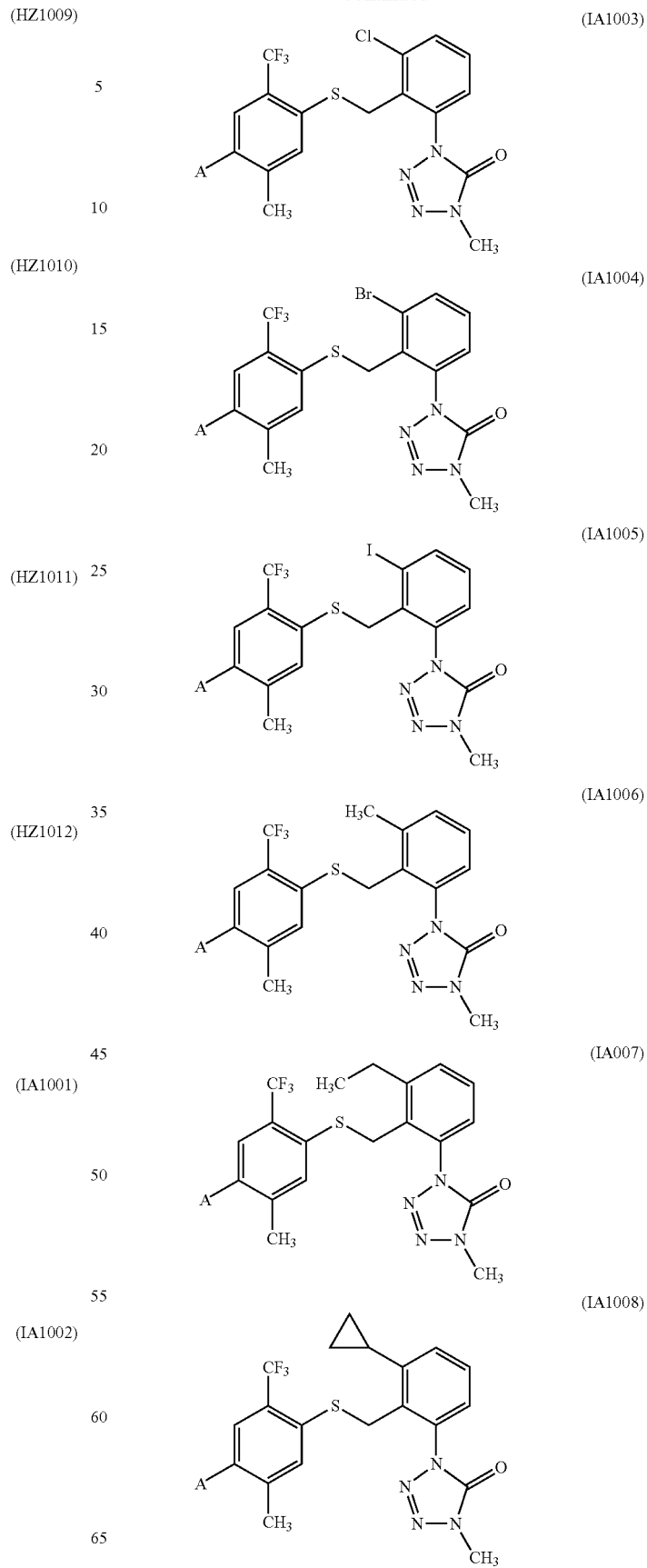

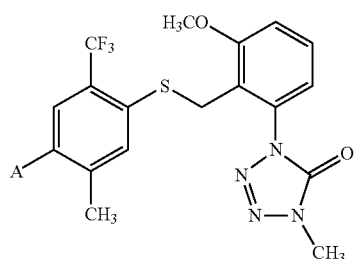
(IA1009)
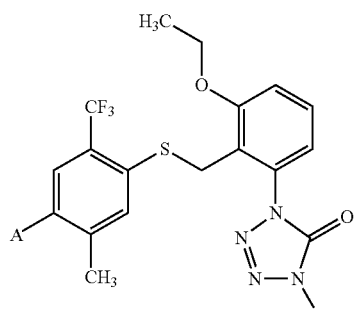
(IA1010)
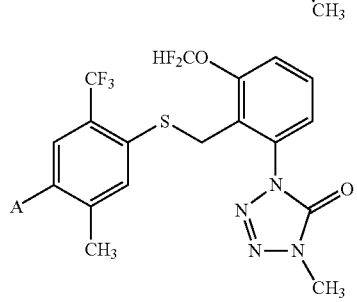
(IA1011)
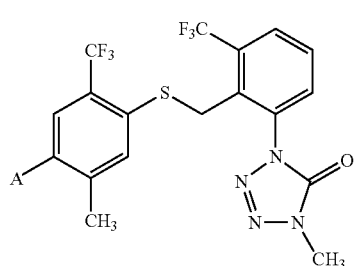
(IA1012)
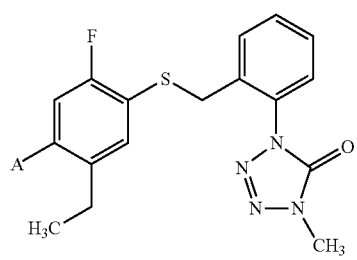
(IB1001)
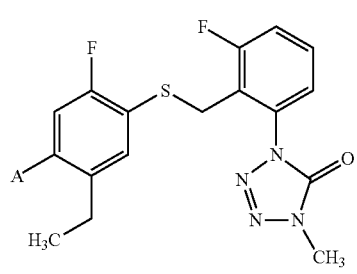
(IB1002)
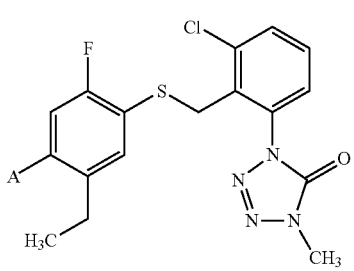
(IB1003)
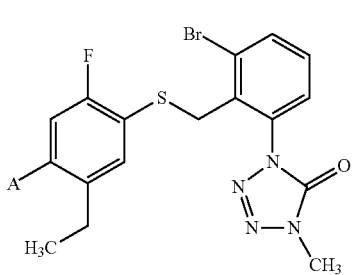
(IB1004)
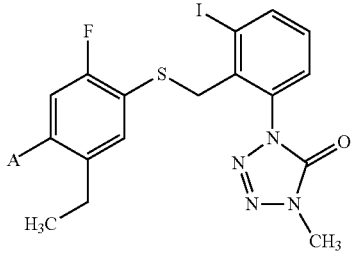
(IB1005)
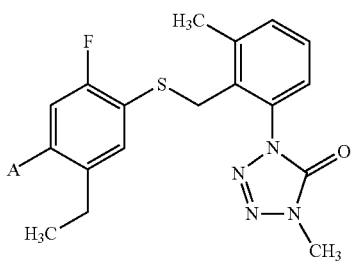
(IB1006)
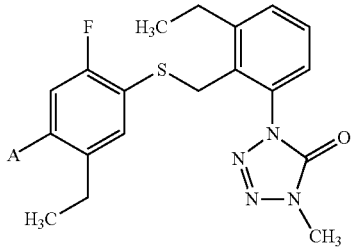
(IB1007)
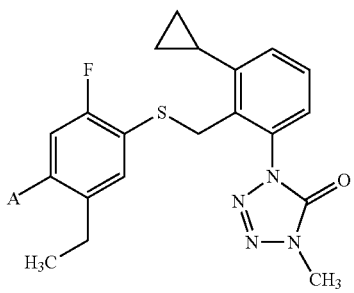
(IB1008)

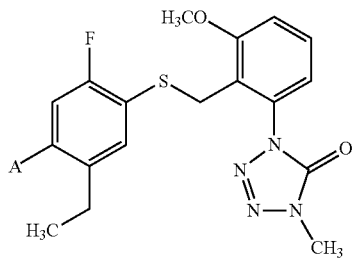
(IB1009)
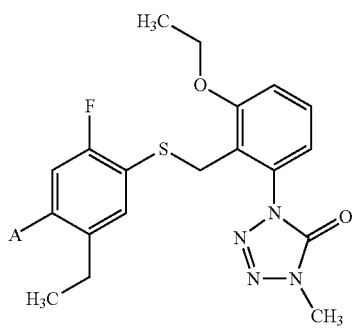
(IB1010)
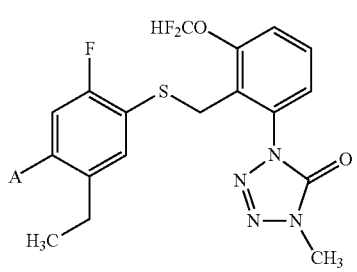
(IB1011)
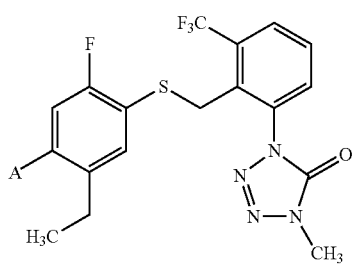
(IB1012)
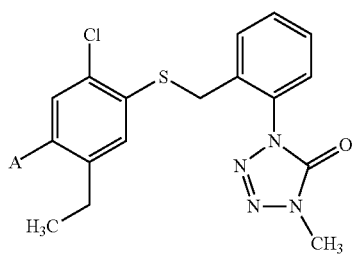
(IC1001)
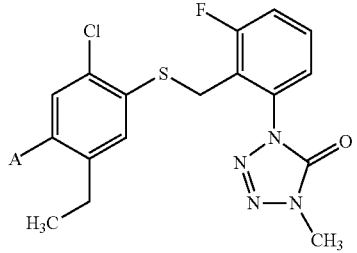
(IC1002)
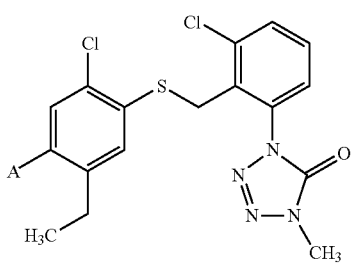
(IC1003)
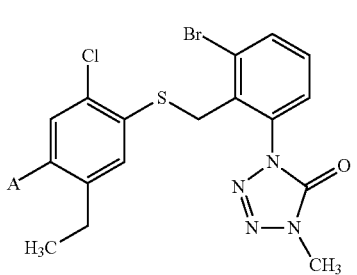
(IC1004)
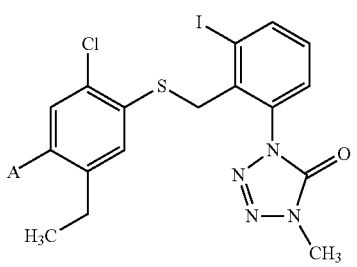
(IC1005)
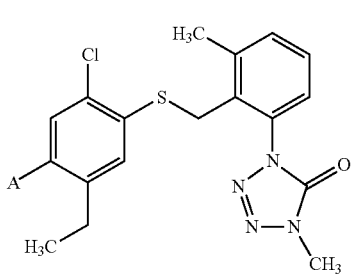
(IC1006)
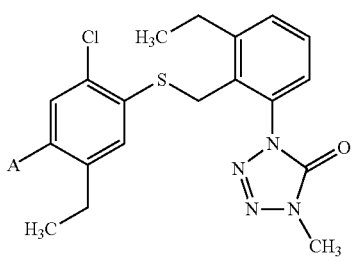
(IC1007)
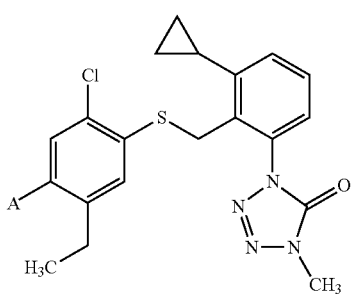
(IC1008)

-continued
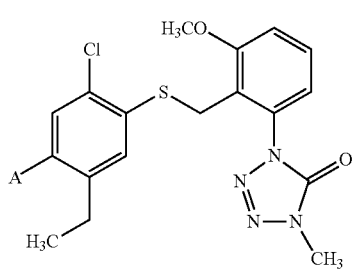
(IC1009)
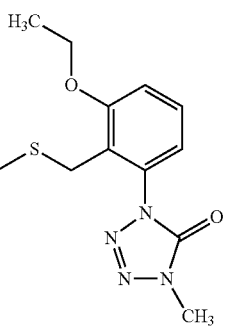
(IC1010)
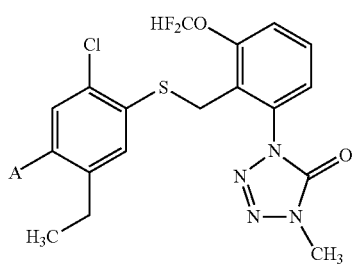
(IC1011)
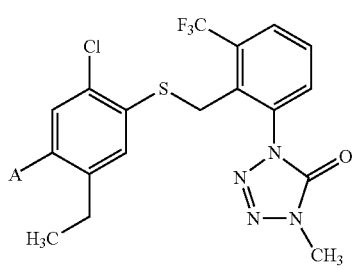
(IC1012)
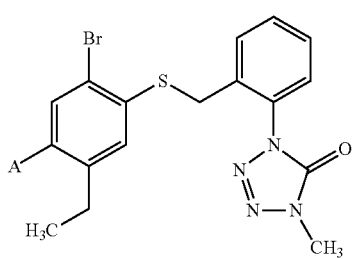
(ID1001)
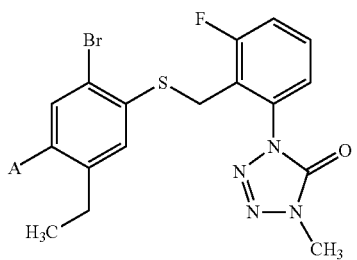
(ID1002)
-continued
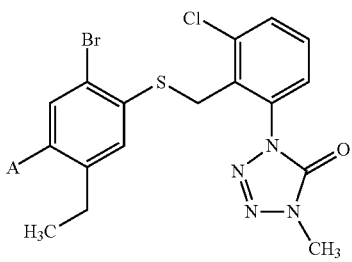
(ID1003)
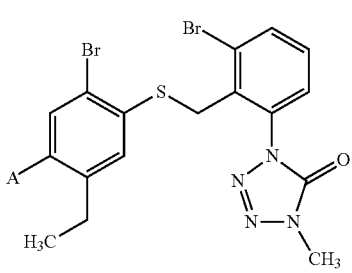
(ID1004)
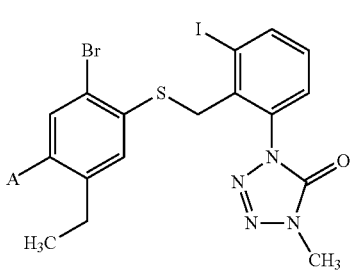
(ID1005)
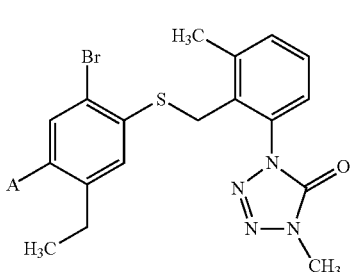
(ID1006)
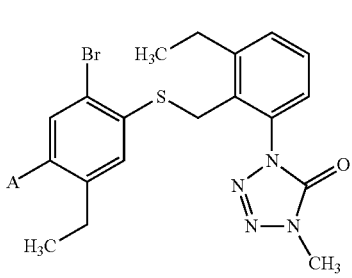
(ID1007)
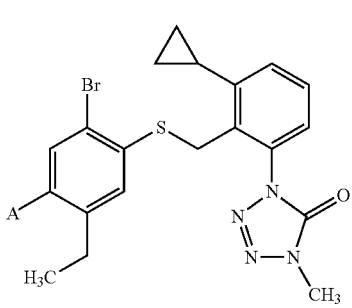
(ID1008)

-continued
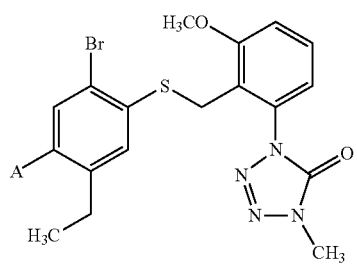
(ID1009)
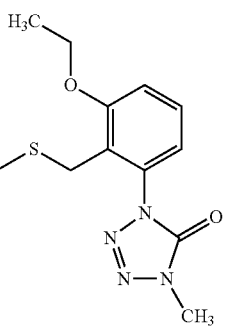
(ID1010)
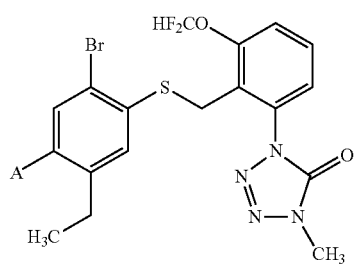
(ID1011)
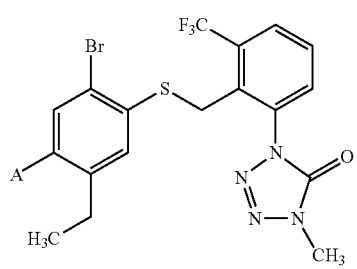
(ID1012)
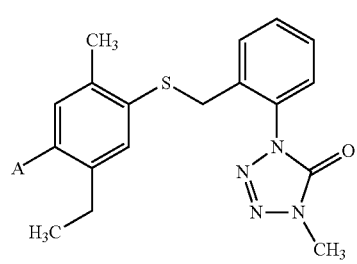
(IE1001)
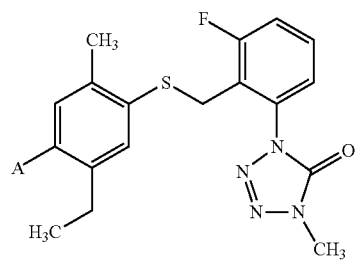
(IE1002)
-continued
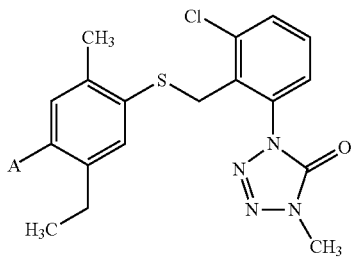
(IE1003)
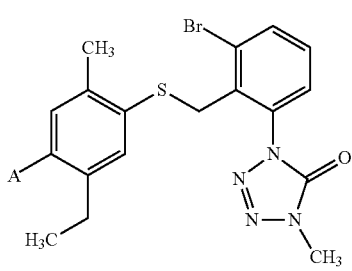
(IE1004)
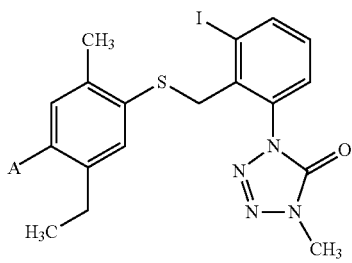
(IE1005)
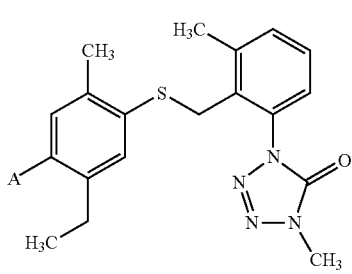
(IE1006)
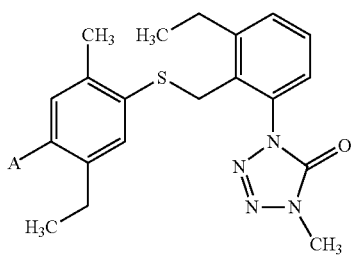
(IE1007)
(IE1008)

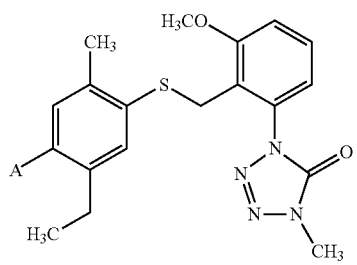
(IE1009)
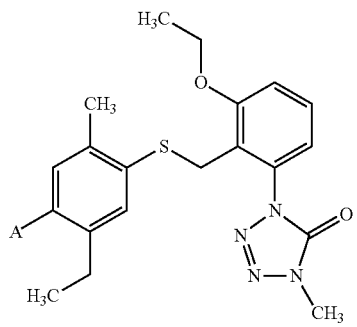
(IE1010)
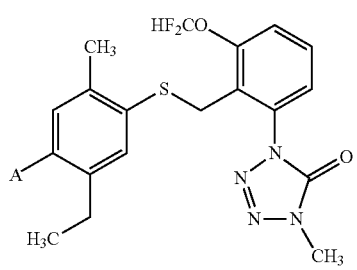
(IE1011)
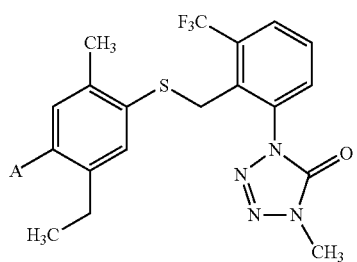
(IE1012)
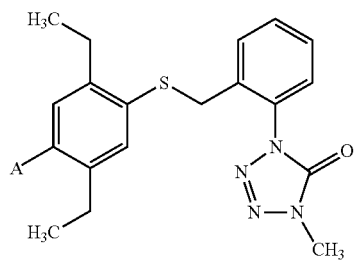
(IF1001)
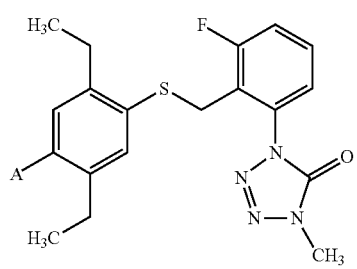
(IF1002)
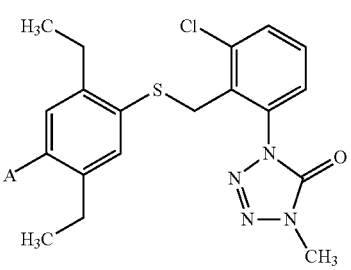
(IF1003)
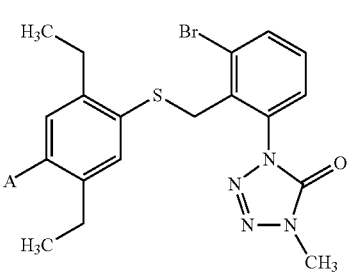
(IF1004)
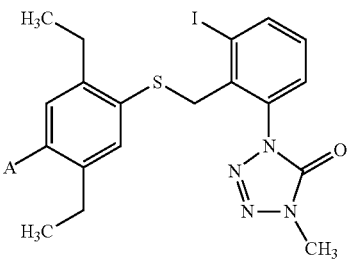
(IF1005)
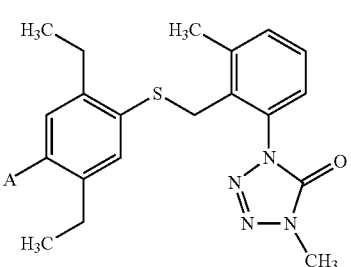
(IF1006)
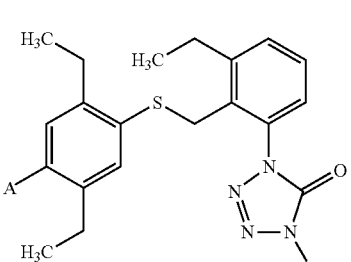
(IF1007)
(IF1008)

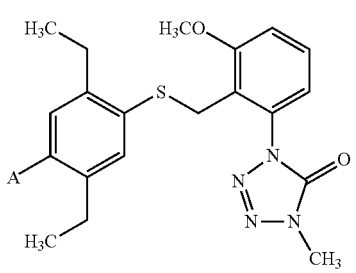 (IF1009)
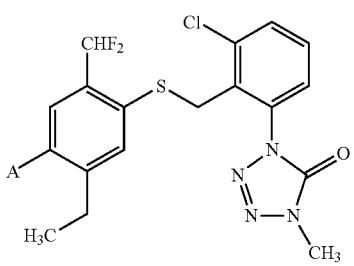 (IG1003)
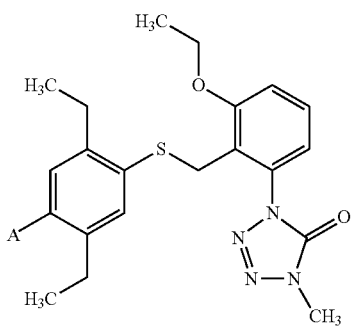 (IF1010)
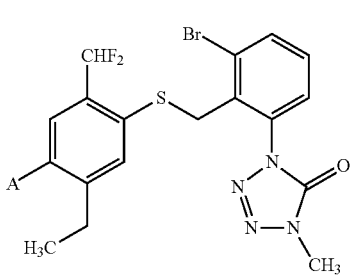 (IG1004)
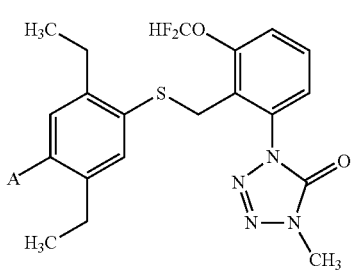 (IF1011)
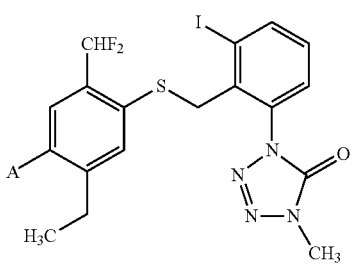 (IG1005)
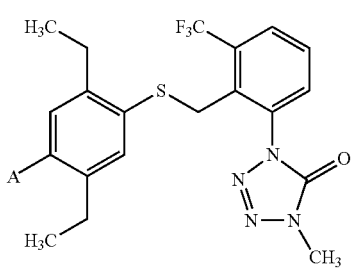 (IF1012)
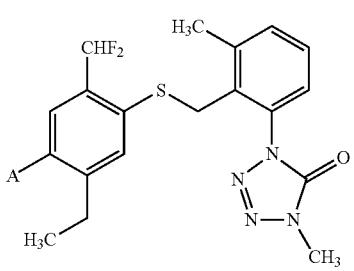 (IG1006)
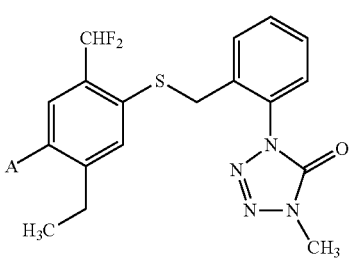 (IG1001)
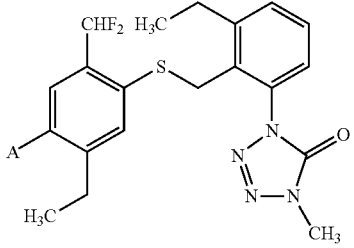 (IG1007)
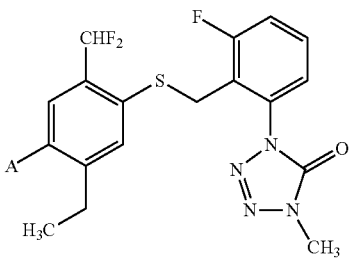 (IG1002)
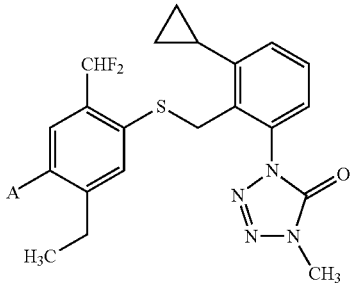 (IG1008)

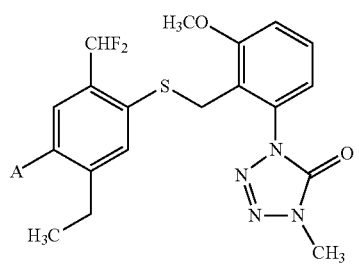
(IG1009)
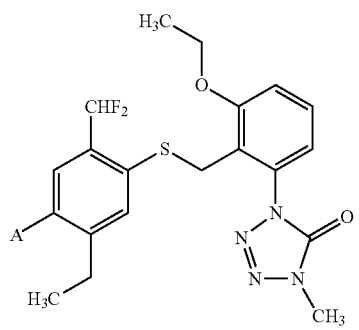
(IG1010)
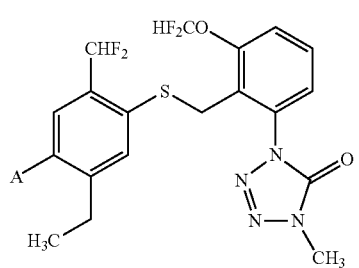
(IG1011)
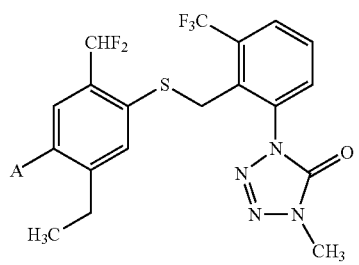
(IG1012)
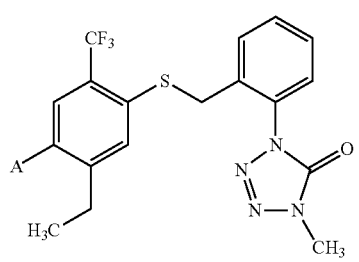
(IH1001)
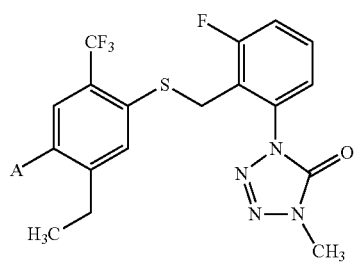
(IH1002)
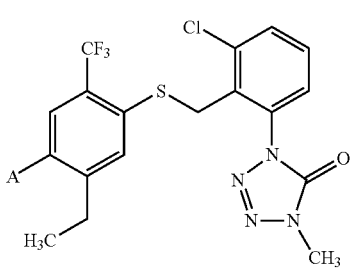
(IH1003)
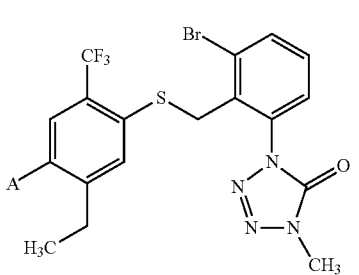
(IH1004)
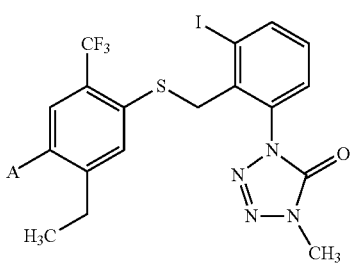
(IH1005)
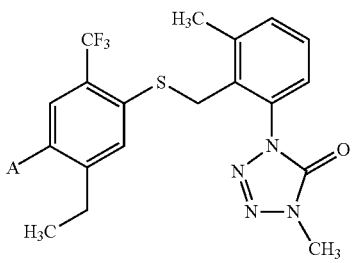
(IH1006)
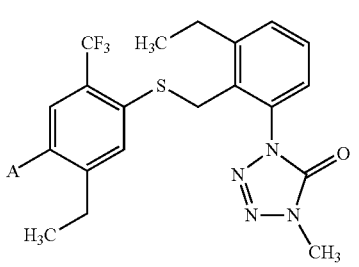
(IH1007)
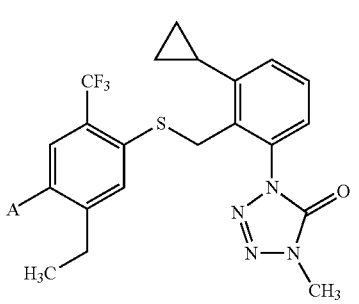
(IH1008)

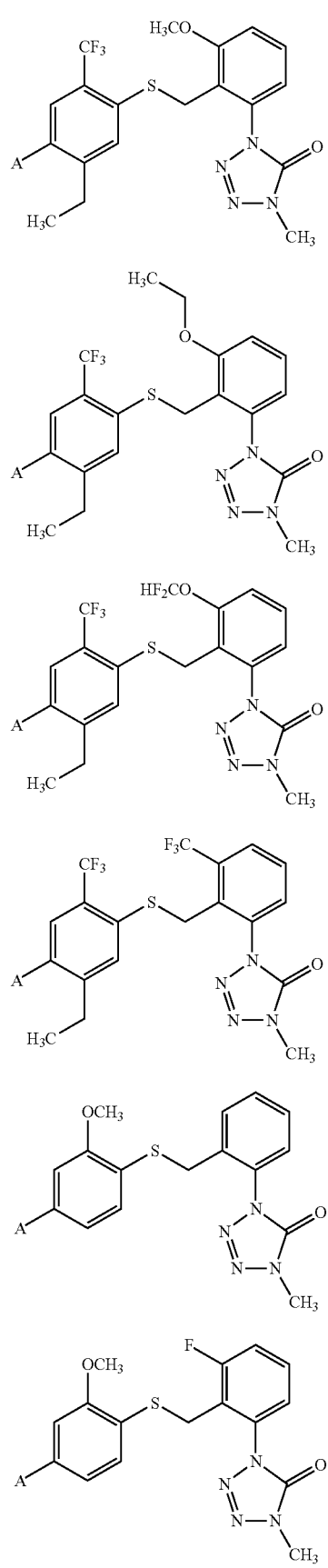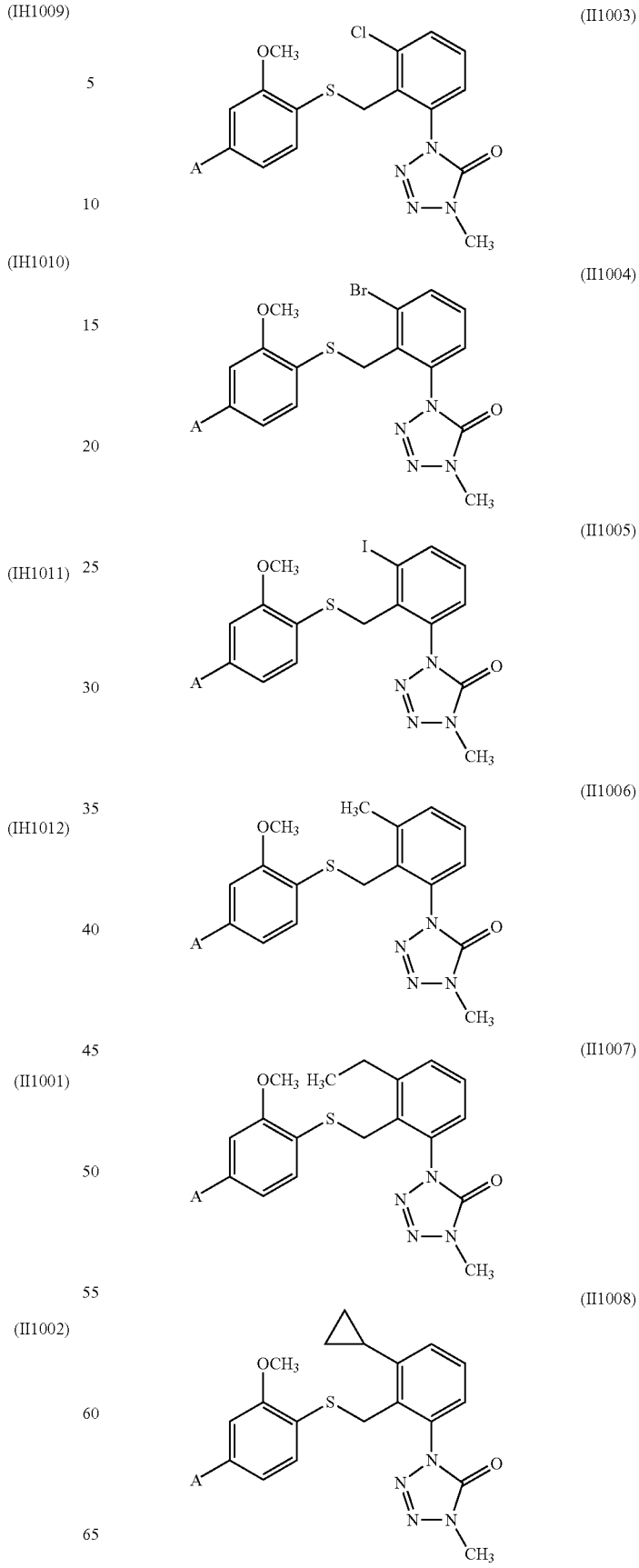

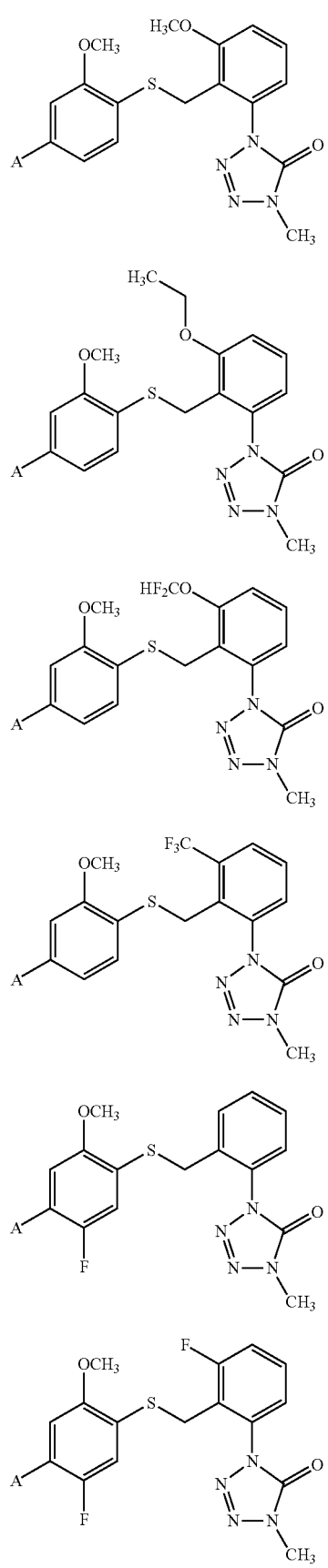
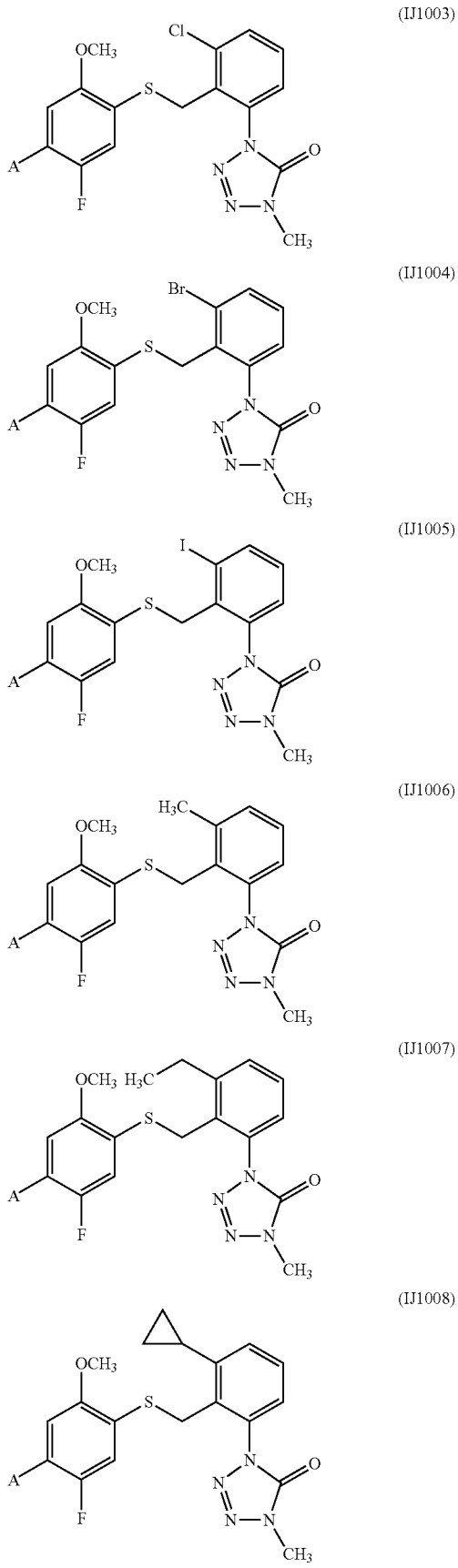

-continued (IJ1009) (IK1003)
(IJ1010) (IK1004)
(IJ1011) (IK1005)
(IJ1012) (IK1006)
(IK1001) (IK1007)
(IK1002) (IK1008)

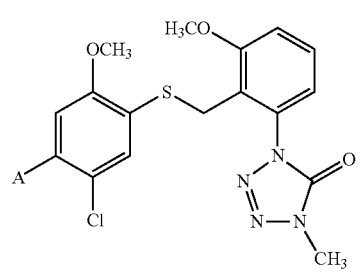
(IK1009)
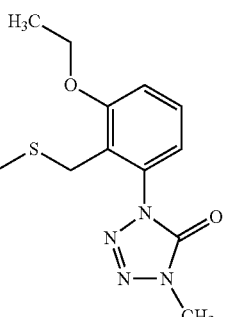
(IK1010)
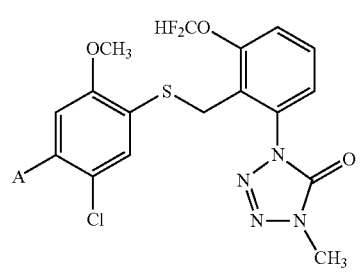
(IK1011)
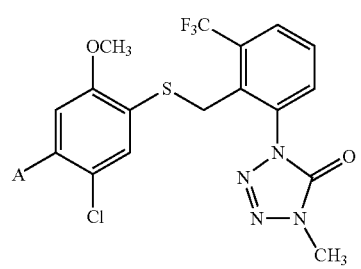
(IK1012)
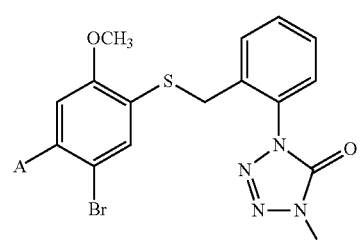
(IL1001)
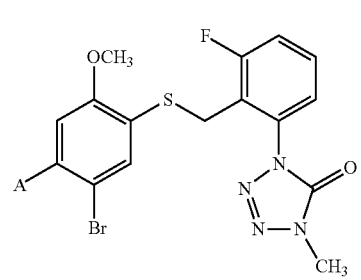
(IL1002)
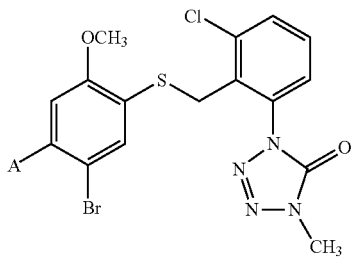
(IL1003)
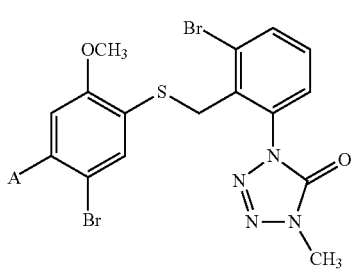
(IL1004)
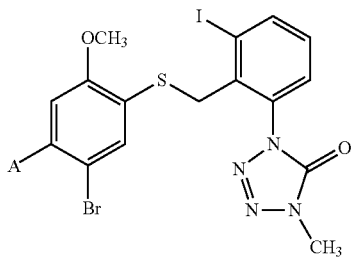
(IL1005)
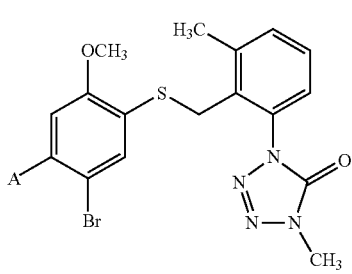
(IL1006)
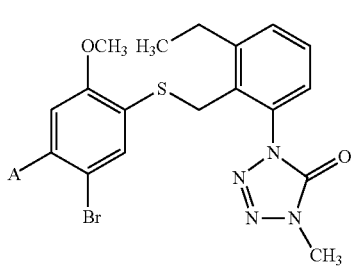
(IL1007)
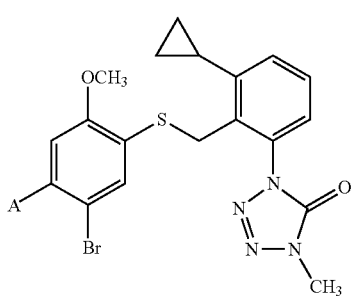
(IL1008)

(IL1009)
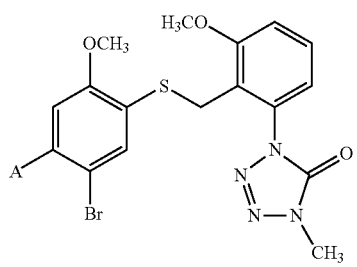
(IL1010)
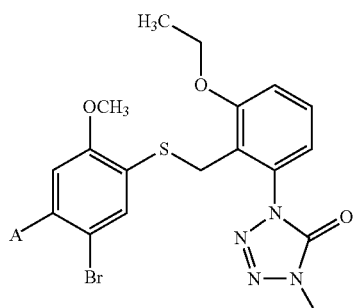
(IL1011)
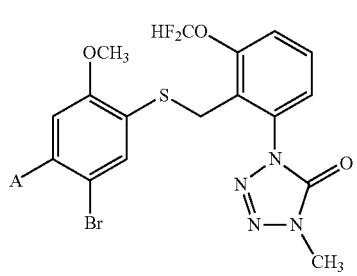
(IL1012)
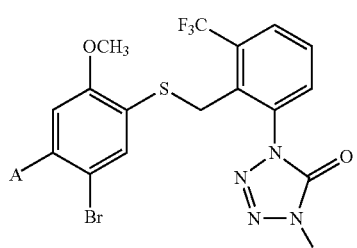
(IM1001)
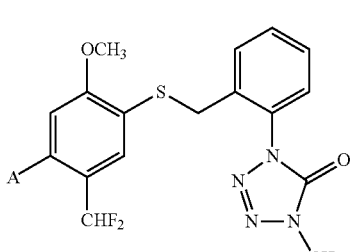
(IM1002)
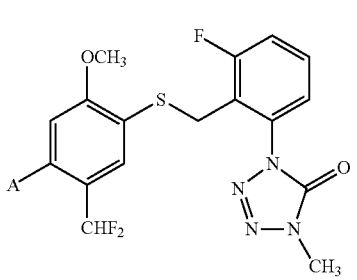
(IM1003)
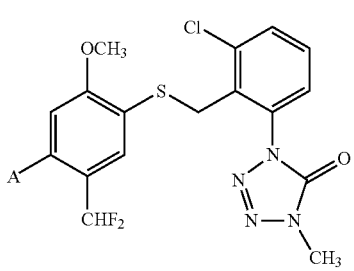
(IM1004)
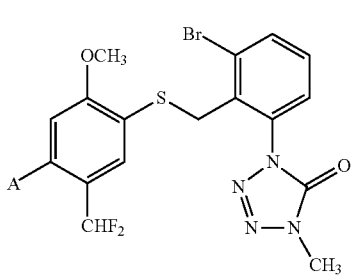
(IM1005)
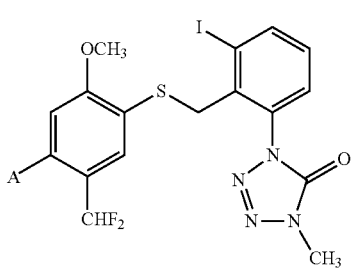
(IM1006)
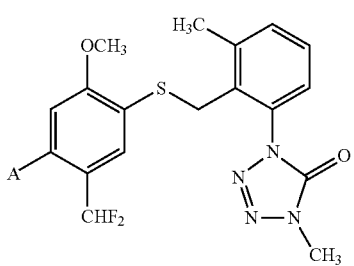
(IM1007)
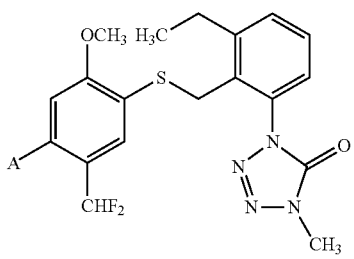
(IM1008)
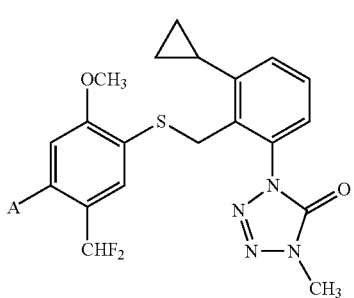

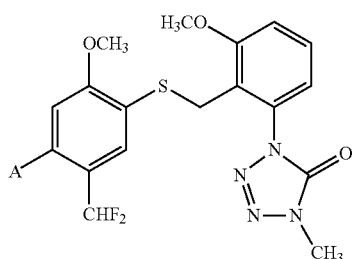
(IM1009)
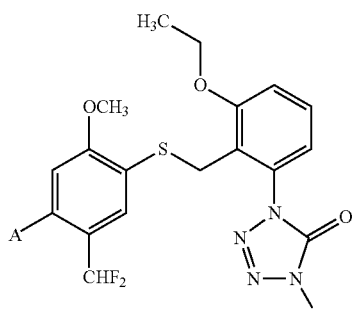
(IM1010)
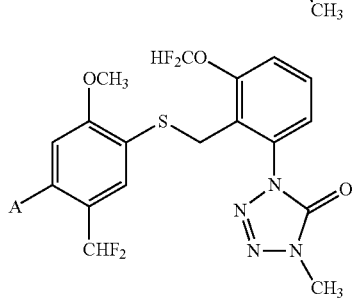
(IM1011)
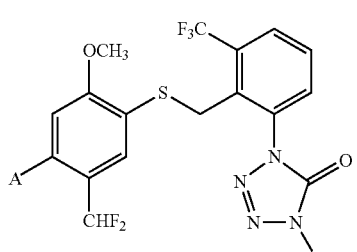
(IM1012)
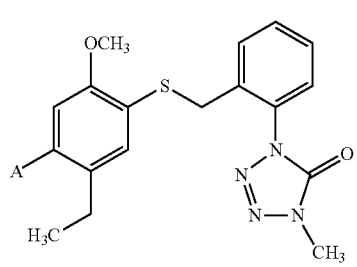
(IN1001)
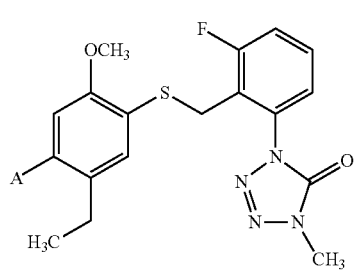
(IN1002)
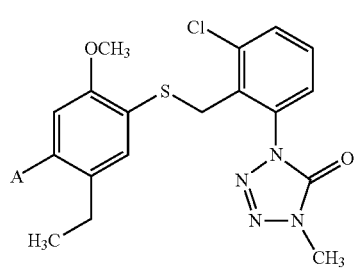
(IN1003)
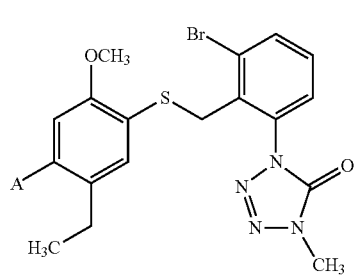
(IN1004)
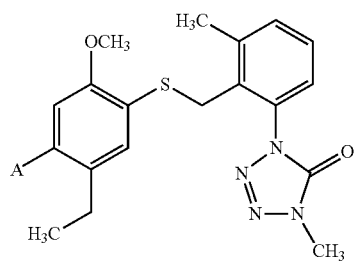
(IN1005)
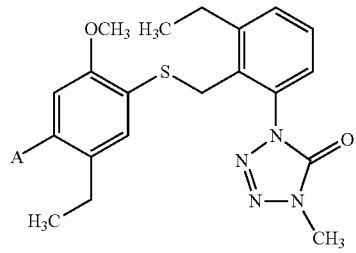
(IN1006)
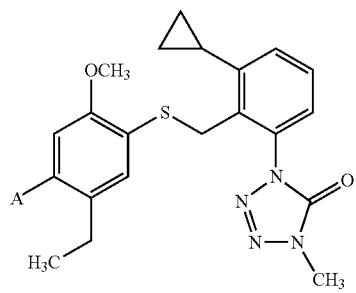
(IN1007)
(IN1008)

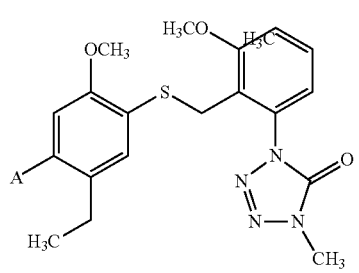
(IN1009)
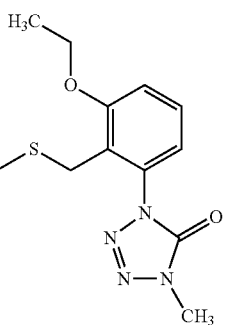
(IN1010)
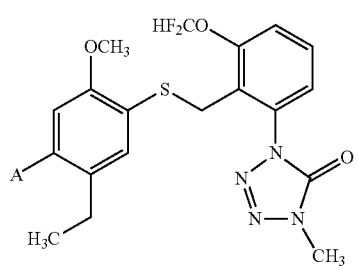
(IN1011)
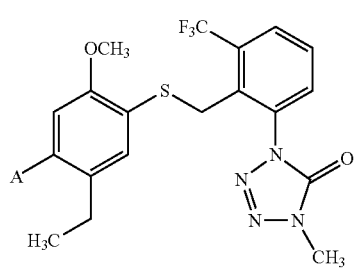
(IN1012)
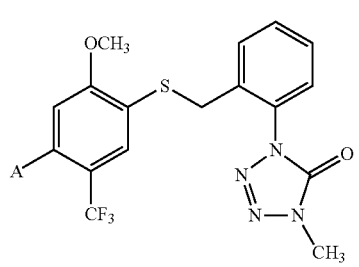
(IO1001)
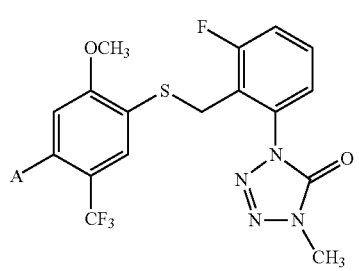
(IO1002)
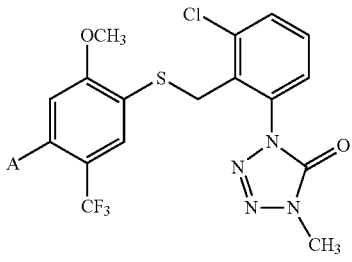
(IO1003)
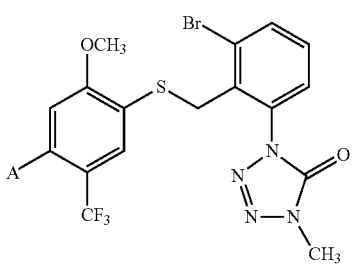
(IO1004)
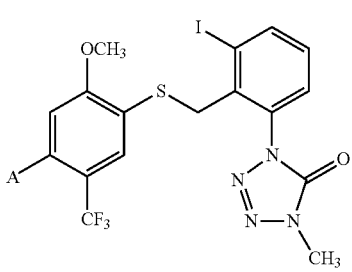
(IO1005)
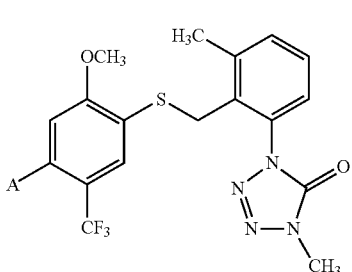
(IO1006)
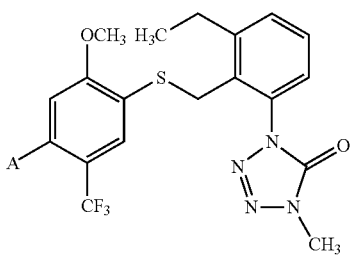
(IO1007)
(IO1008)

-continued

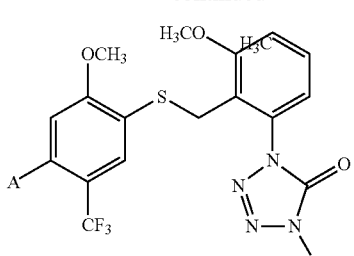
(IO1009)

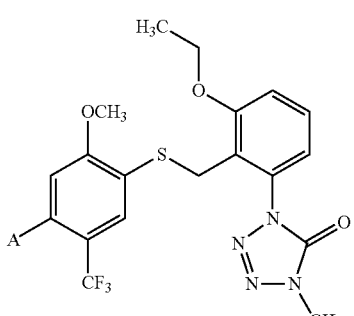
(IO1010)

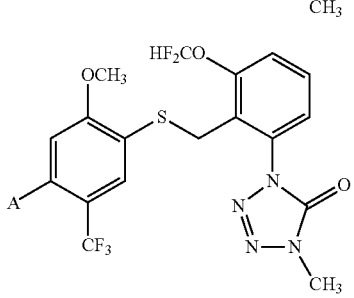
(IO1011)

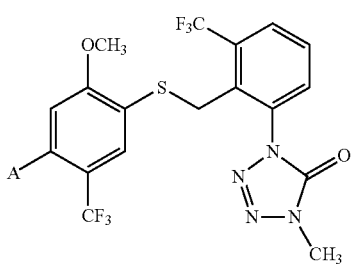
(IO1012)

[substituent number; A]: [1; 1bb, G1=H, G2=H, G3=H, G4=H], [2; 1bb, G1=Me, G2=H, G3=H, G4=H], [3; 1bb, G1=H, G2=Me, G3=H, G4=H], [4; 1bb, G1=H, G2=H, G3=Me, G4=H], [5; 1bb, G1=H, G2=H, G3=H, G4=Me], [6; 1bb, G1=Me, G2=Me, G3=H, G4=H], [7; 1bb, G1=Me, G2=H, G3=Me, G4=H], [8; 1bb, G1=Me, G2=H, G3=H, G4=Me], [9; 1bb, G1=H, G2=Me, G3=Me, G4=H], [10; 1bb, G1=H, G2=Me, G3=H, G4=Me], [11; 1bb, G1=H, G2=H, G3=Me, G4=Me], [12; 1bb, G1=H, G2=Me, G3=H, G4=H], [13; 1bb, G1=Me, G2=Me, G3=Me, G4=H], [14; 1bb, G1=Me, G2=Me, G3=H, G4=Me], [15; 1bb, G1=Me, G2=H, G3=Me, G4=Me], [16; 1bb, G1=H, G2=Me, G3=Me, G4=Me], [17; 1bb, G1=Me, G2=Me, G3=Me, G4=Me], [18; 1bb, G1=Me, G2=F, G3=H, G4=H], [19; 1bb, G1=Me, G2=H, G3=F, G4=H], [20; 1bb, G1=Me, G2=H, G3=H, G4=F], [21; 1bb, G1=Me, G2=F, G3=F, G4=H], [22; 1bb, G1=Me, G2=F, G3=H, G4=F], [23; 1bb, G1=Me, G2=H, G3=F, G4=F], [24; 1bb, G1=Me, G2=F, G3=F, G4=F], [25; 1bb, G1=F, G2=Me, G3=H, G4=H], [26; 1bb, G1=H, G2=Me, G3=F, G4=H], [27; 1bb, G1=H, G2=Me, G3=H, G4=F], [28; 1bb, G1=F, G2=Me, G3=F, G4=H], [29; 1bb, G1=F, G2=Me, G3=H, G4=F], [30; 1bb, G1=H, G2=Me, G3=F, G4=F], [31; 1bb, G1=F, G2=Me, G3=F, G4=F], [32; 1bb, G1=F, G2=H, G3=Me, G4=H], [33; 1bb, G1=H, G2=F, G3=Me, G4=H], [34; 1bb, G1=H, G2=H, G3=Me, G4=F], [35; 1bb, G1=F, G2=F, G3=Me, G4=H], [36; 1bb, G1=F, G2=H, G3=Me, G4=F], [37; 1bb, G1=H, G2=F, G3=Me, G4=F], [38; 1bb, G1=F, G2=F, G3=Me, G4=F], [39; 1bb, G1=F, G2=H, G3=H, G4=Me], [40; 1bb, G1=H, G2=F, G3=H, G4=Me], [41; 1bb, G1=H, G2=H, G3=F, G4=Me], [42; 1bb, G1=F, G2=F, G3=H, G4=Me], [43; 1bb, G1=F, G2=H, G3=F, G4=Me], [44; 1bb, G1=H, G2=F, G3=F, G4=Me], [45; 1bb, G1=F, G2=F, G3=F, G4=Me], [46; 1bb, G1=Me, G2=Me, G3=F, G4=H], [47; 1bb, G1=Me, G2=Me, G3=H, G4=F], [48; 1bb, G1=Me, G2=F, G3=Me, G4=H], [49; 1bb, G1=Me, G2=H, G3=Me, G4=F], [50; 1bb, G1=Me, G2=F, G3=H, G4=Me], [51; 1bb, G1=Me, G2=H, G3=F, G4=Me], [52; 1bb, G1=Me, G2=Me, G3=Cl, G4=H], [53; 1bb, G1=Me, G2=Me, G3=H, G4=Cl], [54; 1bb, G1=Me, G2=Cl, G3=Me, G4=H], [55; 1bb, G1=Me, G2=H, G3=Me, G4=Cl], [56; 1bb, G1=Me, G2=Cl, G3=H, G4=Me], [57; 1bb, G1=Me, G2=H, G3=Cl, G4=Me], [58; 1bb, G1=Me, G2=H, G3=Cl, G4=H], [59; 1bb, G1=Me, G2=H, G3=Cl, G4=H], [60; 1bb, G1=Me, G2=H, G3=H, G4=Cl], [61; 1bb, G1=Me, G2=Cl, G3=Cl, G4=H], [62; 1bb, G1=Me, G2=Cl, G3=H, G4=Cl], [63; 1bb, G1=Me, G2=H, G3=Cl, G4=Cl], [64; 1bb, G1=Cl, G2=Me, G3=H, G4=H], [65; 1bb, G1=H, G2=Me, G3=Cl, G4=H], [66; 1bb, G1=H, G2=Me, G3=H, G4=Cl], [67; 1bb, G1=Cl, G2=Me, G3=Cl, G4=H], [68; 1bb, G1=Cl, G2=Me, G3=H, G4=Cl], [69; 1bb, G1=H, G2=Me, G3=Cl, G4=Cl], [70; 1bb, G1=Cl, G2=H, G3=Me, G4=H], [71; 1bb, G1=H, G2=Cl, G3=Me, G4=H], [72; 1bb, G1=H, G2=H, G3=Me, G4=Cl], [73; 1bb, G1=Cl, G2=Cl, G3=Me, G4=H], [74; 1bb, G1=Cl, G2=H, G3=Me, G4=Cl], [75; 1bb, G1=H, G2=Cl, G3=Me, G4=Cl], [76; 1bb, G1=Cl, G2=H, G3=H, G4=Me], [77; 1bb, G1=H, G2=Cl, G3=H, G4=Me], [78; 1bb, G1=H, G2=H, G3=Cl, G4=Me], [79; 1bb, G1=Cl, G2=Cl, G3=H, G4=Me], [80; 1bb, G1=Cl, G2=H, G3=Cl, G4=Me], [81; 1bb, G1=H, G2=Cl, G3=Cl, G4=Me], [82; 1bb, G1=Me, G2=Br, G3=H, G4=H], [83; 1bb, G1=Me, G2=H, G3=Br, G4=H], [84; 1bb, G1=Me, G2=H, G3=H, G4=Br], [85; 1bb, G1=Br, G2=Me, G3=H, G4=H], [86; 1bb, G1=H, G2=Me, G3=Br, G4=H], [87; 1bb, G1=H, G2=Me, G3=H, G4=Br], [88; 1bb, G1=Br, G2=H, G3=Me, G4=H], [89; 1bb, G1=H, G2=Br, G3=Me, G4=H], [90; 1bb, G1=H, G2=H, G3=Me, G4=Br], [91; 1bb, G1=Br, G2=H, G3=H, G4=Me], [92; 1bb, G1=H, G2=Br, G3=H, G4=Me], [93; 1bb, G1=H, G2=H, G3=Br, G4=Me], [94; 1bb, G1=Me, G2=Me, G3=Br, G4=H], [95; 1bb, G1=Me, G2=Me, G3=H, G4=Br], [96; 1bb, G1=Me, G2=Br, G3=Me, G4=H], [97; 1bb, G1=Me, G2=H, G3=Me, G4=Br], [98; 1bb, G1=Me, G2=Br, G3=H, G4=Me], [99; 1bb, G1=Me, G2=H, G3=Br, G4=Me], [100; 1bb, G1=Me, G2=CN, G3=H, G4=H], [101; 1bb, G1=Me, G2=H, G3=CN, G4=H], [102; 1bb, G1=Me, G2=H, G3=H, G4=CN], [103; 1bb, G1=CN, G2=Me, G3=H, G4=H], [104; 1bb, G1=H, G2=Me, G3=CN, G4=H], [105; 1bb, G1=H, G2=Me, G3=H, G4=CN], [106; 1bb, G1=CN, G2=H, G3=Me, G4=H], [107; 1bb, G1=H, G2=CN, G3=Me, G4=H], [108; 1bb, G1=H, G2=H, G3=Me, G4=CN], [109; 1bb, G1=CN, G2=H, G3=H, G4=Me], [110; 1bb, G1=H, G2=CN, G3=H, G4=Me], [111; 1bb, G1=H, G2=H, G3=CN, G4=Me], [112; 1bb, G1=Me, G2=H, G3=CN, G4=CN], [113; 1bb, G1=Me, G2=Me, G3=H, G4=CN], [114; 1bb, G1=Me, G2=CN, G3=Me, G4=H], [115; 1bb, G1=Me, G2=H, G3=Me, G4=CN], [116; 1bb, G1=Me, G2=CN, G3=H, G4=Me],

[117; 1bb, G1=Me, G2=H, G3=CN, G4=Me], [118; 1bb, G1=Me, G2=OMe, G3=H, G4=H], [119; 1bb, G1=Me, G2=H, G3=OMe, G4=H], [120; 1bb, G1=Me, G2=H, G3=H, G4=OMe], [121; 1bb, G1=OMe, G2=Me, G3=H, G4=H], [122; 1bb, G1=H, G2=Me, G3=OMe, G4=H], [123; 1bb, G1=H, G2=Me, G3=H, G4=OMe], [124; 1bb, G1=OMe, G2=H, G3=Me, G4=H], [125; 1bb, G1=H, G2=OMe, G3=Me, G4=H], [126; 1bb, G1=H, G2=H, G3=Me, G4=OMe], [127; 1bb, G1=OMe, G2=H, G3=H, G4=Me], [128; 1bb, G1=H, G2=OMe, G3=H, G4=Me], [129; 1bb, G1=H, G2=H, G3=OMe, G4=Me], [130; 1bb, G1=Me, G2=Me, G3=OMe, G4=H], [131; 1bb, G1=Me, G2=Me, G3=H, G4=OMe], [132; 1bb, G1=Me, G2=OMe, G3=Me, G4=H], [133; 1bb, G1=Me, G2=H, G3=Me, G4=OMe], [134; 1bb, G1=Me, G2=OMe, G3=H, G4=Me], [135; 1bb, G1=Me, G2=H, G3=OMe, G4=Me], [136; 1bb, G1=Me, G2=OEt, G3=H, G4=H], [137; 1bb, G1=Me, G2=H, G3=OEt, G4=H], [138; 1bb, G1=Me, G2=H, G3=H, G4=OEt], [139; 1bb, G1=OEt, G2=Me, G3=H, G4=H], [140; 1bb, G1=H, G2=Me, G3=OEt, G4=H], [141; 1bb, G1=H, G2=Me, G3=H, G4=OEt], [142; 1bb, G1=OEt, G2=H, G3=Me, G4=H], [143; 1bb, G1=H, G2=OEt, G3=Me, G4=H], [144; 1bb, G1=H, G2=H, G3=Me, G4=OEt], [145; 1bb, G1=OEt, G2=H, G3=H, G4=Me], [146; 1bb, G1=H, G2=OEt, G3=H, G4=Me], [147; 1bb, G1=H, G2=H, G3=OEt, G4=Me], [148; 1bb, G1=Me, G2=Me, G3=OEt, G4=H], [149; 1bb, G1=Me, G2=Me, G3=H, G4=OEt], [150; 1bb, G1=Me, G2=OEt, G3=Me, G4=H], [151; 1bb, G1=Me, G2=H, G3=Me, G4=OEt], [152; 1bb, G1=Me, G2=OEt, G3=H, G4=Me], [153; 1bb, G1=Me, G2=H, G3=OEt, G4=Me], [154; 1bb, G1=Me, G2=Et, G3=H, G4=H], [155; 1bb, G1=Me, G2=H, G3=Et, G4=H], [156; 1bb, G1=Me, G2=H, G3=H, G4=Et], [157; 1bb, G1=Et, G2=Me, G3=H, G4=H], [158; 1bb, G1=H, G2=Me, G3=Et, G4=H], [159; 1bb, G1=H, G2=Me, G3=H, G4=Et], [160; 1bb, G1=Et, G2=H, G3=Me, G4=H], [161; 1bb, G1=H, G2=Et, G3=Me, G4=H], [162; 1bb, G1=H, G2=H, G3=Me, G4=Et], [163; 1bb, G1=Et, G2=H, G3=H, G4=Me], [164; 1bb, G1=H, G2=Et, G3=H, G4=Me], [165; 1bb, G1=H, G2=H, G3=Et, G4=Me], [166; 1bb, G1=Me, G2=Me, G3=Et, G4=H], [167; 1bb, G1=Me, G2=Me, G3=H, G4=Et], [168; 1bb, G1=Me, G2=Et, G3=Me, G4=H], [169; 1bb, G1=Me, G2=H, G3=Me, G4=Et], [170; 1bb, G1=Me, G2=Et, G3=H, G4=Me], [171; 1bb, G1=Me, G2=H, G3=Et, G4=Me], [172; 1bb, G1=Me, G2=CF$_3$, G3=H, G4=H], [173; 1bb, G1=Me, G2=H, G3=CF$_3$, G4=H], [174; 1bb, G1=Me, G2=H, G3=H, G4=CF$_3$], [175; 1bb, G1=CF$_3$, G2=Me, G3=H, G4=H], [176; 1bb, G1=H, G2=Me, G3=CF$_3$, G4=H], [177; 1bb, G1=H, G2=Me, G3=H, G4=CF$_3$], [178; 1bb, G1=CF$_3$, G2=H, G3=Me, G4=H], [179; 1bb, G1=H, G2=CF$_3$, G3=Me, G4=H], [180; 1bb, G1=H, G2=H, G3=Me, G4=CF$_3$], [181; 1bb, G1=CF$_3$, G2=H, G3=H, G4=Me], [182; 1bb, G1=CF$_3$, G2=H, G4=Me], [183; 1bb, G1=H, G2=H, G3=CF$_3$, G4=Me], [184; 1bb, G1=Et, G2=H, G3=H, G4=H], [185; 1bb, G1=H, G2=Et, G3=H, G4=H], [186; 1bb, G1=H, G2=H, G3=Et, G4=H], [187; 1bb, G1=H, G2=H, G3=H, G4=Et], [188; 1bb, G1=Et, G2=Et, G3=H, G4=H], [189; 1bb, G1=Et, G2=H, G3=Et, G4=H], [190; 1bb, G1=Et, G2=H, G3=H, G4=Et], [191; 1bb, G1=H, G2=Et, G3=Et, G4=H], [192; 1bb, G1=H, G2=Et, G3=H, G4=Et], [193; 1bb, G1=H, G2=Et, G4=Et], [194; 1bb, G1=Et, G2=Et, G3=Et, G4=H], [195; 1bb, G1=Et, G2=Et, G3=H, G4=Et], [196; 1bb, G1=Et, G2=F, G3=H, G4=H], [197; 1bb, G1=Et, G2=H, G3=F, G4=H], [198; 1bb, G1=Et, G2=H, G3=H, G4=F], [199; 1bb, G1=Et, G2=F, G3=F, G4=H], [200; 1bb, G1=Et, G2=F, G3=H, G4=F],

[201; 1bb, G1=Et, G2=H, G3=F, G4=F], [202; 1bb, G1=F, G2=Et, G3=H, G4=H], [203; 1bb, G1=H, G2=Et, G3=F, G4=H], [204; 1bb, G1=H, G2=Et, G3=H, G4=F], [205; 1bb, G1=F, G2=Et, G3=F, G4=H], [206; 1bb, G1=F, G2=Et, G3=H, G4=F], [207; 1bb, G1=H, G2=Et, G3=F, G4=F], [208; 1bb, G1=F, G2=H, G3=Et, G4=H], [209; 1bb, G1=H, G2=F, G3=Et, G4=H], [210; 1bb, G1=H, G2=H, G3=Et, G4=F], [211; 1bb, G1=F, G2=F, G3=Et, G4=H], [212; 1bb, G1=F, G2=H, G3=Et, G4=F], [213; 1bb, G1=H, G2=F, G3=Et, G4=F], [214; 1bb, G1=F, G2=H, G3=H, G4=Et], [215; 1bb, G1=H, G2=F, G3=H, G4=Et], [216; 1bb, G1=H, G2=H, G3=F, G4=Et], [217; 1bb, G1=F, G2=F, G3=H, G4=Et], [218; 1bb, G1=F, G2=H, G3=F, G4=Et], [219; 1bb, G1=H, G2=F, G3=F, G4=Et], [220; 1bb, G1=Et, G2=Et, G3=F, G4=H], [221; 1bb, G1=Et, G2=Et, G3=H, G4=F], [222; 1bb, G1=Et, G2=F, G3=Et, G4=H], [223; 1bb, G1=Et, G2=H, G3=Et, G4=F], [224; 1bb, G1=Et, G2=F, G3=H, G4=Et], [225; 1bb, G1=Et, G2=Et, G3=Cl, G4=H], [226; 1bb, G1=Et, G2=Et, G3=H, G4=Cl], [227; 1bb, G1=Et, G2=Cl, G3=Et, G4=H], [228; 1bb, G1=Et, G2=H, G3=Et, G4=Cl], [229; 1bb, G1=Et, G2=Cl, G3=H, G4=Et], [230; 1bb, G1=Et, G2=H, G3=Cl, G4=Et], [231; 1bb, G1=Et, G2=Cl, G3=H, G4=H], [232; 1bb, G1=Et, G2=H, G3=Cl, G4=H], [233; 1bb, G1=Et, G2=H, G3=H, G4=Cl], [234; 1bb, G1=Et, G2=Cl, G3=Cl, G4=H], [235; 1bb, G1=Et, G2=Cl, G3=H, G4=Cl], [236; 1bb, G1=Et, G2=H, G3=Cl, G4=Cl], [237; 1bb, G1=Cl, G2=Et, G3=H, G4=H], [238; 1bb, G1=H, G2=Et, G3=Cl, G4=H], [239; 1bb, G1=H, G2=Et, G3=H, G4=Cl], [240; 1bb, G1=Cl, G2=Et, G3=Cl, G4=H], [241; 1bb, G1=Cl, G2=Et, G3=H, G4=Cl], [242; 1bb, G1=H, G2=Et, G3=Cl, G4=Cl], [243; 1bb, G1=Cl, G2=H, G3=Et, G4=H], [244; 1bb, G1=H, G2=Cl, G3=Et, G4=H], [245; 1bb, G1=H, G2=H, G3=Et, G4=Cl], [246; 1bb, G1=Cl, G2=Cl, G3=Et, G4=H], [247; 1bb, G1=Cl, G2=H, G3=Et, G4=Cl], [248; 1bb, G1=H, G2=Cl, G3=Et, G4=Cl], [249; 1bb, G1=Cl, G2=H, G3=H, G4=Et], [250; 1bb, G1=H, G2=Cl, G3=H, G4=Et], [251; 1bb, G1=H, G2=H, G3=Cl, G4=Et], [252; 1bb, G1=Cl, G2=Cl, G3=H, G4=Et], [253; 1bb, G1=Cl, G2=H, G3=Cl, G4=Et], [254; 1bb, G1=H, G2=Cl, G3=Cl, G4=Et], [255; 1bb, G1=Et, G2=CN, G3=H, G4=H], [256; 1bb, G1=Et, G2=H, G3=CN, G4=H], [257; 1bb, G1=Et, G2=H, G3=H, G4=CN], [258; 1bb, G1=CN, G2=Et, G3=H, G4=H], [259; 1bb, G1=H, G2=Et, G3=CN, G4=H], [260; 1bb, G1=H, G2=Et, G3=CN, G4=H], [260; 1bb, G1=H, G2=Et, G3=H, G4=CN], [261; 1bb, G1=CN, G2=H, G3=Et, G4=H], [262; 1bb, G1=H, G2=CN, G3=Et, G4=H], [263; 1bb, G1=H, G2=H, G3=Et, G4=CN], [264; 1bb, G1=CN, G2=H, G3=H, G4=Et], [265; 1bb, G1=H, G2=CN, G3=H, G4=Et], [266; 1bb, G1=H, G2=H, G3=CN, G4=Et], [267; 1bb, G1=Et, G2=CF$_3$, G3=H, G4=H], [268; 1bb, G1=Et, G2=H, G3=CF$_3$, G4=H], [269; 1bb, G1=Et, G2=H, G3=H, G4=CF$_3$], [270; 1bb, G1=CF$_3$, G2=Et, G3=H, G4=H], [271; 1bb, G1=H, G2=Et, G3=CF$_3$, G4=H], [272; 1bb, G1=H, G2=Et, G3=H, G4=CF$_3$], [273; 1bb, G1=CF$_3$, G2=H, G3=Et, G4=H], [274; 1bb, G1=H, G2=CF$_3$, G3=Et, G4=H], [275; 1bb, G1=H, G2=H, G3=Et, G4=CF$_3$], [276; 1bb, G1=CF$_3$, G2=H, G3=H, G4=Et], [277; 1bb, G1=H, G2=CF$_3$, G3=H, G4=Et], [278; 1bb, G1=H, G2=H, G3=CF$_3$, G4=Et], [279; 1bb, G1=Et, G2=OMe, G3=H, G4=H], [280; 1bb, G1=Et, G2=H, G3=OMe, G4=H], [281; 1bb, G1=Et, G2=H, G3=H, G4=OMe], [282; 1bb, G1=OMe, G2=Et, G3=H, G4=H], [283; 1bb, G1=H, G2=Et, G3=OMe, G4=H], [284; 1bb, G1=H, G2=Et, G3=H, G4=OMe], [285; 1bb, G1=OMe, G2=H, G3=Et, G4=H], [286; 1bb, G1=H, G2=OMe, G3=Et, G4=H], [287; 1bb, G1=H, G2=H, G3=Et, G4=OMe], [288; 1bb, G1=OMe, G2=H, G3=H, G4=Et], [289; 1bb, G1=H, G2=OMe, G3=H, G4=Et], [290; 1bb,

G1=H, G2=H, G3=OMe, G4=Et], [291; 1bb, G1=F, G2=H, G3=H, G4=H], [292; 1bb, G1=H, G2=F, G3=H, G4=H], [293; 1bb, G1=H, G2=H, G3=F, G4=H], [294; 1bb, G1=H, G2=H, G3=H, G4=F], [295; 1bb, G1=F, G2=F, G3=H, G4=H], [296; 1bb, G1=F, G2=H, G3=F, G4=H], [297; 1bb, G1=F, G2=H, G3=H, G4=F], [298; 1bb, G1=H, G2=F, G3=F, G4=H], [299; 1bb, G1=H, G2=F, G3=H, G4=F], [300; 1bb, G1=H, G2=H, G3=F, G4=F],

[301; 1bb, G1=F, G2=F, G3=F, G4=H], [302; 1bb, G1=F, G2=H, G3=F, G4=F], [303; 1bb, G1=F, G2=F, G3=H, G4=F], [304; 1bb, G1=Cl, G2=H, G3=H, G4=H], [305; 1bb, G1=H, G2=Cl, G3=H, G4=H], [306; 1bb, G1=H, G2=H, G3=Cl, G4=H], [307; 1bb, G1=H, G2=H, G3=H, G4=Cl], [308; 1bb, G1=Cl, G2=Cl, G3=H, G4=H], [309; 1bb, G1=Cl, G2=H, G3=Cl, G4=H], [310; 1bb, G1=Cl, G2=H, G3=H, G4=Cl], [311; 1bb, G1=H, G2=Cl, G3=Cl, G4=H], [312; 1bb, G1=H, G2=Cl, G3=H, G4=Cl], [313; 1bb, G1=H, G2=H, G3=Cl, G4=Cl], [314; 1bb, G1=Cl, G2=H, G3=Cl, G4=Cl], [315; 1bb, G1=Cl, G2=Cl, G3=H, G4=Cl], [316; 1bb, G1=Cl, G2=Cl, G3=Cl, G4=H], [317; 1bb, G1=F, G2=Cl, G3=H, G4=H], [318; 1bb, G1=F, G2=H, G3=Cl, G4=H], [319; 1bb, G1=F, G2=H, G3=H, G4=Cl], [320; 1bb, G1=Cl, G2=F, G3=H, G4=H], [321; 1bb, G1=H, G2=F, G3=Cl, G4=H], [322; 1bb, G1=H, G2=F, G3=H, G4=Cl], [323; 1bb, G1=Cl, G2=H, G3=F, G4=H], [324; 1bb, G1=H, G2=Cl, G3=F, G4=H], [325; 1bb, G1=H, G2=H, G3=F, G4=Cl], [326; 1bb, G1=Cl, G2=H, G3=H, G4=F], [327; 1bb, G1=H, G2=Cl, G3=H, G4=F], [328; 1bb, G1=H, G2=H, G3=Cl, G4=F], [329; 1bb, G1=n-propyl, G2=H, G3=H, G4=H], [330; 1bb, G1=H, G2=n-propyl, G3=H, G4=H], [331; 1bb, G1=H, G2=H, G3=n-propyl, G4=H], [332; 1bb, G1=H, G2=H, G3=H, G4=n-propyl], [333; 1bb, G1=isopropyl, G2=H, G3=H, G4=H], [334; 1bb, G1=H, G2=isopropyl, G3=H, G4=H], [335; 1bb, G1=H, G2=H, G3=isopropyl, G4=H], [336; 1bb, G1=H, G2=H, G3=H, G4=isopropyl], [337; 1bb, G1=OMe, G2=H, G3=H, G4=H], [338; 1bb, G1=H, G2=H, G3=H, G4=OMe], [339; 1bb, G1=OMe, G2=H, G3=H, G4=H], [340; 1bb, G1=OMe, G2=H, G3=H, G4=H], [341; 1bb, G1=H, G2=OMe, G3=H, G4=H], [342; 1bb, G1=H, G2=H, G3=OMe, G4=H], [343; 1bb, G1=H, G2=H, G3=H, G4=OMe], [344; 1bb, G1=OMe, G2=F, G3=H, G4=H], [345; 1bb, G1=OMe, G2=H, G3=F, G4=H], [346; 1bb, G1=OMe, G2=H, G3=H, G4=F], [347; 1bb, G1=F, G2=OMe, G3=H, G4=H], [348; 1bb, G1=H, G2=OMe, G3=F, G4=H], [349; 1bb, G1=H, G2=OMe, G3=H, G4=F], [350; 1bb, G1=F, G2=H, G3=OMe, G4=H], [351; 1bb, G1=H, G2=F, G3=OMe, G4=H], [352; 1bb, G1=H, G2=H, G3=OMe, G4=F], [353; 1bb, G1=F, G2=H, G3=H, G4=OMe], [354; 1bb, G1=H, G2=F, G3=H, G4=OMe], [355; 1bb, G1=H, G2=H, G3=F, G4=OMe], [356; 1bb, G1=OMe, G2=Cl, G3=H, G4=H], [357; 1bb, G1=OMe, G2=H, G3=Cl, G4=H], [358; 1bb, G1=OMe, G2=H, G3=H, G4=Cl], [359; 1bb, G1=Cl, G2=OMe, G3=H, G4=H], [360; 1bb, G1=H, G2=OMe, G3=Cl, G4=H], [361; 1bb, G1=H, G2=OMe, G3=H, G4=Cl], [362; 1bb, G1=Cl, G2=H, G3=OMe, G4=H], [363; 1bb, G1=H, G2=Cl, G3=OMe, G4=H], [364; 1bb, G1=H, G2=H, G3=OMe, G4=Cl], [365; 1bb, G1=Cl, G2=H, G3=H, G4=OMe], [366; 1bb, G1=H, G2=Cl, G3=H, G4=OMe], [367; 1bb, G1=H, G2=H, G3=Cl, G4=OMe], [368; 1bb, G1=CN, G2=H, G3=H, G4=H], [369; 1bb, G1=H, G2=CN, G3=H, G4=H], [370; 1bb, G1=H, G2=H, G3=CN, G4=H], [371; 1bb, G1=H, G2=H, G3=H, G4=CN], [372; 1bb, G1=CN, G2=F, G3=H, G4=H], [373; 1bb, G1=CN, G2=H, G3=F, G4=H], [374; 1bb, G1=CN, G2=H, G3=H, G4=F], [375; 1bb, G1=F, G2=CN, G3=H, G4=H], [376; 1bb, G1=H, G2=CN, G3=F, G4=H], [377; 1bb, G1=H, G2=CN, G3=H, G4=F], [378; 1bb, G1=F, G2=H, G3=CN, G4=H], [379; 1bb, G1=H, G2=F, G3=CN, G4=H], [380; 1bb, G1=H, G2=H, G3=CN, G4=F], [381; 1bb, G1=F, G2=H, G3=H, G4=CN], [382; 1bb, G1=H, G2=F, G3=H, G4=CN], [383; 1bb, G1=H, G2=H, G3=F, G4=CN], [384; 1bb, G1=CN, G2=Cl, G3=H, G4=H], [385; 1bb, G1=CN, G2=H, G3=Cl, G4=H], [386; 1bb, G1=CN, G2=H, G3=H, G4=Cl], [387; 1bb, G1=Cl, G2=CN, G3=H, G4=H], [388; 1bb, G1=H, G2=CN, G3=Cl, G4=H], [389; 1bb, G1=H, G2=CN, G3=H, G4=Cl], [390; 1bb, G1=Cl, G2=H, G3=CN, G4=H], [391; 1bb, G1=H, G2=Cl, G3=CN, G4=H], [392; 1bb, G1=H, G2=H, G3=CN, G4=Cl], [393; 1bb, G1=Cl, G2=H, G3=H, G4=CN], [394; 1bb, G1=H, G2=Cl, G3=H, G4=CN], [395; 1bb, G1=H, G2=H, G3=Cl, G4=CN], [396; 1aa, $E^1$=H, $E^2$=Me, $E^3$=H], [397; 1aa, $E^1$=H, $E^2$=H, $E^3$=Me], [398; 1aa, $E^1$=Et, $E^2$=H, $E^3$=H], [399; 1aa, $E^1$=H, $E^2$=Et, $E^3$=H], [400; 1aa, $E^1$=H, $E^2$=H, $E^3$=Et],

[401; 1aa, $E^1$=F, $E^2$=H, $E^3$=H], [402; 1aa, $E^1$=H, $E^2$=F, $E^3$=H], [403; 1aa, $E^1$=H, $E^2$=H, $E^3$=F], [404; 1aa, $E^1$=Cl, $E^2$=H, $E^3$=H], [405; 1aa, $E^1$=H, $E^2$=Cl, $E^3$=H], [406; 1aa, $E^1$=H, $E^2$=H, $E^3$=Cl], [407; 1aa, $E^1$=Br, $E^2$=H, $E^3$=H], [408; 1aa, $E^1$=H, $E^2$=Br, $E^3$=H], [409; 1aa, $E^1$=H, $E^2$=H, $E^3$=Br], [410; 1aa, $E^1$=CN, $E^2$=H, $E^3$=H], [411; 1aa, $E^1$=H, $E^2$=CN, $E^3$=H], [412; 1aa, $E^1$=H, $E^2$=H, $E^3$=CN], [413; 1aa, $E^1$=OMe, $E^2$=H, $E^3$=H], [414; 1aa, $E^1$=H, $E^2$=OMe, $E^3$=H], [415; 1aa, $E^1$=H, $E^2$=H, $E^3$=OMe], [416; 1aa, $E^1$=OEt, $E^2$=H, $E^3$=H], [417; 1aa, $E^1$=H, $E^2$=OEt, $E^3$=H], [418; 1aa, $E^1$=H, $E^2$=H, $E^3$=OEt], [419; 1aa, $E^1$=$CF_3$, $E^2$=H, $E^1$=H], [420; 1aa, $E^1$=H, $E^2$=$CF_3$, $E^3$=H], [421; 1aa, $E^1$=H, $E^2$=H, $E^3$=$CF_3$], [422; 1aa, $E^1$=$CHF_2$, $E^2$=H, $E^3$=H], [423; 1aa, $E^1$=H, $E^2$=$CHF_2$, $E^3$=H], [424; 1aa, $E^1$=H, $E^2$=H, $E^3$=$CHF_2$], [425; 1aa, $E^1$=Me, $E^2$=Me, $E^3$=H], [426; 1aa, $E^1$=Me, $E^2$=H, $E^3$=Me], [427; 1aa, $E^1$=Cl, $E^2$=Cl, $E^3$=H], [428; 1aa, $E^1$=Cl, $E^2$=H, $E^3$=Cl], [429; 1aa, $E^1$=H, $E^2$=Me, $E^3$=Me], [430; 1aa, $E^1$=H, $E^2$=Cl, $E^3$=Cl], [431; 1aa, $E^1$=OMe, $E^2$=H, $E^3$=Cl], [432; 1aa, $E^1$=OMe, $E^2$=H, $E^3$=CN], [433; 1aa, $E^1$=OMe, $E^2$=H, $E^3$=F], [434; 1aa, $E^1$=F, $E^2$=H, $E^3$=Cl], [435; 1aa, $E^1$=F, $E^2$=H, $E^3$=CN], [436; 1aa, $E^1$=F, $E^2$=H, $E^3$=F], [437; 1aa, $E^1$=H, $E^2$=H, $E^3$=H], [438; 1aa, $E^1$=Me, $E^2$=H, $E^3$=H]

Examples of the present control agent will be shown below.

Formulation Example 1

Fifty parts (50 parts) of any one of the present compounds A, 3 parts of calcium ligninsulfonate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds A and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds A, 88 parts of kaolin clay, and 10 parts of talc are thoroughly ground and mixed to obtain each formulation.

Formulation Example 4

Five parts (5 parts) of any one of the present compounds A, 14 parts of polyoxyethylene styryl phenyl ether, 6 parts of calcium dodecylbenzenesulfonate, and 75 parts of xylene are thoroughly mixed to obtain each formulation.

Formulation Example 5

Two parts (2 parts) of any one of the present compounds A, 1 part of synthetic hydrated silicon oxide, 2 parts of calcium ligninsulfonate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds A, 35 parts of white carbon containing 50 parts of a polyoxyethylene alkyl ether sulfate ammonium salt, and 55 parts of water are finely ground by a wet grinding method to obtain each formulation.

Next, Test Examples will be shown.

The control effect was evaluated by visually observing the area of lesion on each of test plants at the time of investigation, and comparing the area of lesion on a plant treated with the present compound with that on an untreated plant.

Test Example 1

Each of plastic pots was filled with soil and cucumber (cultivar: SAGAMI HANJIRO) was sowed and grown in a greenhouse for 12 days. Then, each water dilution prepared by adjusting so as to contain a predetermined concentration (500 ppm) of any one compound of the present compounds 1, 2, 3, 4, 5, 6, 7, 8, 9, and 11 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion was investigated. As a result, the area of lesion on the plant treated with the present compound 1, 2, 3, 4, 5, 6, 7, 8, 9, or 11 was 30% or less of that on an untreated plant.

Test Example 2

Each of plastic pots was filled with soil and barley (cultivar: NISHINOHOSHI) was sowed and grown in a greenhouse for 7 days. Then, each water dilution prepared by adjusting so as to contain a predetermined concentration (500 ppm) of any one compound of the present compounds 1, 2, 3, 4, 5, 7, 8, 9, 10, and 11 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with the present compound 1, 2, 3, 4, 5, 7, 8, 9, 10, or 11 was 30% or less of that on an untreated plant.

Test Example 3

Each of plastic pots was filled with soil and barley (cultivar: NISHINOHOSHI) was sowed and grown in a greenhouse for 7 days. Then, each water dilution prepared by adjusting so as to contain a predetermined concentration (200 ppm) of any one compound of the present compounds 1, 2, 3, 4, 5, 7, 8, 9, 10, and 11 was sprayed over stems and leaves of the barley so that it sufficiently adhered to the surface of the leaves of the barley. After spraying, the plant was air-dried. After 2 days, an aqueous suspension containing spores of barley leaf blotch fungus (*Rhynchosporium secalis*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with the present compound 1, 2, 3, 4, 5, 7, 8, 9, 10, or 11 was 30% or less of that on an untreated plant.

Test Example 4

Each of plastic pots was filled with soil and wheat (cultivar: APOGEE) was sowed and grown in a greenhouse for 10 days. Then, each water dilution prepared by adjusting so as to contain a predetermined concentration (200 ppm) of any one compound of the present compounds 1, 2, 3, 4, 5, 7, 8, 10, and 11 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed over the wheat to inoculate the spores. After completion of the inoculation, the plant was placed at 18° C. under high humidity condition for 3 days and then placed under illumination for 14 to 18 days, and then the area of lesion was investigated. As a result, the area of lesion on the plant treated with the present compound 1, 2, 3, 4, 5, 7, 8, 10, or 11 was 30% or less of that on an untreated plant.

Test Example 5

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of any one compound of the present compounds 1, 2, 3, 7, 8, 9, 10, and 11 was sprayed over stems and leaves of the cucumber so that it sufficiently adhered to the surface of the leaves of the cucumber. After spraying, the plant was air-dried. After 1 day, an aqueous suspension containing spores of cucumber target leaf spot fungus (*Corynespora cassiicola*) was sprayed to inoculate the spores. After the inoculation, the plant was cultivated in a greenhouse at 24° C. in the daytime and 20° C. at night for 7 days, and then the area of lesion was investigated. As a result, the area of lesion on the plant treated with the present compound 1, 2, 3, 7, 8, 9, 10, or 11 was 30% or less of that on an untreated plant.

Test Example 6

Each of the compounds 1, 3, 7, 8, and 9 obtained in Formulation Example 5 was diluted with water so as to adjust the concentration of each compound to 500 ppm to obtain a dilution.

About 30 heads of cotton aphid (*Aphis gossypii*) (including all stages) were inoculated on cucumber seedlings (first true-leaf stage) planted in each of the plastic cups and, after being placed for 1 day, 20 mL of the dilution was sprayed over the seedlings.

After 6 days, the number of surviving cotton aphid parasitizing to the leaves of the cucumber was counted and the control value was calculated by the following equation.

Control value(%)={1−(Cb×Tai)/(Cai×Tb)}×100 wherein symbols in the equation represent the followings:
Cb: Number of insects before treatment in untreated area;
Cai: Number of surviving parasites in untreated area during observation;
Tb: Number of insects before treatment in treated area; and
Tai: Number of surviving parasites in treated area during observation.

As used herein, the untreated area means an area where a solution prepared by diluting a formulation containing no present compound with the same amount of water as in the treated area in Formulation Example 5 was sprayed.

As a result, all treated areas using the test chemical solution of the compound 1, 3, 7, 8, or 9 showed 80% or more of the control value.

The present compound has control activity against pests and is useful as an active ingredient of a pest control agent.

The invention claimed is:

1. A tetrazolinone compound represented by formula (1):

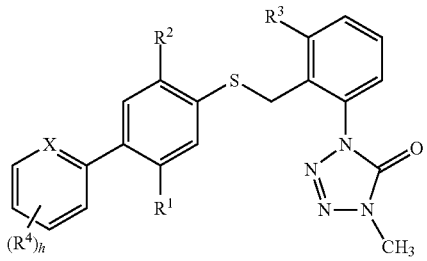

wherein $R^1$ and $R^2$ each independently represents a hydrogen atom, a halogen atom, a C1-C4 alkyl group optionally having one or more halogen atoms, or a C1-C4 alkoxy group optionally having one or more halogen atoms;
$R^3$ represents a hydrogen atom, a halogen atom, a C1-C4 alkyl group optionally having one or more halogen atoms, a C3-C4 cycloalkyl group optionally having one or more halogen atoms, or a C1-C4 alkoxy group optionally having one or more halogen atoms;
$R^4$ represents a halogen atom, a C1-C4 alkyl group optionally having one or more halogen atoms, a C1-C4 alkoxy group optionally having one or more halogen atoms, or a cyano group;
h represents any one of integers of 0 to 4 in which when h is an integer of 2 or more, each $R^4$ may be the same as or different from the other at least one $R^4$; and
X represents a nitrogen atom.

2. A pest control agent comprising the tetrazolinone compound as defined in claim 1.

3. A method for controlling pests, which comprises applying an effective amount of the tetrazolinone compound as defined in claim 1 to plants or soil.

* * * * *